US010519237B2

(12) United States Patent
Eisenbach-Schwartz et al.

(10) Patent No.: US 10,519,237 B2
(45) Date of Patent: *Dec. 31, 2019

(54) REDUCING SYSTEMIC REGULATORY T CELL LEVELS OR ACTIVITY FOR TREATMENT OF DISEASE AND INJURY OF THE CNS

(71) Applicant: Yeda Research and Development Co. Ltd, Rehovot (IL)

(72) Inventors: Michal Eisenbach-Schwartz, Rehovot (IL); Kuti Baruch, Rehovot (IL); Neta Rosenzweig, Rehovot (IL)

(73) Assignee: Yeda Research and Development Co. Ltd, Rehovot (IL)

( * ) Notice: Subject to any disclaimer, the term of this patent is extended or adjusted under 35 U.S.C. 154(b) by 514 days.

This patent is subject to a terminal disclaimer.

(21) Appl. No.: 15/261,945

(22) Filed: Sep. 10, 2016

(65) Prior Publication Data

US 2017/0029508 A1 Feb. 2, 2017

Related U.S. Application Data

(63) Continuation-in-part of application No. PCT/IL2016/050750, filed on Jul. 13, 2016, and a continuation-in-part of application No. 14/850,794, filed on Sep. 10, 2015, now Pat. No. 10,214,585, which is a continuation-in-part of application No. 14/797,894, filed on Jul. 13, 2015, now Pat. No. 9,856,318, which is a continuation-in-part of application No. PCT/IL2015/050265, filed on Mar. 12, 2015.

(60) Provisional application No. 62/279,622, filed on Jan. 15, 2016, provisional application No. 62/353,549, filed on Jun. 22, 2016, provisional application No. 62/358,530, filed on Jul. 5, 2016, provisional application No. 62/030,164, filed on Jul. 29, 2014, provisional application No. 61/951,783, filed on Mar. 12, 2014.

(51) Int. Cl.
| | |
|---|---|
| *C07K 16/28* | (2006.01) |
| *A61K 39/395* | (2006.01) |
| *A61K 45/06* | (2006.01) |
| *A61K 31/404* | (2006.01) |
| *A61K 31/4155* | (2006.01) |
| *A61K 31/7068* | (2006.01) |
| *A61K 33/36* | (2006.01) |
| *A61K 39/00* | (2006.01) |

(52) U.S. Cl.
CPC ........ *C07K 16/2818* (2013.01); *A61K 31/404* (2013.01); *A61K 31/4155* (2013.01); *A61K 31/7068* (2013.01); *A61K 33/36* (2013.01); *A61K 39/395* (2013.01); *A61K 39/39541* (2013.01); *A61K 45/06* (2013.01); *C07K 16/2803* (2013.01); *C07K 16/2827* (2013.01); *A61K 2039/505* (2013.01); *A61K 2039/507* (2013.01); *A61K 2039/545* (2013.01); *A61K 2039/572* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 7,563,869 B2 | 7/2009 | Honjo et al. | |
| 8,008,449 B2 | 8/2011 | Korman et al. | |
| 8,552,154 B2 | 10/2013 | Freeman et al. | |
| 8,629,098 B2 | 1/2014 | Fahmy et al. | |
| 8,709,416 B2 | 4/2014 | Langermann et al. | |
| 8,735,553 B1 | 5/2014 | Li et al. | |
| 8,779,105 B2 | 7/2014 | Korman et al. | |
| 8,900,587 B2 | 12/2014 | Carven et al. | |
| 8,927,697 B2 | 1/2015 | Davis et al. | |
| 8,945,561 B2 | 2/2015 | Davis et al. | |
| 8,952,136 B2 | 2/2015 | Carven et al. | |
| 8,993,731 B2 | 3/2015 | Tyson et al. | |
| 9,085,625 B2 | 7/2015 | Labrijn et al. | |
| 9,394,365 B1 | 7/2016 | Eisenbach-Schwartz | |
| 15,202,493 | 7/2016 | Eisenbach-Schwartz | |
| 15,212,231 | 7/2016 | Eisenbach-Schwartz | |
| 9,512,225 B2 | 12/2016 | Eisenbach-Schwartz | |
| 9,512,227 B2 | 12/2016 | Eisenbach-Schwartz | |
| 9,534,052 B2 | 1/2017 | Eisenbach-Schwartz | |

(Continued)

FOREIGN PATENT DOCUMENTS

| | | |
|---|---|---|
| EP | 1575484 B1 | 5/2003 |
| EP | 2320940 B1 | 11/2009 |

(Continued)

OTHER PUBLICATIONS

U.S. Appl. No. 16/284,081, filed Feb. 2019, Eisenbach-Schwartz; Michal.*

(Continued)

*Primary Examiner* — Ilia I Ouspenski

(74) *Attorney, Agent, or Firm* — UltimatEdge IP Law Group, P.C.; Dean G. Stathakis

(57) ABSTRACT

The present specification discloses a pharmaceutical composition comprising an active agent that causes reduction of the level of systemic immunosuppression in an individual for use in treating a disease, disorder, condition or injury of the CNS. The pharmaceutical composition is administered by a dosage regimen comprising at least one course of therapy, each course of therapy comprising in sequence a treatment session followed by an interval session of non-treatment.

30 Claims, 31 Drawing Sheets

Specification includes a Sequence Listing.

(56) References Cited

U.S. PATENT DOCUMENTS

| | | | |
|---|---|---|---|
| 9,856,318 B2 | 1/2018 | Eisenbach-Schwartz | |
| 9,982,047 B2 | 5/2018 | Eisenbach-Schwartz et al. | |
| 9,982,048 B2 | 5/2018 | Eisenbach-Schwartz et al. | |
| 9,982,049 B2 | 5/2018 | Eisenbach-Schwartz et al. | |
| 9,982,050 B2 | 5/2018 | Eisenbach-Schwartz et al. | |
| 9,982,051 B2 | 5/2018 | Eisenbach-Schwartz et al. | |
| 10,144,778 B2* | 12/2018 | Eisenbach-Schwartz | A61K 38/005 |
| 10,214,585 B2* | 2/2019 | Eisenbach-Schwartz | A61K 38/005 |
| 2010/0061992 A1 | 3/2010 | Anderson et al. | |
| 2014/0004081 A1 | 1/2014 | Cobbold et al. | |
| 2014/0023614 A1 | 1/2014 | Barawkar et al. | |
| 2014/0044738 A1 | 2/2014 | Langermann et al. | |
| 2014/0093511 A1 | 4/2014 | Lonberg et al. | |
| 2014/0099254 A1 | 4/2014 | Chang et al. | |
| 2014/0127227 A1 | 5/2014 | Chang et al. | |
| 2014/0212446 A1 | 7/2014 | Riley et al. | |
| 2014/0220021 A1 | 8/2014 | Shibayama et al. | |
| 2014/0227180 A1 | 8/2014 | Govindan et al. | |
| 2014/0234296 A1 | 8/2014 | Sharma et al. | |
| 2014/0234331 A1 | 8/2014 | Korman et al. | |
| 2014/0271540 A1 | 9/2014 | Stogniew et al. | |
| 2014/0271677 A1 | 9/2014 | Palese et al. | |
| 2014/0294759 A1 | 10/2014 | Chu et al. | |
| 2014/0294765 A1 | 10/2014 | Cojocaru et al. | |
| 2014/0294852 A1 | 10/2014 | Korman et al. | |
| 2014/0302070 A1 | 10/2014 | Chen et al. | |
| 2014/0314714 A1 | 10/2014 | Honjo et al. | |
| 2014/0328833 A1 | 11/2014 | Korman et al. | |
| 2014/0335048 A1 | 11/2014 | Stogniew et al. | |
| 2014/0335093 A1 | 11/2014 | Olive | |
| 2014/0341920 A1 | 11/2014 | Noelle | |
| 2014/0348743 A1 | 11/2014 | Korman et al. | |
| 2014/0348786 A1 | 11/2014 | Berzofsky et al. | |
| 2014/0356363 A1 | 12/2014 | Zhou et al. | |
| 2014/0377250 A1 | 12/2014 | Bantia | |
| 2014/0377253 A1 | 12/2014 | Harding et al. | |
| 2014/0377334 A1 | 12/2014 | Irvine et al. | |
| 2015/0004175 A1 | 1/2015 | Kaech et al. | |
| 2015/0017194 A1 | 1/2015 | Akahata et al. | |
| 2015/0018516 A1 | 1/2015 | Govindan et al. | |
| 2015/0079109 A1 | 3/2015 | Li et al. | |
| 2015/0086584 A1 | 3/2015 | Gilboa et al. | |
| 2015/0118222 A1 | 4/2015 | Levy et al. | |
| 2015/0118234 A1 | 4/2015 | Honjo et al. | |
| 2015/0132290 A1 | 5/2015 | Fuchs et al. | |
| 2015/0152180 A1 | 6/2015 | Davis et al. | |
| 2015/0165021 A1 | 6/2015 | Mashal et al. | |
| 2015/0166661 A1 | 6/2015 | Chen et al. | |
| 2015/0183875 A1 | 7/2015 | Cobbold et al. | |
| 2015/0203560 A1 | 7/2015 | Grewal et al. | |
| 2015/0203579 A1 | 7/2015 | Papadopoulos et al. | |
| 2015/0210769 A1 | 7/2015 | Freeman et al. | |
| 2015/0216970 A1 | 8/2015 | Grogan et al. | |
| 2015/0218274 A1 | 8/2015 | Sabatos-Peyton et al. | |
| 2016/0000909 A1 | 1/2016 | Eisenbach-Schwartz | |
| 2016/0008463 A1 | 1/2016 | Eisenbach-Schwartz | |
| 2017/0240634 A1 | 8/2017 | Eisenbach-Schwartz | |
| 2018/0009893 A1* | 1/2018 | Eisenbach-Schwartz | C07K 16/2827 |

FOREIGN PATENT DOCUMENTS

| | | |
|---|---|---|
| WO | 2005046719 A1 | 5/2005 |
| WO | 2006121168 A1 | 11/2006 |
| WO | 2007005874 A2 | 1/2007 |
| WO | 2012075291 A1 | 6/2012 |
| WO | 2014037952 A1 | 3/2014 |
| WO | 2014045305 A1 | 3/2014 |
| WO | 2014059251 A1 | 4/2014 |
| WO | 2014066527 A2 | 5/2014 |
| WO | 2014071402 A1 | 5/2014 |
| WO | 2014074852 A1 | 5/2014 |
| WO | 2014127917 A1 | 8/2014 |
| WO | 2014134355 A1 | 9/2014 |
| WO | 2014144791 A2 | 9/2014 |
| WO | 2014144885 A2 | 9/2014 |
| WO | 2014179664 A2 | 11/2014 |
| WO | 2014183066 A2 | 11/2014 |
| WO | 2014186035 A1 | 11/2014 |
| WO | 2014206107 A1 | 12/2014 |
| WO | 2014209804 A1 | 12/2014 |
| WO | 2015009856 A2 | 1/2015 |
| WO | 2015018528 A1 | 2/2015 |
| WO | 2015024042 A1 | 2/2015 |
| WO | 2015024060 A1 | 2/2015 |
| WO | 2015026684 A1 | 2/2015 |
| WO | 2015036394 A1 | 3/2015 |
| WO | 2015058573 A1 | 4/2015 |
| WO | 2015063187 A1 | 5/2015 |
| WO | 2015082499 A2 | 6/2015 |
| WO | 2015084721 A1 | 6/2015 |
| WO | 2015085210 A1 | 6/2015 |
| WO | 2015085847 A1 | 6/2015 |
| WO | 2015095895 A1 | 6/2015 |
| WO | 2015103072 A1 | 7/2015 |
| WO | 2015103602 A1 | 7/2015 |
| WO | 2015117002 A1 | 8/2015 |
| WO | 2015136541 A1 | 9/2015 |
| WO | 2017009829 A1 | 1/2017 |
| WO | 2017042633 A1 | 3/2017 |

OTHER PUBLICATIONS

U.S. Appl. No. 16/167,226, filed Oct. 2018, Eisenbach-Schwartz; Michal.*

Finnefrock, et al., PD-1 Blockade in Rhesus Macaques: Impact on Chronic Infection and Prophylactic Vaccination, J Immunol. 182(2): 980-987 (2009).

Shimmura-Tomita, et al., Galectin-9-Mediated Protection from Allo-Specific T Cells as a Mechanism of Immune Privilege of Corneal Allografts, PLoS ONE 8(5): e63620, pp. 1-11. (2013).

Newell et al "Imaging resolution and transient clinical improvement following cyclophosphamide treatment of a cerebral amyloid angiopathy-related lesion", Alzheimer's & Dementia, vol. 8, No. 4, Jul. 1, 2012 (Jul. 1, 2012), pp. S775-S776.

Ohaegbulam, KC., et al., "Human cancer immunotherapy with antibodies to the PD-1 and PD-L1 pathway," Trends in molecular medicine 21: 24-33. (2015).

Pardoll, DM., et al., "The blockade of immune checkpoints in cancer immunotherapy," Nature reviews Cancer 12: 252-264. (2012).

Peng W, et al., "PD-1 blockade enhances T-cell migration to tumors by elevating IFN-gamma inducible chemokines," Cancer research 72: 5209-5218. (2012).

Pere H., et al., "A CCR4 antagonist combined with vaccines induces antigen-specific CD8+ T cells and tumor immunity against self antigens," Blood, 118: 4853-4862. (2011).

Qin A., et al., "MicroRNA-126 regulates the induction and function of CD4(+) Foxp3(+) regulatory T cells through PI3K/AKT pathway," Journal of cellular and molecular medicine 17: 252-264.

Reiss et al., "Harnessing the power of the immune system via blockade of PD-1 and PD-L1: a promising new anticancer strategy," Immunotherapy, (2014), 6(4) pp. 459-475.

Sakuishi, et al., "Targeting Tim-3 and PD-1 pathways to reverse T cell exhaustion and restore anti-tumor immunity," J. Exp. Med., 2010, vol. 207, pp. 2187-2194.

Schreiber RD, Old LJ, Smyth MJ; "Cancer immunoediting: integrating immunity's roles in cancer suppression and promotion". Science 331: 1565-1570. (2011).

Schwartz M, Baruch K; Breaking peripheral immune tolerance to CNS antigens in neurodegenerative diseases: boosting autoimmunity to fight-off chronic neuroinflammation, J. Autoimmun., 2014, vol. 54, pp. 8-14, (Abstract Only).

Schwartz M, Baruch K; "The resolution of neuroinflammation in neurodegeneration: leukocyte recruitment via the choroid plexus". The EMBO journal 33: 7-22.(2014b).

(56) References Cited

OTHER PUBLICATIONS

Shevchenko, I., et al., "Low-dose gemcitabine depletes regulatory T cells and improves survival in the orthotopic Panc02 model of pancreatic cancer," International journal of cancer Journal international du cancer 133: 98-107. (2013).
Simpson, TR., et al, "Fc-dependent depletion of tumor-infiltrating regulatory T cells co-defines the efficacy of anti-CTLA-4 therapy against melanoma," The Journal of experimental medicine 210: 1695-1710. (2013).
Smith, PM., et al., "The microbial metabolites, short-chain fatty acids, regulate colonic Treg cell homeostasis". Science 341: 569-573. (2013).
Terme, M., et al., "Modulation of immunity by antiangiogenic molecules in cancer". Clinical & developmental Immunology 2012: 492920. (2012).
Thomas-Schoemann A., et al., "Arsenic trioxide exerts antitumor activity through regulatory T cell depletion mediated by oxidative stress in a murine model of colon cancer," Journal of immunology 189: 5171-5177, (2012).
Voo, KS., et al., "Antibodies targeting human OX40 expand effector T cells and block inducible and natural regulatory T cell function". Journal of immunology 191: 3641-3650. (2013).
Wang et al., "PD1 blockade reverses the suppression of melanoma antigen-specific CTL by CD4+cd25 Hi regulatory T cells," International Immunology, 2009, vol. 21, No. 9, pp. 1065-1077.
Ward, FJ., et al., "The soluble isoform of CTLA-4 as a regulator of T-cell responses," European journal of immunology 43: 1274-1285. (2013).
Wainwright et al "Targeting Tregs in Malignant Brain Cancer: Overcoming IDO", Frontiers in Immunology, vol. 4, Jan. 1, 2013 (Jan. 1, 2013), pp. 1-17.
Weiskopf, K., et al., "Improving macrophage responses to therapeutic antibodies by molecular engineering of SIRPalpha variants," Oncoimmunology 2: e25773. (2013).
Written Opinion of the International Searching Authority and International Search Report, PCT/I L2015/050265, dated Sep. 29, 2015.
Zheng H, et al., "New approaches to treating Alzheimer's disease," Perspectives in medicinal chemistry 7: 1-8. (2015).
Zhu et al "p300 exerts an epigenetic role in chronic neuropathic pain through its acetyltransferase activity in rats following chronic constriction injury (CCI)", Molecular Pain, Biomed Central, London, GB, vol. 8, No. 1, Nov. 23, 2012 (Nov. 23, 2012), p. 84.
Zhu et al., "TIM-3 and Its Regulatory Role in Immune Responses," Curr Top Microbio Immunol., 350, 2010, pp. 1-15.
Intlekofer, et al., Preclinical Rationale for CTLA-4 and PD-1 Blockage as Cancer Immunotherapy, J. Leukoc. Biol. 94(1): 25-39 (2013).
Leung, et al., The CD28-B7 Family in Anti-Tumor Immunity: Emerging Concepts in Cancer Immunitherapy, Immune Network 14(6): 265-276 (2014).
McDermott, et al., PD-1 as a Potential Target in Cancer Therapy, Cancer Med. 2(5): 662-673 (2013).
Sakthivel, et al., Attenuation of Immune-Mediated Influenza Pneumonia by Targeting the Inducible Co-Stimulator (ICOS) Molecule on T Cells, PLoS ONE 9(7): e100970, pp. 1-11 (2014).
Simpson, et al., Regulation of CD4 T Cell Activation and Effector Function by Inducible Costimulator (ICOS), Curr. Opin. Immunol. 22: 326-332 (2010).
Jin, et al., Role of PD-1 in Regulating T-Cell Immunity, Curr. Top. Microbiol. Immunol. 350: 17-37 (2011).
U.S. Appl. No. 14/797,894, filed Jul. 13, 2015, Mar. 12, 2014, 2016/0000909, U.S. Pat. No. 9,856,318.
U.S. Appl. No. 14/957,065, filed Dec. 2, 2015, Mar. 12, 2014, U.S. Pat. No. 9,394,365.
U.S. Appl. No. 15/190,160, filed Jun. 22, 2016, Mar. 12, 2014, U.S. Pat. No. 9,512,225.
U.S. Appl. No. 15/202,493, filed Jul. 5, 2016, Mar. 12, 2014, U.S. Pat. No. 9,512,227.
U.S. Appl. No. 15/212,231, filed Jul. 16, 2016, Mar. 12, 2014, 2016/0319021, U.S. Pat. No. 9,534,052.
U.S. Appl. No. 15/125,249, filed Sep. 12, 2016, Mar. 12, 2014, 2017/0240634.
U.S. Appl. No. 15/821,570, filed Nov. 22, 2017, Mar. 12, 2014.
U.S. Appl. No. 15/821,595, filed Nov. 22, 2017, Mar. 12, 2014.
U.S. Appl. No. 15/821,603, filed Nov. 22, 2017, Mar. 12, 2014.
U.S. Appl. No. 15/821,672, filed Nov. 22, 2017, Mar. 12, 2014.
U.S. Appl. No. 14/850,794, filed Sep. 10, 2015, Mar. 12, 2014, 2016/0008463.
U.S. Appl. No. 15/821,678, filed Nov. 22, 2017, Mar. 12, 2014.
U.S. Appl. No. 15/698,800, filed Sep. 8, 2017, Mar. 12, 2014.
Baruch, et al., CNS-Specific T Cells Shape Brain Function via the Choroid Plexus, Brain Behav. Immun. 34: 11-16 (2013).
Baruch, et al., Cerebral Nitric Oxide Represses Choroid Plexus NFkB-Dependent Gateway Activity for Leukocyte Trafficking, EMBO J. 34(13): 1816-1828 (2015).
Baruch, et al., Breaking Immune Tolerance by Targeting Foxp3+ Regulatory T Cells Mitigates Alzheimer's Disease Pathology, Nat. Commun. 6(7967): 1-12 (2015).
Guo, et al., Alzheimer's Disease and Retinal Neurodegeneration, Cur. Alzheimer Res. 7: 1-12 (2010).
Kawamoto, et al., Expression and Function of Inducible Co-Stimulator in Patients with Systemic Lupus Erythematosus: Possible Involvement in Excessive Interferon-γ and Anti-Double-Stranded DNA Antibody Production, Arthritis Res. Ther. 8(3): 1-14 (2006).
Kunis, et al., Immunization with a Myelin-Derived Antigen Activates the Brain's Choroid Plexus for Recruitment of Immunoregulatory Cells to the CNS and Attenuates Disease Progression in a Mouse Model of ALS, J. Neurosci. 35 (16): 6381-6393 (2015).
Quiroga, et al., Inducible Costimulator: A Modulator of IFN-gamma Production in Human Tuberculosis, J. Immunol. 176: 5965-5974 (2006).
Sharpe, et al., The B7-CD28 Superfamily, Nat. Rev. Immunol. 2: 116-126 (2002).
WIPO, PCTForm IB373 International Preliminary Report on Patentability for PCT/IL2015/050265, dated Sep. 22, 2016.
WIPO, PCT Form ISA210 International Search Report for PCT/IL2016/050750, dated Nov. 4, 2016.
WIPO, PCT Form ISA237 Written Opinion of the International Searching Authority for PCT/IL2016/050750, dated Nov. 4, 2016.
WIPO, PCT Form ISA210 International Search Report for PCT/IB2016/001433, dated May 26, 2017.
WIPO, PCT Form ISA237 Written Opinion of the International Searching Authority for PCT/IB2016/001433, dated May 26, 2017.
Adapt-FS Research Group, "Follow-up evaluation of cognitive function in the randomized Alzheimer's Disease Anti-inflammatory Prevention Trial and its Follow-up Study," Alzheimer's & Dementia No. 11, pp. 216-225, (2015).
Adapt-FS Research Group, "Naproxen and celecoxib do not prevent AD in early results from randomized controlled trial," Neurology, No. 68, pp. 1800-1808 (2007).
Aisen, et al., "Effects of Rofecoxib or Naproxen vs Placebo on Alzheimer Disease Progression, A Randomized Controlled Trial," JAMA, vol. 289, No. 21, pp. 2819-2826.
Arvanitakis, et al., "Relation of NSAIDs to incident AD, change in cognitive function, and AD pathology," Neurology, No. 70, pp. 2219-2225 (2008).
Baruch et al., "Therapeutic potential of PD-1 immune checkpoint blockade in Alzheimer's disease," Dept. of Neurobiology, Weizmann Institute of Science, 1-12.
Baruch et al., "CNS-specific immunity at the choroid plexus shifts toward destructive Th2 inflammation in brain aging," PNAS, vol. 110, No. 6, pp. 2264-2269, (Feb. 2013).
Baruch, et al., Aging-induced type 1 Interferon response at the choroid plexus negatively affects brain function, Science, vol. 346, No. 1., pp. 89-93, (2014).
Baruch, et al., "PD-1 immune checkpoint blockade reduces pathology and improves memory in mouse models of Alzheimer's disease," Nature Medicine, vol. 22, No. 2, pp. 135-139 (Feb. 2016).
Bodhankar, et al., "Targeting immune co-stimulatory effects of PD-L1 and PD-L2 might represent an effective therapeutic strategy in stroke," Frontiers in Cellular Neuroscience, Original Research Article, vol. 8, Article 228, 1-14, (2014).

(56) References Cited

OTHER PUBLICATIONS

Butovsky, O., et al., Glatiramer acetate fights against Alzheimer's disease by inducing dendritic-like microglia expressing insulin-like growth factor 1, PNAS, vol. 103, No. 31, 11784-11789, Israel, (2006).
He, F., et al., "The role of regulatory T cells in neurodegenerative diseases," WIREs Syst Biol Med., vol. 5, 153-180, (2013).
Kroner, A., et al., "PD-1 Regulates Neural Damage in Oligodendroglia-Induced Inflammation," PLOS One, vol. 4, Issue 2, e4405, Israel, (2009).
Kunis, G., "IFN-γ-dependent activation of the brain's choroid plexus for CNS immune surveillance and repair," Brain, vol. 136, pp. 3427-3440, (2013).
Raynor, J., et al., "Homeostasis and function of regulatory T cells in aging," Elsevier, Current Opinion in Immunology, 24, 482-487, (2012).
Reines, S.A., et al., "No effect on Alzheimer's disease in a 1-year, randomized, blinded, controlled study," Neorology, No. 62, (Jan. 2004), pp. 66-71.
Ren, X., et al., "Programmed Death-1 Pathway Limits Central Nervous System Inflammation and Neurologic Deficits in Murine Experimental Stroke," PD-1/PD-L Pathway Limits Experimental Stroke, 2578-2583 (2011).
Rosenkranz, D., et al., "Higher frequency of regulatory T cells in the elderly and increased suppressive activity in neurodegeneration," Elsevier, Journal of Neuroimmunology, 188, 117-127, (2007).
Salama, A., "Critical Role of the Programmed Death-1 (PD-1) Pathway in Regulation of Experimental Autoimmune Encephalomyelitis," J. Exp. Med., vol. 198, No. 1, 71-78, (2003).
Saresella, M., et al., "PD1 Negative and PD1 Positive CD4+ T Regulatory Cells in Mild Cognitive Impairment and Alzheimer's Disease," Journal of Alzheimers Disease, 21, 927-938, (2010).
Saresella, M., et al., "A potential role for the PD1/PD-L1 pathway in the neuroinflammation of Alzheimer's disease," Elsevier, Neurobiology of Aging, 33, 624.e11-624e22, (2012).
Schwartz, M., et al., "Therapeutic T Cell-Based Vaccination for Neurodegenerative Disorders, The Role of CD4+ CD25 + Regulatory T cells," Dept. of Neurobiology, The Weizmann Institute of Science, Annals New York Academy of Sciences, 1051, 701-708 (2005).
Shecter, R., et al., "Infiltrating Blood-Derived Macrophages Are Vital Cells Playing an Anti-inflammatory Role in Recovery from Spinal Cord Injury in Mice," PLoS Medicine, vol. 6, Issue 1, pp. 1-17, (Jul. 2009).
Wang, C., et al., "Down-Modulation of programmed Death 1 Alters Regulatory T Cells and Promotes Experimental Autoimmune Encephalomyelitis," Journal of Neuroscience Research, 88, 7-15 (2010).
Webster, et al., "Frontiers in genetics," vol. 5, Article 88 (2014).
Ziv, Y., et al., "Immune cells contribute to the maintenance of neurogenesis and spatial learning abilities in adulthood," Nature Neuroscience, vol. 9, No. 2, pp. 268-275 (Feb. 2006).
Zha, J., et al., "Chronic thoracic spinal cord injury impairs CD8+ T-cell function by up-regulating programmed cell death-1 expression," Journal of Neuroinflammation, vol. 11, No. 65, 1-18 (2014).
Zhao, S., et al., "Regulation of neuroinflammation through programmed death-1/programed death ligand signaling in neurological disorders," Frontiers in Cellular Neuroscience, vol. 8, Article 271, 1-7, (2014).
Angelov et al "Therapeutic Vaccine for Acute and Chronic Motor Neuron Diseases: Implications for Amyotrophic Lateral Sclerosis", Proceedings of the National Academy of Sciences, National Academy of Sciences, US, vol. 100, No. 8, Apr. 15, 2003 (Apr. 15, 2003), pp. 4790-4795.
Anderson et al., "Lag-3, Tim-3, and TIGIT: Co-inhibitory Receptors with Specialized Functions in Immune Regulation," Immunity, 2016, 44, pp. 989-1004.
Avidan et al "Vaccination with autoantigen protects against aggregated [beta]-amyloid and glutamate toxicity by controlling microglia: Effect of CD4 +CD25 + T cells", European Journal of Immunology, Wiley—V C H Verlag GMBH & Co. KGAA, DE, vol. 34, No. 12, Dec. 1, 2004 (Dec. 1, 2004), pp. 3434-3445.
Bai, A., et al., "All-trans retinoic acid down-regulates inflammatory responses by shifting the Treg/Th17 profile in human ulcerative and murine colitis." Journal of leukocyte biology 86: 959-969. (2009).
Bodhankar et al "PD-L 1 enhances CNS inflammation and infarct volume following experimental stroke in mice in opposition to PD-1", Journal of Neuroinflammation, Biomed Central Ltd., London, GB, vol. 10, No. 1, Sep. 9, 2013 (Sep. 9, 2013), p. 111.
Bowers, EM et al., "Virtual ligand screening of the p300/CBP histone acetyltransferase: identification of a selective small molecule inhibitor". Chemistry & biology 17: 471-482. (2010).
Brestoff, JR, et al., "Commensal bacteria at the interface of host metabolism and the immune system". Nature immunology 14: 676-684. (2013).
Butovsky et al "Selective ablation of bone marrow-derived dendritic cells increases amyloid plaques in a mouse Alzheimer's disease model", European Journal of Neuroscience, vol. 26, No. 2, Jul. 10, 2007 (Jul. 10, 2007), pp. 413-416.
Colombo, MP, et al., "Regulatory-T-cell inhibition versus depletion: the right choice in cancer immunotherapy". Nature reviews Cancer 7: 880-887. (2007).
Boyne, GO, et al. "Adding fuel to the tire: Immunogenic intensification". Human vaccines & immunotherapeutics 10: 3306-3312.(2014).
Dalotto-Moreno T, "Targeting galectin-1 overcomes breast cancer-associated immunosuppression and prevents metastatic disease," Cancer research 73: 1107-1117. (2013).
Duraiswamy, J., et al., "Dual blockade of PD-1 and CTLA-4 combined with tumor vaccine effectively restores T-cell rejection function in tumors—response." Cancer research 74: 633-634; discussion 635. (2014).
Francisco, LM, et al., "The PD-1 pathway in tolerance and autoimmunity". Immunological reviews 236: 219-242. (2010).
Galvin, KC, et al., "Blocking retinoic acid receptor-alpha enhances the efficacy of a dendritic cell vaccine against tumours by suppressing the induction of regulatory T cells". Cancer immunology, immunotherapy : CII 62: 1273-1282. (2013).
Ghiringhelli, F, et al., "Production of adenosine by ectonucleotidases: a key factor in tumor immunoescape". Journal of biomedicine & biotechnology 2012: 473712. (2012).
Heylmann et al "Human CD4+CD25+ Regulatory T Cells Are Sensitive to Low Dose Cyclophosphamide: Implications for the Immune Response", PLOS ONE, vol. 8, No. 12,Dec. 23, 2013 (Dec. 23, 2013), p. e83384.
Hirayama, M., et al., "Overcoming regulatory T-cell suppression by a lyophilized preparation of *Streptococcus pyogenes*". European journal of immunology 43: 989-1000. (2013).
Joller N., et al., "Immune checkpoints in central nervous system autoimmunity". Immunological reviews 248: 122-139. (2012).
Keimowitz "Dementia Improvement With Cytotoxic Chemotherapy a Case of Alzheimer Disease and Multiple Myeloma", Archives of Neurology, American Medical Association, Chicago, IL, US, vol. 54, No. 4, Apr. 1, 1997 (Apr. 1, 1997), pp. 485-488.
Kim PS., et al., "Pan-Bcl-2 inhibitor, GX15-070 (obatoclax), decreases human T regulatory lymphocytes while preserving effector T lymphocytes: a rationale for its use in combination immunotherapy." Journal of immunology 192: 2622-2633. (2014).
Liu Y., et al., "Inhibition of p300 impairs Foxp3(+) T regulatory cell function and promotes antitumor immunity," Nature medicine 19: 1173-1177. (2013).
Mellman, I., et al., "immunotherapy comes of age," Nature 480: 480-489. (2011).
Nebbia et al., "Upregulation of the Tim-3/Galectin-9 Pathway of T Cell Exhaustion in Chronic Hepatitis B Virus Infection," 2012, PLOS ONE, vol. 7 (10), e47648. doi:10.1371/journal.pone. 0047648, pp. 1-15.
Ju, et al., The TIM-3/Galectin-9 Pathway Involves in the Homeostatis of Hepatic Tregs in a Mouse Model of Concanavalin A-Induced Hepatitis, Mol. Immunol. 58: 85-91 (2014).
Raposo, et al., Central Nervous System Repair Requires Both Effector and Regulatory T Cells with Distinct Temporal and Spatial Profiles, J. Neuroimmunol. 275: 206, Abstract 115 (2014).

(56) References Cited

OTHER PUBLICATIONS

Wang, et al., TIM-3-Galectin-9 Pathway Involves the Suppression Induced by CD4+CD25+ Regulatory T Cells, Immunobiol. 214: 342-349 (2009).
Leitner, et al., TIM-3 Does not Act as a Receptor for Galectin-9, PLoS Pathog. 9(3): e1003253 pp. 12 (2013).

* cited by examiner

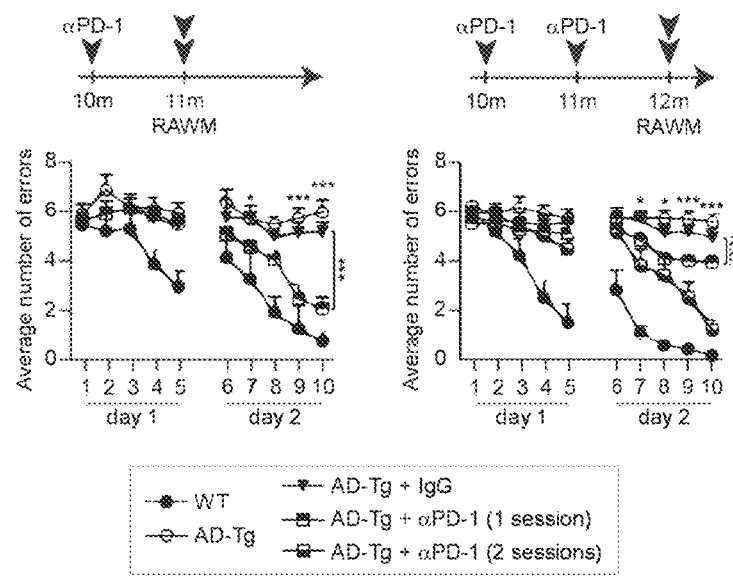

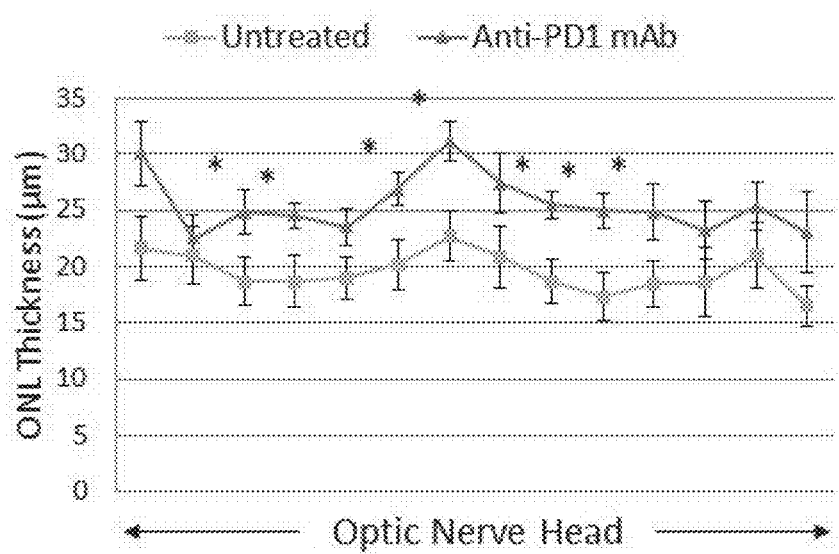

Fig. 23A
Fig. 23B
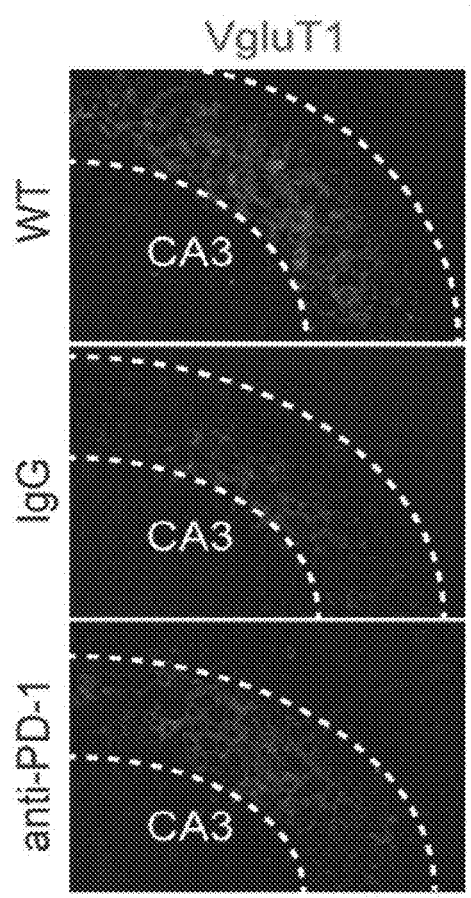
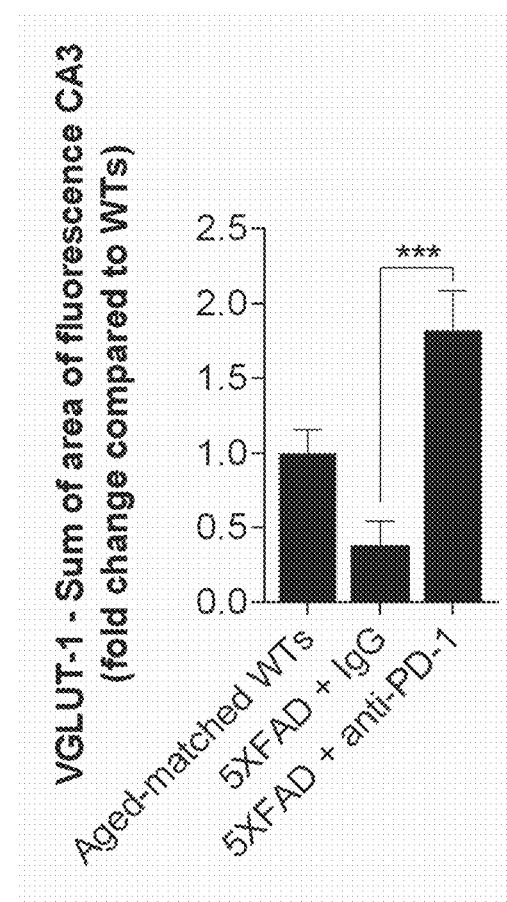

REDUCING SYSTEMIC REGULATORY T CELL LEVELS OR ACTIVITY FOR TREATMENT OF DISEASE AND INJURY OF THE CNS

CROSS-REFERENCE TO RELATED APPLICATIONS

The present application claims the benefit of priority and the filing date under 35 U.S.C. § 119(e) to U.S. Provisional Patent Application No. 62/279,622, filed Jan. 15, 2016, U.S. Provisional Patent Application No. 62/353,549, filed Jun. 22, 2016, and U.S. Provisional Patent Application No. 62/358,530, filed Jul. 5, 2016; and is a Continuation-in-Part that claims the benefit of priority and the filing date under 35 U.S.C. § 120 to International Patent Application No. PCT/IL2016/050750, filed Jul. 13, 2016; and is a Continuation-in-Part that claims the benefit of priority and the filing date under 35 U.S.C. § 120 U.S. patent application Ser. No. 14/850,794, filed Sep. 10, 2015, a continuation-in-part that claims priority to U.S. patent application Ser. No. 14/797,894, filed on Jul. 13, 2015, a Continuation-in-Part that claims priority to International Patent Application No. PCT/IL2015/050265, filed Mar. 12, 2015, in which the United States is designated, and claims the benefit of priority from U.S. Provisional Patent Application No. 61/951,783, filed Mar. 12, 2014, and U.S. Provisional Patent Application No. 62/030,164, filed Jul. 29, 2014, the entire content of each of which is hereby incorporated by reference in its entirety as if fully disclosed herein.

FIELD

The present invention relates in general to methods and compositions for treating disease, disorder, condition or injury of the Central Nervous System (CNS) by transiently reducing the level of systemic immunosuppression in the circulation.

BACKGROUND

Most central nervous system (CNS) pathologies share a common neuroinflammatory component, which is part of disease progression, and contributes to disease escalation. Among these pathologies is Alzheimer's disease (AD), an age-related neurodegenerative disease characterized by progressive loss of memory and cognitive functions, in which accumulation of amyloid-beta (Aβ) peptide aggregates was suggested to play a key role in the inflammatory cascade within the CNS, eventually leading to neuronal damage and tissue destruction (Akiyama et al, 2000; Hardy & Selkoe, 2002; Vom Berg et al, 2012). Despite the chronic neuroinflammatory response in neurodegenerative diseases, clinical and pre-clinical studies over the past decade, investigating immunosuppression-based therapies in neurodegenerative diseases, have raised the question as to why anti-inflammatory drugs fall short (Breitner et al, 2009; Group et al, 2007; Wyss-Coray & Rogers, 2012). We provide a novel answer that overcomes the drawbacks of existing therapies of AD and similar diseases and injuries of the CNS; this method is based on our unique understanding of the role of the different components of systemic and central immune system in CNS maintenance and repair.

SUMMARY

In one aspect, the present invention provides a pharmaceutical composition comprising an active agent that causes reduction of the level of systemic immunosuppression in an individual for use in treating a disease, disorder, condition or injury of the CNS that does not include the autoimmune neuroinflammatory disease, relapsing-remitting multiple sclerosis (RRMS), wherein said pharmaceutical composition is for administration by a dosage regimen comprising at least two courses of therapy, each course of therapy comprising in sequence a treatment session followed by an interval session of non-treatment.

In another aspect, the present invention provides a method for treating a disease, disorder, condition or injury of the Central Nervous System (CNS) that does not include the autoimmune neuroinflammatory disease relapsing-remitting multiple sclerosis (RRMS), said method comprising administering to an individual in need thereof a pharmaceutical composition comprising an active agent that causes reduction of the level of systemic immunosuppression according to the present invention, wherein said pharmaceutical composition is administered by a dosage regime comprising at least two courses of therapy, each course of therapy comprising in sequence a treatment session followed by an interval session of a non-treatment period.

BRIEF DESCRIPTION OF DRAWINGS

FIGS. 6C-E) show Morris water maze (MWM) test performance of 6-month old DTx-treated AD-Tg/Foxp3-DTR⁺ and control mice, 3 weeks alter the last DTx injection. Following transient Treg depletion, AD-Tg mice showed better spatial learning/memory performance in the (C) acquisition, (D) probe and (E) reversal phases of the MWM, relative to AD-Tg controls (n=7-9 per group; two-way repeated measures ANOVA followed by Bonferroni post-hoc analysis for individual pair comparisons; *, P<0.05 for overall acquisition, probe, and reversal). In all panels, error bars represent mean±s.e.m.; *, P<0.05; , P<0.01;*, P<0.001.

FIGS. 8B-D show mRNA expression levels of genes in the hippocampus of untreated AD-Tg mice, and AD-Tg mice treated with weekly-GA, at the age of 6 m, showing (B) reduced expression of pro-inflammatory cytokines such as TNF-α, IL-1β and IL-12p40, (C) elevation of the anti-inflammatory cytokines IL-10 and TGF-β, and of (D) the neurotropic factors, IGF-1 and BDNF, in weekly-GA treated mice (n=6-8 per group; Student's t test). In FIGS. 8E-G, AD-Tg mice (5 months old) were treated with either weekly-GA or with vehicle (PBS), and compared to age-matched WT littermates in the MWM task at the age of 6 m. Treated mice showed better spatial learning/memory performance in the acquisition (E), probe (F) and reversal (G) phases of the MWM, relative to controls (n=6-9 per group; two-way repeated measures ANOVA followed by Bonferroni post-hoc for individual pair comparisons; WT mice, black circles; AD-Tg controls, white circles; treated AD-Tg, grey circles). FIGS. 8H-I show cognitive performance of the same mice in the RAWM task, 1 month (H) or 2 months (I) following the last GA injection (n=6-9 per group; two-way repeated measures ANOVA followed by Bonferroni post-hoc for individual pair comparisons). Data are representative of at least three independent experiments. In all panels, error bars represent mean±s.e.m.; *, P<0.05; , P<0.01;*, P<0.001.

FIGS. 9D-E show representative images of brain sections from 6-month old AD-Tg/CX3CR1$^{GFP/+}$ BM chimeras following weekly-GA. CX₃CR1$^{GFP}$ cells were localized at the CP of the third ventricle (3V; i), the adjacent ventricular spaces (ii), and the CP of the lateral ventricles (LV; iii) in AD-Tg mice treated with weekly-GA (D; scale bar, 25 μm). Representative orthogonal projections of confocal z-axis stacks, showing co-localization of GFP⁺ cells with the myeloid marker, CD68, in the CP of 7-month old AD-Tg/CX₃CR1$^{GFP/+}$ mice treated with weekly-GA, but not in control PBS-treated AD-Tg/CX₃CR1$^{GFP/+}$ mice (E; scale bar, 25 μm). (F) CX₃CR1$^{GFP}$ cells are co-localized with the myeloid marker IBA-1 in brains of GA-treated AD-Tg/CX₃CR1$^{GFP/+}$ mice in the vicinity of Aβ plaques, and co-expressing the myeloid marker, IBA-1 (scale bar, 25 μm). FIGS. 9G-H show representative flow cytometry plots of cells isolated from the hippocampus of 4-month old WT, untreated AD-Tg, and AD-Tg mice, on the 2$^{nd}$ week of the weekly-GA regimen. CD11b$^{high}$/CD45$^{high}$ mo-MΦ were gated (G) and quantified (H; n=4-5 per group; one-way ANOVA followed by Newman-Keuls post hoc analysis). In all panels, error bars represent mean±s.e.m.; *, P<0.05; , P<0.01;*, P<0.001.

In FIGS. 10A-B, aged mice (18 months) were treated with either p300i or vehicle (DMSO) for a period of 1 week, and examined a day after cessation of treatment. Representative flow cytometry plots showing elevation in the frequencies of CD4+ T cells expressing IFN-γ in the spleen (A), and IFN-γ-expressing immune cell numbers in the CP (B), following p300i treatment. FIGS. 10C-E show representative microscopic images (C), and quantitative analysis, of Aβ plaque burden in the brains of 10-month old AD-Tg mice, which received either p300i or vehicle (DMSO) for a period of 1 week, and were subsequently examined after 3 additional weeks. Brains were immunostained for Aβ plaques and by Hoechst nuclear staining (n=5 per group; Scale bar, 250 μm). Mean Aβ plaque area and plaque numbers were quantified in the hippocampal DG (D) and the 5$^{th}$ layer of the cerebral cortex (E) (in 6 μm brain slices; n=5-6 per group; Student's t test). (F) Schematic representation of the p300i treatment (or DMSO as vehicle) administration regimen to the different groups of AD-Tg mice at the age of 7 months, in either 1 or 2 sessions. FIGS. 10G-H show the change mean of Aβ plaque percentage coverage of the cerebral cortex (5$^{th}$ layer) (G), and the change in mean cerebral soluble Aβ$_{1-40}$ and Aβ$_{1-42}$ protein levels (H), relative to the untreated AD-Tg group (Aβ$_{1-40}$ and Aβ$_{1-42}$ mean level in untreated group, 90.5±11.2 and 63.8±6.8 μg/mg total portion, respectively; n=5-6 per group; one-way ANOVA followed by Newman-Keuls post hoc analysis). In all panels, error bars represent mean±s.e.m.; *, $P<0.05$; , $P<0.01$; *, $P<0.001$.

FIGS. 12A-B show that PD-1 blockade mitigates cognitive decline in AD-Tg mice. 10-month old AD-Tg mice were i.p. injected on day 1 and day 4 with 250 ug of either anti-PD-1 or control IgG, and examined 1 or 2 months later for the effect on pathology with (A) showing performance of AD-Tg mice in the RAWM after 1 treatment session with anti-PD-1 or IgG control and (B) showing effect of single anti-PD-1 treatment session, or 2 sessions with a 1 month interval on performance. Single arrows indicate time points of treatment, and double arrows indicate time points of cognitive testing. Cognitive performance of anti-PD-1 and IgG treated mice, compared to age-matched WT and untreated AD-Tg mice, assessed by the average number of errors per day in the RAWM learning and memory task (n=6-8 per group; two-way repeated measures ANOVA followed by Bonferroni post-hoc for individual pair comparisons).

FIG. 20A-B shows thickness plots of the outer nuclear layer (ONL) throughout the entire retina measured in individual eyes of RCS rats treated by intravitreal injection with anti-PD1 mAb (n=6) or IgG (n=5) or through histological analysis based on H&E stain with showing both eyes (the injected eye and the contralateral-non injected eye) of (A) anti-PD1 mAb treated animals; and (B) IgG treated animals. Data is presented as mean±standard error values; Significant differences were determined through student T-test per each individual sampling point and are marked by asterisks (*P<0.05).

FIG. 23A-B shows PD-1 blockade enhances hippocampal synaptic plasticity in 5XFAD mice with (A) showing parasagittal brain sections immunostained for VgluT1 (red); and (B) showing a graph quantitating the staining in anti-PD-1 treated animals, IgG immune controls and aged-matched wild-type controls.

DETAILED DESCRIPTION

Figure 1A:
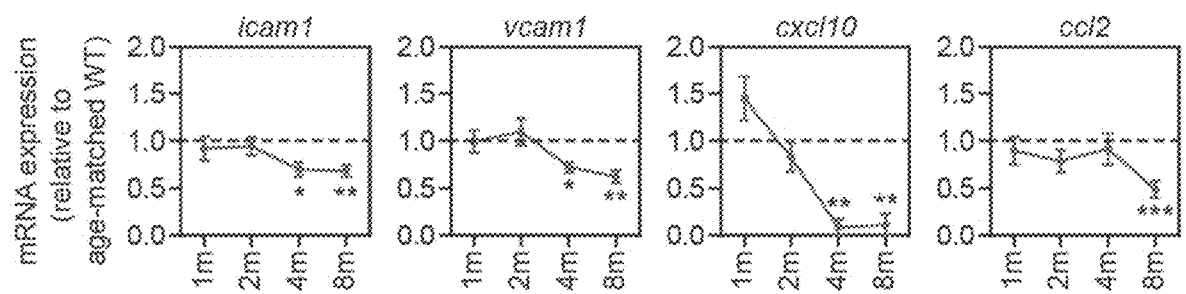
FIGS. 1A-B depict the choroid plexus (CP) activity along disease progression in the 5XFAD transgenic mouse model of AD (AD-Tg). (A) mRNA expression levels for the genes icam1, vcam1, cxcl10 and ccl2, measured by RT-qPCR, in CPs isolated from 1, 2, 4 and 8-month old AD-Tg mice, shown as fold-change compared to age-matched WT controls (n=6-8 per group; Student's t test for each time point). (B) Representative microscopic images of CPs of 8-month old AD-Tg mice and age-matched WT controls, immunostained for the epithelial tight junction molecule Claudin-1, Hoechst nuclear staining, and the integrin lignad, ICAM-1 (scale bar, 50 μm). In all panels, error bars represent mean±s.e.m.; *, $P<0.05$; , $P<0.01$;*, $P<0.001$.

Immune checkpoint mechanisms, which include cell-intrinsic downregulation of activated T cell responsiveness and effector function by inhibitory receptors, maintain systemic immune homeostasis and autoimmune tolerance (Joller et al, 2012; Pardoll, 2012). In recent years, blockade of these immune checkpoints, such as the programmed death-1 (PD-1) pathway (Francisco et al, 2010), has demonstrated notable anti-tumor efficacy, highlighting the potential of unleashing the power of the immune system in fighting various malignancies Recently, it was shown (WO 2015/136541; Baruch et al., 2016) that administration of anti-PD-1 antibodies to an animal model of Alzheimer's disease leads to clearance of Aβ, reversal of cognitive decline, and is associated with resolution of the neuroinflammatory response. Thus, systemic immunosuppression interferes with the ability to fight off AD pathology, and by releasing restrains on the systemic immune system, AD pathology could be mitigated.

Without wishing to be limited to any theory, immune checkpoint blockade activates a cascade of immunological events that starts in the periphery and culminates in numerous activities inside the brain. Initially, an immune response increases the availability of IFN-γ at the secondary lymphoid organs (lymph nodes, spleen, etc.) and circulating monocytes in the periphery. This immune response leads to the immunological activation of the brain's choroid plexus (CP), an epithelial layer at the brain ventricles, which forms the blood-cerebrospinal fluid-barrier (B-CSF-B), and serves as a selective gateway for leukocytes entering the CNS. The effect of the blockade of inhibitory immune checkpoints on CP gateway activity for leukocyte is mediated by the IFN-γ-induced expression of leukocyte trafficking molecules (adhesion molecules and chemokines) by the CP epithelium, which enables leukocyte trafficking. This increased expression leads to the recruitment of monocyte-derived macrophages and immunoregulatory cells to diseased sites within the brain. Importantly, this recruitment results in a comprehensive effect on brain function, including reduced of plaque burden, restored of immunological balance, resolved local inflammation, reduced gliosis, reduced synaptic loss, increased neurogenesis, increased neuronal protection and enhanced neuronal survival, collectively leading to neuroprotection and/or reduction in cognitive decline.

Immune checkpoints are molecules in the immune system that either turn up a signal (co-stimulatory molecules) or turn down a signal. Four stimulatory checkpoint molecules are members of the tumor necrosis factor (TNF) receptor superfamily—CD27, CD40, OX40, GITR and CD137. Another two stimulatory checkpoint molecules belongs to the B7-CD28 superfamily—CD28 itself and ICOS. Many inhibitor checkpoint molecules are known, including, without limitation, A2aR, B7-H3, B7-H4, BTLA, CTLA-4, IDO, KIR, LAG-3, PD-1, TIM-3 and VISTA.

The present invention provides a method for treating a disease, disorder, condition or injury of the Central Nervous System (CNS). In one embodiment, the disclosed method for treating a disease, disorder, condition or injury of the Central Nervous System (CNS) does not include the autoimmune neuroinflammatory disease relapsing-remitting multiple sclerosis (RRMS). The disclose method comprising administering to an individual in need thereof an active agent that causes reduction of the level of systemic immunosuppression, wherein said active agent is administered by a dosage regime comprising at least two courses of therapy, each course of therapy comprising in sequence a treatment session followed by an interval session of non-treatment.

In another aspect, the present invention is directed to an active agent that causes reduction of the level of systemic immunosuppression in an individual, or a pharmaceutical composition comprising the active agent, for use in treating a disease, disorder, condition or injury of the CNS that does not include the autoimmune neuroinflammatory disease, relapsing-remitting multiple sclerosis (RRMS), wherein said pharmaceutical composition is for administration by a dosage regimen comprising at least two courses of therapy, each course of therapy comprising in sequence a treatment session followed by an interval session of non-treatment.

In certain embodiments, the dosage regimen is calibrated such that the level of systemic immunosuppression is transiently reduced.

The term "treating" as used herein refers to means of obtaining a desired physiological effect. The effect may be therapeutic in terms of partially or completely curing a disease and/or symptoms attributed to the disease. The term refers to inhibiting the disease, i.e. arresting or slowing its development; or ameliorating the disease, i.e. causing regression of the disease.

The term "systemic presence" of regulatory or effector T cells as used herein refers to the presence of the regulatory or effector T cells (as measured by their level or activity) in the circulating immune system, i.e. the blood, spleen and lymph nodes. It is a well-known fact in the field of immunology that the cell population profile in the spleen is reflected in the cell population profile in the blood (Zhao et al, 2007).

The present treatment is applicable to both patients that show elevation of systemic immune suppression, as well as to patients that do not show such an elevation. Sometimes the individual in need for the treatment according to the present invention has a certain level of peripheral immunosuppression, which is reflected by elevated frequencies or numbers of Tregs in the circulation, and/or their enhanced functional activity and/or a decrease in IFNγ-producing leukocytes and/or decreased proliferation of leukocytes in response to stimulation. The elevation of frequencies or numbers of Tregs can be in total numbers or as percentage of the total CD4 cells. For example, it has been found in accordance with the present invention that an animal model of Alzheimer's disease has higher frequencies of Foxp3 out of CD4 cells as compared with wild-type mice. However, even if the levels of systemic Treg cells is not elevated, their functional activity is not enhanced, the level of IFNγ-producing leukocytes is not reduced or the proliferation of leukocytes in response to stimulation is not decreased, in said individual, the method of the present invention that reduces the level or activity of systemic immunosuppression is effective in treating disease, disorder, condition or injury of the CNS that does not include the autoimmune neuroinflammatory disease RRMS. Importantly, said systemic immune suppression can also involve additional immune cell types except of Tregs, such as myeloid-derived suppressor cells (MDSCs) (Gabrilovich & Nagaraj, 2009).

The level of systemic immunosuppression may be detected by various methods that are well known to those of ordinary skill in the art. For example, the level of Tregs may be measured by flow cytometry analysis of peripheral blood mononuclear cells or T lymphocytes, immunostained either for cellular surface markers or nuclear intracellular markers of Treg (Chen & Oppenheim, 2011), CD45, TCR-β, or CD4 markers of lymphocytes, and measuring the amount of antibody specifically bound to the cells. The functional activity of Tregs may be measured by various assays; For example the thymidine incorporation assay is being commonly used, in which suppression of anti-CD3 mAb stimulated proliferation of CD4$^+$CD25$^-$ T cells (conventional T cells) is measured by [$^3$H]thymidine incorporation or by using CFSE (5-(and 6)-carboxyfluorescein diacetate succinimidyl ester, which is capable of entering the cells; cell division is measured as successive halving of the fluorescence intensity of CFSE). The number of IFNγ-producing leukocytes or their activity or their proliferation capacity can easily be assessed by a skilled artisan using methods known in the art; For example, the level of IFNγ-producing leukocytes may be measured by flow cytometry analysis of peripheral blood mononuclear cells, following short ex-vivo stimulation and golgi-stop, and immunostaining by IFNγ intracellular staining (using e.g., BD Biosciences Cytofixl-cytoperm™ fixation/permeabilization kit), by collecting the condition media of these cells and quantifying the level of secreted cytokines using ELISA, or by comparing the ratio of different cytokines in the condition media, for example IL2/IL10, IL2/IL4, INFγ/TGFβ, etc. The levels of MDSCs in the human peripheral blood easily can be assessed by a skilled artisan, for example by using flow cytometry analysis of frequency of DR$^-$/LIN$^-$/CD11b+, DR$^-$/LIN$^-$/CD15+, DR$^-$/LIN$^-$/CD33+ and DR(−/low)/CD14+ cells, as described (Kotsakis et al, 2012).

In humans, the peripheral/systemic immunosuppression may be considered elevated when the total number of Tregs in the circulation is higher than 10, 20, 30, 40, 50, 60, 70, 80, 90, or 100% or more than in a healthy control population, the percentage of Treg cells out of the total CD4+ cells is elevated by 10, 20, 30, 40, 50, 60, 70, 80, 90, or 100% or more than in a healthy control population, or the functional activity of Tregs is elevated by 10, 20, 30, 40, 50, 60, 70, 80, 90, or 100% or more than in a healthy control population. Alternatively, the peripheral/systemic immunosuppression may be considered elevated when the level of IFNγ-producing leukocytes or their activity is reduced relative to that of a healthy control population by 10, 20, 30, 40, 50, 60, 70, 80, 90 or 100%; or the proliferation of leukocytes in response to stimulation is reduced relative to that of a healthy control population by 10, 20, 30, 40, 50, 60, 70, 80, 90 or 100%.

An agent may be considered an agent that causes reduction of the level of systemic immunosuppression when, upon administration of the agent to an individual, the total number of Tregs in the circulation of this individual is reduced by 10, 20, 30, 40, 50, 60, 70, 80, 90 or 100% as compared with the level before administration of the agent, the percentage of Treg cells out of the total CD4+ cells drops by 10, 20, 30, 40, 50, 60, 70, 80, 90 or 100% relative to that of a healthy control population or the functional activity of Tregs is reduced by 10, 20, 30, 40, 50, 60, 70, 80, 90 or 100% as compared with the level before administration of the agent. Alternatively, an agent may be considered an agent that causes reduction of the level of systemic immunosuppression when, upon administration of the agent to an individual, the total number of IFNγ-producing leukocytes or their activity is increased by 10, 20, 30, 40, 50, 60, 70, 80, 90, or 100% or more; or the proliferation of leukocytes in response to stimulation is increased relative to that of a healthy control population by 10, 20, 30, 40, 50, 60, 70, 80, 90 or 100% or more.

In certain embodiments, the active agent causes reduction of the level of systemic immunosuppression by release of a restraint imposed on the immune system by one or more immune checkpoints, for example by blockade of the one or more immune checkpoints.

In certain embodiments, the reduction of the level of systemic immunosuppression is associated with an increase in systemic presence or activity of IFNγ-producing leukocytes.

In certain embodiments, the active agent causes reduction of the level of systemic immunosuppression and thereby an increase in the systemic presence or activity of effector T cells.

In certain embodiments, the reduction of the level of systemic immunosuppression is associated with an increase in systemic presence or activity of an IFNγ cytokine.

In certain embodiments, the reduction of the level of systemic immunosuppression is associated with a decrease in systemic presence or activity of regulatory T-cells.

In certain embodiments, the reduction of the level of systemic immunosuppression is associated with a decrease in systemic presence or activity of an IL-10 cytokine.

In certain embodiments, the reduction of the level of systemic immunosuppression is associated with a decrease in systemic presence or activity of myeloid-derived suppressor cells (MDSCs).

In certain embodiments, the active agent causes reduction of the level of systemic immunosuppression and thereby an increase in the systemic presence or activity of effector T cells.

The checkpoints that may be manipulated to release the systemic immunosuppression are referred to herein as a pair of an immune checkpoint receptor and its native ligand or either one of the two partners. For example, PD-1, which has two known ligands is referred to herein as "PD-L1" and "PD-L2", while B7H3, the ligand of which has not yet been identified, is referred to simply by "B7H3". The checkpoints that may be manipulated to release the systemic immunosuppression in accordance with the present invention include, without limitation, PD-1-PD-L1, PD-1-PD-L2, CD28-CD80, CD28-CD86, CTLA-4-CD80, CTLA-4-CD86, ICOS-B7RP1, B7H3, B7H4, B7H7, B7-CD28-like molecule, BTLA-HVEM, KIR-MHC class I or II, LAG3-MHC class I or II, CD137-CD137L, OX40-OX40L, CD27-CD70, CD40L-CD40, TIM3-GAL9, V-domain Ig suppressor of T cell activation (VISTA), STimulator of INterferon Genes (STING), T cell immunoglobulin and immunoreceptor tyrosine-based inhibitory motif domain (TIGIT), glucocorticoid-induced tumor necrosis factor receptor related protein (GITR), A2aR-Adenosine and indoleamine-2,3-dioxygenase (IDO)-L-tryptophan.

Agents capable of blocking immune checkpoints are known in the art (Colombo & Piconese, 2007) and these agents can be used in accordance with the present invention. Each one of the cited publications below, and Pardoll, 2012, is incorporated by reference as if fully disclosed herein.

In certain embodiments, the active agent that may be used according to the present invention may be an antibody. An antibody as disclosed herein can be a polyclonal antibody, a monoclonal antibody, a dimer, a multimer, a multispecific antibody, a human antibody, a humanized antibody, a recombinant antibody, a chimeric antibody, bi-functional antibody, a cell-associated antibody like an Ig receptor, a linear antibody, a diabody, a minibody or a nanobody, so long as the fragment exhibits the desired biological activity, and single chain derivatives of the same. An antibody can be a full-length immunoglobulin molecule comprising the VH and VL domains, as well as a light chain constant domain (CL) and heavy chain constant domains, CH1, CH2 and CH3, or an immunologically active fragment of a full-length immunoglobulin molecule, such as, e.g., a single domain antibody (sdAb), a single-chain variable fragment (scFv), a Fab fragment, a F(ab')2 fragment, a Fc fragment, a Fd fragment, a Fv fragment. An antibody can be derived from any vertebrate species (e.g., human, goat, horse, donkey, murine, rat, rabbit, or chicken), and can be of any type (e.g., IgG, IgE, IgM, IgD, and IgA), class (e.g., IgA, IgD, IgE, IgG, and IgM) or subclass (IgG1, IgG2, IgG3, IgG4, IgA1 and IgA2). Functionally, an antibody disclosed herein may be an antagonist antibody, meaning an antibody that inhibits a biological activity or an antibody disclosed herein may be an agonist antibody, meaning an antibody that stimulates a biological activity. Similarly, an antibody disclosed herein may be a neutralizing antibody, meaning an antibody that can block or neutralize a biological activity. For general disclosure on the structure of naturally occurring antibodies, non-naturally occurring antibodies, and antigenic compound-binding fragments thereof, see, e.g., Pluckthun in The Pharmacology of Monoclonal Antibodies, vol. 113, Rosenburg and Moore eds., Springer-Verlag, New York, pp. 269-315 (1994); Borrabeck, Antibody Engineering, 2d ed. (Oxford University Press 1995), each of which is hereby incorporated by reference in its entirety.

An antibody disclosed herein may be, without limitation, an anti-PD-1, an anti-PD-L1, an anti-PD-L2, an anti-CTLA-4, an anti-CD80, an anti-CD86, an anti-B7RP1, an anti-B7-H3, an anti-B7-H4, an anti-B7-H7, an anti-BTLA, an anti-HVEM, an anti-CD-27, an anti-CD40, an anti-CD40L, an anti-CD70, an anti-CD80, an anti-CD86, an anti-CD137, an anti-CD137L, an anti-OX40, an anti-OX40L, an anti-TIM-3, an anti-Galectin9, an anti-KIR, an anti-LAG-3, an anti-ICOS, an anti-VISTA, an anti-STING, an anti-TIGIT, anti-GITR or any combination thereof. An antibody disclosed herein may be administered to a human at a dosage of for example about 0.1 mg/kg-20 mg/kg, 0.1 mg/kg-15 mg/kg, 0.1 mg/kg-10 mg/kg, 0.1 mg/kg-5 mg/kg, 0.2 mg/kg-20 mg/kg, 0.2 mg/kg-15 mg/kg, 0.2 mg/kg-10 mg/kg, 0.2 mg/kg-6 mg/kg, 0.2 mg/kg-5 mg/kg, 0.3 mg/kg-20 mg/kg, 0.3 mg/kg-15 mg/kg, 0.3 mg/kg-10 mg/kg, 0.3 mg/kg-5 mg/kg-1 mg/kg-20 mg/kg, 1 mg/kg-15 mg/kg, 1 mg/kg-10 mg/kg, 1 mg/kg-5 mg/kg, 1.5 mg/kg-20 mg/kg, 1.5 mg/kg-15 mg/kg, 1.5 mg/kg-10 mg/kg, 1.5 mg/kg-6 mg/kg or 1.5 mg/kg-5 mg/kg.

Programmed cell death protein 1, also known as PD-1 and CD279 (cluster of differentiation 279), is a cell surface receptor that belongs to the immunoglobulin superfamily and is expressed on T cells and pro-B cells. PD-1 binds two ligands, PD-L1 and PD-L2. Functioning as an immune checkpoint, PD-1 plays an important role in down regulating the immune system by preventing the activation of T-cells, which in turn reduces autoimmunity and promotes self-tolerance. The inhibitory effect of PD-1 is accomplished through a dual mechanism of promoting apoptosis (programmed cell death) in antigen specific T-cells in lymph nodes while simultaneously reducing apoptosis in regulatory T cells (suppressor T cells). As such, compounds which inhibit PD-1 function, such as PD-1 inhibitors, PD-L1 inhibitors and/or PD-L2 inhibitors, serve to activate the immune system. One class of PD-1 inhibitors includes antagonist or neutralizing anti-PD-1, anti-PD-L1 and anti-PD-L2 antibodies. Many antagonist or neutralizing anti-PD-1, anti-PD-L1 and anti-PD-L2 antibodies are known in the art. For example, the anti-PD-1 antibody used in accordance with the present invention may be selected from those disclosed in Ohaegbulam et al. (Ohaegbulam et al, 2015), the entire contents of which being hereby incorporated herein by reference. Examples of human or humanized anti-PD-1 antibodies include, without limitation, CD279 (human anti-PD1 monoclonal antibody, Bio X Cell), MEDI0680 (AMP-514; humanized IgG4 anti-PD-1 monoclonal antibody; AstraZeneca), Nivolumab (BMS-936558; human IgG4 anti-PD1 monoclonal antibody; Bristol-Myers Squibb), Pembrolizumab (Lambrolizumab, MK-3475; humanized IgG4 anti-PD1 monoclonal antibody; Merck), Pidilizumab (CT-011; humanized IgG1 anti-PD1 monoclonal antibody; Medivation) and TSR-042 (humanized IgG4 anti-PD-1 monoclonal antibody; Tesaro). Examples of human or humanized anti-PD-L1 antibodies include, without limitation, Avelumab (MSB0010718C; human IgG1 anti-PD-L1 monoclonal antibody; Merck-Serono), Atezolizumab (MPDL3280A, RG7446; human IgG anti-PD-L1 monoclonal antibody; Hoffmann-La Roche), BMS-936559 (MDX-1105; human IgG4 anti-PD-L1 monoclonal antibody; Bristol-Myers Squibb), Durvalumab (MEDI4736; humanized IgG1 anti-PD-L1 monoclonal antibody; AstraZeneca), KN035 (anti-PD-L1 monoclonal antibody; 3D Medicines) and LY3300054 (anti-PD-L1 monoclonal antibody; Eli Lilly). Examples of human or humanized anti-PD-L2 antibodies include, without limitation, AMP-224 (IgG2a Fc fusion protein of PD-L2; AstraZeneca). In certain embodiments, an anti-PD-1 antibody, an anti-PD-L1 antibody and/or an anti-PD-L2 antibody may be administered to a human at a dosage of for example about 0.1 mg/kg-20 mg/kg, 0.1 mg/kg-15 mg/kg, 0.1 mg/kg-10 mg/kg, 0.1 mg/kg-5 mg/kg, 0.2 mg/kg-20 mg/kg, 0.2 mg/kg-15 mg/kg, 0.2 mg/kg-10 mg/kg, 0.2 mg/kg-6 mg/kg, 0.2 mg/kg-5 mg/kg, 0.3 mg/kg-20 mg/kg, 0.3 mg/kg-15 mg/kg, 0.3 mg/kg-10 mg/kg, 0.3 mg/kg-5 mg/kg-1 mg/kg-20 mg/kg, 1 mg/kg-15 mg/kg, 1 mg/kg-10 mg/kg, 1 mg/kg-5 mg/kg, 1.5 mg/kg-20 mg/kg, 1.5 mg/kg-15 mg/kg, 1.5 mg/kg-10 mg/kg, 1.5 mg/kg-6 mg/kg or 1.5 mg/kg-5 mg/kg.

In certain embodiments, Pidilizumab may be administered to a human at a dosage of 0.2-6 mg/kg or between 1.5-6 mg/kg; Pembrolizumab may be administered to a human at a dosage of 1-10 mg/kg; Nivolumab may be administered to a human at a dosage of 0.3-20 mg/kg, 0.3-10 mg/kg, 1-10 mg/kg or at 1 or 3 mg/kg; BMS-936559 may be administered to a human at a dosage of 0.3-10 mg/kg; Atezolizumab may be administered to a human at a dosage of 1-20 mg/kg; Durvalumab may be administered to a human at a dosage of 0.1-15 mg/kg; and Avelumab may be administered to a human at a dosage of 1-20 mg/kg.

T-cell immunoglobulin and mucin domain-3 (TIM-3) is a Th1-specific cell surface protein that acts as an immune checkpoint that inhibits lymphocyte activity by down regulating macrophage activation and playing an important role in CD8+ T cell exhaustion that takes place in chronic immune conditions. TIM-3 acts as a negative regulator of Th1/Tc1 function by triggering cell death upon interaction with its ligand, galectin-9 (Gal9). As such, compounds which inhibit TIM-3 function, such as TIM-3 inhibitors and/or Gal9 inhibitors, serve to activate the immune system. One class of TIM-3 inhibitors includes antagonist or neutralizing antibodies against TIM-3 and/or Gal-9. Many antagonist or neutralizing anti-TIM-3 and anti-Gal9 antibodies are known in the art. Examples of human or humanized anti-TIM-3 antibodies include, without limitation, AF2365 (human IgG anti-TIM-3 monoclonal antibody; R&D Systems), CD366 (human IgG1 anti-TIM-3 monoclonal antibody; BioLegend), F38-2E2 (human IgG1 anti-TIM-3 monoclonal antibody; R&D Systems), L3D (human IgG1 anti-TIM-3 monoclonal antibody; CN 102492038 B), MAB2365 (human IgG2a anti-TIM-3 monoclonal antibody; R&D Systems), MAB23651 (human IgG1 anti-TIM-3 monoclonal antibody; R&D Systems) and TSR-022 (humanized IgG4 anti-TIM-3 monoclonal antibody; Tesaro). In certain embodiments, an anti-TIM-3 antibody and/or an anti-Gal9 antibody may be administered to a human at a dosage of for example about 0.1 mg/kg-20 mg/kg, 0.1 mg/kg-15 mg/kg, 0.1 mg/kg-10 mg/kg, 0.1 mg/kg-5 mg/kg, 0.2 mg/kg-20 mg/kg, 0.2 mg/kg-15 mg/kg, 0.2 mg/kg-10 mg/kg, 0.2 mg/kg-6 mg/kg, 0.2 mg/kg-5 mg/kg, 0.3 mg/kg-20 mg/kg, 0.3 mg/kg-15 mg/kg, 0.3 mg/kg-10 mg/kg, 0.3 mg/kg-5 mg/kg-1 mg/kg-20 mg/kg, 1 mg/kg-15 mg/kg, 1 mg/kg-10 mg/kg, 1 mg/kg-5 mg/kg, 1.5 mg/kg-20 mg/kg, 1.5 mg/kg-15 mg/kg, 1.5 mg/kg-10 mg/kg, 1.5 mg/kg-6 mg/kg or 1.5 mg/kg-5 mg/kg.

Cytotoxic T-lymphocyte-associated protein 4 (CTLA-4), also known as cluster of differentiation 152 (CD152), is a protein receptor functioning as an immune checkpoint that downregulates immune responses. CTLA-4 is constitutively expressed in Tregs but only upregulated in conventional T cells after activation. CTLA-4 acts as an "off" switch when bound to CD80 or CD86 on the surface of antigen-presenting cells. As such, compounds which inhibit CTLA-4 function, such as CTLA-4 inhibitors, CD80 inhibitors and/or CD86 inhibitors, serve to activate the immune system. One class of CTLA-4 inhibitors includes antagonist or neutralizing antibodies against CTLA-4, CD80 and/or CD86. Many antagonist or neutralizing anti-CTLA-4, anti-CD80 and anti-CD86 antibodies are known in the art. Examples of human or humanized anti-CTLA-4 antibodies include, without limitation, Ipilimumab (human IgG1 anti-CTLA-4 monoclonal antibody; Bristol-Myers Squibb) and Tremelimumab (human IgG2 anti-CTLA-4 monoclonal antibody; Pfizer). In certain embodiments, an anti-CTLA-4 antibody, an anti-CB80 antibody and/or an anti-CD86 antibody may be administered to a human at a dosage of for example about 0.1 mg/kg-20 mg/kg, 0.1 mg/kg-15 mg/kg, 0.1 mg/kg-10 mg/kg, 0.1 mg/kg-5 mg/kg, 0.2 mg/kg-20 mg/kg, 0.2 mg/kg-15 mg/kg, 0.2 mg/kg-10 mg/kg, 0.2 mg/kg-6 mg/kg, 0.2 mg/kg-5 mg/kg, 0.3 mg/kg-20 mg/kg, 0.3 mg/kg-15 mg/kg, 0.3 mg/kg-10 mg/kg, 0.3 mg/kg-5 mg/kg-1 mg/kg-20 mg/kg, 1 mg/kg-15 mg/kg, 1 mg/kg-10 mg/kg, 1 mg/kg-5 mg/kg, 1.5 mg/kg-20 mg/kg, 1.5 mg/kg-15 mg/kg, 1.5 mg/kg-10 mg/kg, 1.5 mg/kg-6 mg/kg or 1.5 mg/kg-5 mg/kg.

Killer-cell immunoglobulin-like receptors (KIRs) are a family of type 1 transmembrane glycoproteins expressed on the plasma membrane of natural killer (NK) cells and a minority of T cells. They regulate the killing function of these cells by interacting with major histocompatibility (MHC) class I molecules, which are expressed on all nucleated cell types. Thus, KIRs are inhibitors of lymphocyte activity. As such, compounds which inhibit KIR function, such as KIR inhibitors, serve to activate the immune system. One class of KIR inhibitors includes antagonist or neutralizing antibodies against KIR. Many antagonist or neutralizing anti-KIR antibodies are known in the art. Examples of human or humanized anti-KIR antibodies include, without limitation, Lirilumab (BMS-986015; human anti-KIR monoclonal antibody; Bristol-Myers Squibb). In certain embodiments, an anti-KIR antibody may be administered to a human at a dosage of for example about 0.1 mg/kg-20 mg/kg, 0.1 mg/kg-15 mg/kg, 0.1 mg/kg-10 mg/kg, 0.1 mg/kg-5 mg/kg, 0.2 mg/kg-20 mg/kg, 0.2 mg/kg-15 mg/kg, 0.2 mg/kg-10 mg/kg, 0.2 mg/kg-6 mg/kg, 0.2 mg/kg-5 mg/kg, 0.3 mg/kg-20 mg/kg, 0.3 mg/kg-15 mg/kg, 0.3 mg/kg-10 mg/kg, 0.3 mg/kg-5 mg/kg-1 mg/kg-20 mg/kg, 1 mg/kg-15 mg/kg, 1 mg/kg-10 mg/kg, 1 mg/kg-5 mg/kg, 1.5 mg/kg-20 mg/kg, 1.5 mg/kg-15 mg/kg, 1.5 mg/kg-10 mg/kg, 1.5 mg/kg-6 mg/kg or 1.5 mg/kg-5 mg/kg.

Lymphocyte-activation gene 3 (LAG-3), also known as cluster of differentiation 223 (CD223), is a cell surface molecule with diverse biologic effects on T cell function. LAG-3 is an immune checkpoint that inhibits lymphocyte activity by suppressing an immune response by action to Tregs as well as direct effects on CD8+ T cells. As such, compounds which inhibit LAG-3 function, such as LAG-3 inhibitors, serve to activate the immune system. One class of LAG-3 inhibitors includes antagonist or neutralizing antibodies against LAG-3. Many antagonist or neutralizing anti-LAG-3 antibodies are known in the art. Examples of human or humanized anti-LAG-3 antibodies include, without limitation, BMS-986016 (human anti-LAG-3 monoclonal antibody; Bristol-Myers Squibb). In certain embodiments, an anti-LAG-3 antibody may be administered to a human at a dosage of for example about 0.1 mg/kg-20 mg/kg, 0.1 mg/kg-15 mg/kg, 0.1 mg/kg-10 mg/kg, 0.1 mg/kg-5 mg/kg, 0.2 mg/kg-20 mg/kg, 0.2 mg/kg-15 mg/kg, 0.2 mg/kg-10 mg/kg, 0.2 mg/kg-6 mg/kg, 0.2 mg/kg-5 mg/kg, 0.3 mg/kg-20 mg/kg, 0.3 mg/kg-15 mg/kg, 0.3 mg/kg-10 mg/kg, 0.3 mg/kg-5 mg/kg-1 mg/kg-20 mg/kg, 1 mg/kg-15 mg/kg, 1 mg/kg-10 mg/kg, 1 mg/kg-5 mg/kg, 1.5 mg/kg-20 mg/kg, 1.5 mg/kg-15 mg/kg, 1.5 mg/kg-10 mg/kg, 1.5 mg/kg-6 mg/kg or 1.5 mg/kg-5 mg/kg.

OX40, also known as cluster of differentiation 134 (CD134), is a member of the TNFR-superfamily of receptors. OX40 promotes the expansion of effector and memory T cells, however it is also noted for its ability to suppress the differentiation and activity of T-regulatory cells, and also for its regulation of cytokine production. Being transiently expressed after T-cell receptor engagement, OX40 is only upregulated on the most recently antigen-activated T cells within inflammatory lesions. Its ligand is OX40L, also known as cluster of differentiation 252 (CD252). As such, compounds which activate or stimulate OX40 function, such as OX40 activators and/or OX40L activators, serve to activate the immune system. One class of OX40 activators includes agonist antibodies against OX40 and OX40L. Many agonist antibodies against OX40 and/or OX40L are known in the art. Examples of human or humanized anti-OX40 antibodies include, without limitation, GSK3174998; humanized IgG1 anti-OX40 monoclonal antibody; GlaxoSmithKline), MEDI0562 (humanized anti-OX40 monoclonal antibody; MedImmune) and MEDI6383 (human OX40 fusion protein; MedImmune). Other anti-OX40 antibodies include, without limitation, MEDI6469 (9B12; murine anti-OX40 monoclonal antibody; MedImmune). In certain embodiments, an anti-OX40 antibody and/or an anti-OX40L antibody may be administered to a human at a dosage of for example about 0.1 mg/kg-20 mg/kg, 0.1 mg/kg-15 mg/kg, 0.1 mg/kg-10 mg/kg, 0.1 mg/kg-5 mg/kg, 0.2 mg/kg-20 mg/kg, 0.2 mg/kg-15 mg/kg, 0.2 mg/kg-10 mg/kg, 0.2 mg/kg-6 mg/kg, 0.2 mg/kg-5 mg/kg, 0.3 mg/kg-20 mg/kg, 0.3 mg/kg-15 mg/kg, 0.3 mg/kg-10 mg/kg, 0.3 mg/kg-5 mg/kg-1 mg/kg-20 mg/kg, 1 mg/kg-15 mg/kg, 1 mg/kg-10 mg/kg, 1 mg/kg-5 mg/kg, 1.5 mg/kg-20 mg/kg, 1.5 mg/kg-15 mg/kg, 1.5 mg/kg-10 mg/kg, 1.5 mg/kg-6 mg/kg or 1.5 mg/kg-5 mg/kg.

Anti-GITR antibodies target glucocorticoid-induced tumor necrosis factor receptor related protein (GITR), which is regularly expressed on the surface of regulatory T-cells (Tregs) and is expressed on the surface of effector T-cells after their activation. Anti-GITR antibodies block the interaction of GITR, found on multiple types of T cells, with its ligand, thereby inducing both the activation of tumor-antigen-specific T effector cells, as well as abrogating the suppression induced by inappropriately activated T regulatory cells. As such, compounds which activate or stimulate GITR function, such as GITR activators, serve to activate the immune system. One class of GITR activators includes agonist antibodies against GITR. Many agonist antibodies against GITR are known in the art. Examples of human or humanized anti-TIGR antibodies include, without limitation, GWN323 (humanized anti-GITR monoclonal antibody; Novartis) and TRX518 (humanized anti-GITR monoclonal antibody; GITR, Inc.). In certain embodiments, an anti-GITR antibody may be administered to a human at a dosage of for example about 0.1 mg/kg-20 mg/kg, 0.1 mg/kg-15 mg/kg, 0.1 mg/kg-10 mg/kg, 0.1 mg/kg-5 mg/kg, 0.2 mg/kg-20 mg/kg, 0.2 mg/kg-15 mg/kg, 0.2 mg/kg-10 mg/kg, 0.2 mg/kg-6 mg/kg, 0.2 mg/kg-5 mg/kg, 0.3 mg/kg-20 mg/kg, 0.3 mg/kg-15 mg/kg, 0.3 mg/kg-10 mg/kg, 0.3 mg/kg-5 mg/kg-1 mg/kg-20 mg/kg, 1 mg/kg-15 mg/kg, 1 mg/kg-10 mg/kg, 1 mg/kg-5 mg/kg, 1.5 mg/kg-20 mg/kg, 1.5 mg/kg-15 mg/kg, 1.5 mg/kg-10 mg/kg, 1.5 mg/kg-6 mg/kg or 1.5 mg/kg-5 mg/kg.

CD27 is a member of the tumor necrosis factor receptor superfamily. CD27 activity is governed by the transient availability of its ligand, CD70, on lymphocytes and dendritic cells. Activation of CD27 plays a key role in regulating B-cell activation and immunoglobulin synthesis, supports antigen-specific expansion of naïve T cells, is required for generation and long-term maintenance of T cell immunity and is a memory marker of B cells. CD27 transduces signals that lead to the activation of NF-κB and MAPK8/JNK. As such, compounds which activate or stimulate CD27 function, such as CD27 activators and/or CD70 activators, serve to activate the immune system. One class of CD27 activators includes agonist antibodies against CD27 and/or CD70. Many agonist antibodies against CD27 and/or CD70 are known in the art. Examples of human or humanized anti-CD27 antibodies include, without limitation, Varlilumab (CDX-1127; human anti-CD27 monoclonal antibody; Cell-dex Therapeutics). In certain embodiments, an anti-CD27 antibody and/or an anti-CD70 antibody may be administered to a human at a dosage of for example about 0.1 mg/kg-20 mg/kg, 0.1 mg/kg-15 mg/kg, 0.1 mg/kg-10 mg/kg, 0.1 mg/kg-5 mg/kg, 0.2 mg/kg-20 mg/kg, 0.2 mg/kg-15 mg/kg, 0.2 mg/kg-10 mg/kg, 0.2 mg/kg-6 mg/kg, 0.2 mg/kg-5 mg/kg, 0.3 mg/kg-20 mg/kg, 0.3 mg/kg-15 mg/kg, 0.3 mg/kg-10 mg/kg, 0.3 mg/kg-5 mg/kg-1 mg/kg-20 mg/kg, 1 mg/kg-15 mg/kg, 1 mg/kg-10 mg/kg, 1 mg/kg-5 mg/kg, 1.5 mg/kg-20 mg/kg, 1.5 mg/kg-15 mg/kg, 1.5 mg/kg-10 mg/kg, 1.5 mg/kg-6 mg/kg or 1.5 mg/kg-5 mg/kg.

Inducible T-cell COStimulator (ICOS), also known as cluster of differentiation 278 (CD278), is a CD28-superfamily costimulatory cell-surface receptor that is expressed on activated T cells. It is an activator of T cell function. As such, compounds which activate or stimulate ICOS function, such as ICOS activators or B7RP1 activators, serve to activate the immune system. One class of ICOS activators includes agonist antibodies against ICOS and/or B7RP1. Many agonist anti-ICOS and anti-B7RP1 antibodies are known in the art. In certain embodiments, an anti-ICOS antibody and/or an anti-B7RP1 antibody may be administered to a human at a dosage of for example about 0.1 mg/kg-20 mg/kg, 0.1 mg/kg-15 mg/kg, 0.1 mg/kg-10 mg/kg, 0.1 mg/kg-5 mg/kg, 0.2 mg/kg-20 mg/kg, 0.2 mg/kg-15 mg/kg, 0.2 mg/kg-10 mg/kg, 0.2 mg/kg-6 mg/kg, 0.2 mg/kg-5 mg/kg, 0.3 mg/kg-20 mg/kg, 0.3 mg/kg-15 mg/kg, 0.3 mg/kg-10 mg/kg, 0.3 mg/kg-5 mg/kg-1 mg/kg-20 mg/kg, 1 mg/kg-15 mg/kg, 1 mg/kg-10 mg/kg, 1 mg/kg-5 mg/kg, 1.5 mg/kg-20 mg/kg, 1.5 mg/kg-15 mg/kg, 1.5 mg/kg-10 mg/kg, 1.5 mg/kg-6 mg/kg or 1.5 mg/kg-5 mg/kg.

In certain embodiments, combinations of antibodies may be used such as but not limited to: CT-011 in combination with Rituximab (trade names Rituxan, MabThera and Zytux) a chimeric monoclonal antibody against the protein CD20, for example, each at 3 mg/kg; Nivolumab (for example 1 mg/kg) in combination with Ipilimumab; for example at 3 mg/kg); or Nivolumab (e.g. 1-10 mg/kg) in combination with a an HLA-A*0201-restricted multipeptide vaccine (Weber et al, 2013).

In certain embodiments, the active agent that may be used according to the present invention may be an antibody mimetic. Antibody mimetics can specifically bind antigens like antibodies, but that are not structurally related to antibodies. They are usually artificial peptides or proteins with a molar mass of about 3 kDa to 20 kDa. In aspects of this embodiment, an antibody mimetic disclosed herein may be an affibody molecule; an affilin; an affimer; an affitin; an alphabody; an anticalin; an avimer; a DARPin; a fynomer; a Kunitz domain peptide; or a monobody. Non-limiting examples of antibody mimetics are presented in Table 1.

TABLE 1

| Antibody mimetics | | | |
|---|---|---|---|
| Antibody mimetic | Scaffold | Molar mass | Example drug |
| Affibodies[1] | Z domain of Protein A | 6 kDa | ABY-025 |
| Affilins[2] | Gamma-B crystallin | 20 Da | |
| | Ubiquitin | 10 Da | SPVF 2801 |
| Affimers[3] | Cystatin | 12-14 kDa | |
| Affitins[4] | Sac7d (from Sulfolobus acidocaldarius) | 7 kDa | |
| Alphabodies[5] | Triple helix coiled coil | 10 Da | CMPX-1023 |
| Anticalins[6] | Lipocalins | 20 Da | |

TABLE 1-continued

Antibody mimetics

| Antibody mimetic | Scaffold | Molar mass | Example drug |
|---|---|---|---|
| Avimers[7] | A domains of various membrane receptors | 9-18 kDa | |
| DARPins[8] | Ankyrin repeat motif | 10-19 kDa | MP0112 |
| Fynomers[9] | SH3 domain of Fyn | 7 kDa | |
| Kunitz domain peptides[10] | Kunitz domains of various protease inhibitors | 6 kDa | Ecallantide (Kalbitor) |
| Monobodies[11] | 10$^{th}$ type III domain of fibronectin | 10 kDa | Pegdinetanib (Angiocept) |

[1]Nygren PA (June 2008);
[2]Ebersbach et al. (2007);
[3]Johnson et al. (2012);
[4]Krehenbrink et al. (2008);
[5]Desmet et al. (2014);
[6]Skerra A (2008);
[7]Silverman et al. (2005);
[8]Stumpp et al. (2008)'
[9]Grabulovski et al. (2007);
[10]Nixon et al. (2006);
[11]Koide et al. (2007).

In certain embodiments, the active agent that may be used according to the present invention may be an aptamer. Aptamers are oligonucleotide or peptide molecules that bind to a specific target molecule. In aspects of this embodiment, an aptamer disclosed herein may be a DNA aptamer, a RNA aptamer, a XNA aptamer or a peptide aptamer.

In certain embodiments, an antibody disclosed herein may be in combination with an adjuvant. An adjuvant is any substance or mixture of substances that increases or diversifies the immune response. An adjuvant may serve to reduce the number of immunizations or the amount of antigen required for protective immunization. Non-limiting adjuvants include, e.g., liposomes, oily phases, including, without limitation, the Freund type of adjuvants, such as, e.g., Freund's complete adjuvant (FCA); Freund's incomplete adjuvant (FIA); sapogenin glycosides, such as, e.g., saponins; carbopol; N-acetylmuramyl-L-alanyl-D-isoglutamine (commonly known as muramyl dipeptide or "MDP"); and lipopolysaccharide (LPS). Such adjuvants are generally used in the form of an emulsion with an aqueous phase, or, more commonly, with water-insoluble inorganic salts. These inorganic salts include aluminum hydroxide, zinc sulfate, colloidal iron hydroxide, calcium phosphate or calcium chloride. In aspects of this embodiment, an antibody disclosed herein may be combined with, e.g., an anti-CTLA-4 antibody in combination with an anti-OX40 antibody and a TLR9 ligand such as CpG (Marabelle et al, 2013).

In certain embodiments, the active agent that may be used according to the present invention may be a small molecule. In aspects of this embodiment, a small molecule disclosed herein may be: (a) a p300 inhibitor (Liu et al, 2013), such as gemcitabine (low dose) or C646 or analogs thereof, i.e. a compound of the formula I:

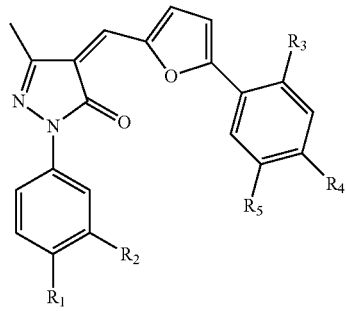

wherein $R_1$ is selected from H, —$CO_2R_6$, —$CONR_6R_7$, —$SO_3H$, or —$SO_2NR_6R_7$; $R_2$ is selected from H, —$CO_2R_6$, or halogen, preferably Cl; $R_3$ is selected from halogen, preferably F, —$NO_2$, —CN, —$CO_2R_6$, preferably $CO_2CH_3$ or $CO_2CH_2CH_3$, or —$CH_2OH$; $R_4$ and $R_5$ each independently is H or —$C_1$-$C_6$ alkyl, preferably methyl; $R_6$ is H or —$C_1$-$C_6$ alkyl, preferably H, methyl or ethyl; and $R_7$ is H or —$C_1$-$C_6$ alkyl, preferably H or methyl; (b) a Sunitinib; (c) a Polyoxometalate-1 (POM-1) (Ghiringhelli et al, 2012); (d) an α,β-methyleneadenosine 5'-diphosphate (APCP); (e) an arsenic trioxide ($As_2O_3$); (f) a GX15-070 (Obatoclax); (g) a retinoic acid antagonist such as Ro 41-5253 (a synthetic retinoid and selective small molecule antagonist) or LE-135; (h) an SIRPα (CD47) antagonist, such as CV1-hIgG4 (SIRPα variant) as sole agent or in combination with anti-CD47 antibody; (i) a CCR4 antagonist, such as AF399/420/18025 as sole agent or in combination with anti-CCR4 antibody; (j) an adenosine receptor antagonist; (k) an adenosine A1 receptor antagonist; an adenosine A2a receptor; (m) an adenosine A2b receptor antagonist; (n) an A3 receptor antagonist; (o) an antagonist of indoleamine-2,3-dioxygenase; or (p) an HIF-1 regulator.

In certain embodiments, the agent is a p300 inhibitor, which formulas are listed in Table 2, i.e. C646 (4-(4-((5-(4,5-dimethyl-2-nitrophenyl)furan-2-yl)methylene)-3-methyl-5-oxo-4,5-dihydro-1H-pyrazol-1-yl)benzoic acid), C146 (4-hydroxy-3-(((2-(3-iodophenyl)benzo[d]oxazol-5-yl)imino)methyl)benzoic acid) or C375 (2-chloro-4-(5-((2,4-dioxo-3-(2-oxo-2-(p-tolylamino)ethyl)thiazolidin-5-ylidene)methyl)furan-2-yl)benzoic acid). In particular, the p300 inhibitor is C646.

TABLE 2*

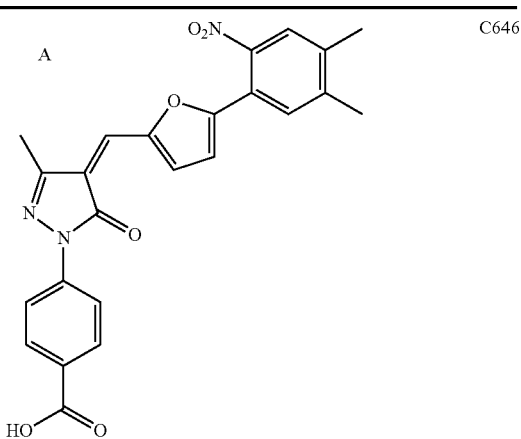

TABLE 2*-continued

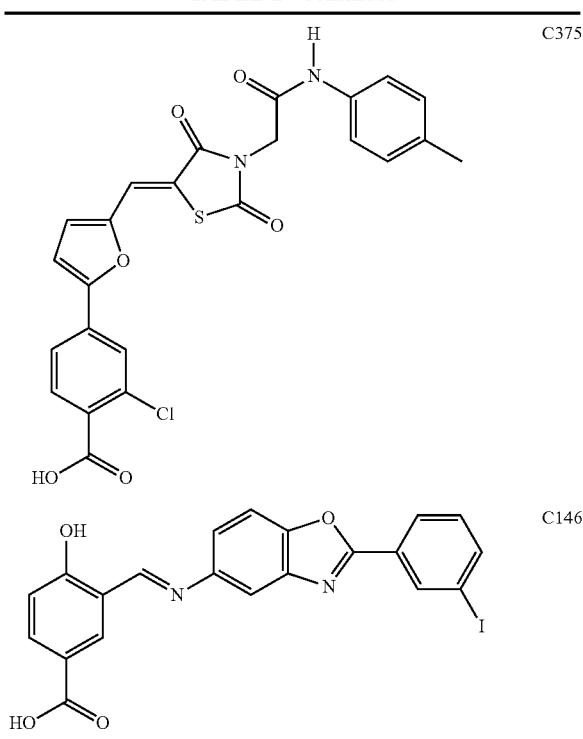

*Based on Bowers et al. (2010)

In certain embodiments, the adenosine receptor antagonist may be CGS15943 (9-Chloro-2-(2-furanyl)-[1,2,4]triazolo[1,5-c]quinazolin-5-amine); the adenosine A1 receptor antagonist may be PSB 36 (1-Butyl-8-(hexahydro-2,5-methanopentalen-3a(1H)-yl)-3,7-dihydro-3-(3-ydroxypropyl)-1H-purine-2,6-dione); the adenosine A2a receptor antagonist may be SCH58261 (5-Amino-7-(2-phenylethyl)-2-(2-furyl)-pyrazolo(4,3-e)-1,2,4-triazolo(1,5-c)pyrimidine), SYN115 (4-Hydroxy-N-[4-methoxy-7-(4-morpholinyl)-2-benzothiazolyl]-4-methyl-1-piperidinecarboxamide), FSPTP (also called SCH58261 (5-amino-7-[2-(4-fluorosulfonyl)phenylethyl]-2-(2-furyl)-pryazolo[4,3-ε]-1,2,4-triazolo[1,5-c]pyrimidine), SCH442416 (2-(2-Furanyl)-7-[3-(4-methoxyphenyl)propyl]-7H-pyrazolo[4,3-e][1,2,4]triazolo[1,5-c]pyrimidin-5-amine), or ZM241385 (also called tozadenant (4-Hydroxy-N-(4-methoxy-7-morpholinobenzo[d]thiazol-2-yl)-4-methylpiperidine-1-carboxamide); the adenosine A2b receptor antagonist may be PSB 603 (8-{4-[4-(4-chlorophenyl)piperazine-1-sulfonyl]phenyl}-1-propyl-2,3,6,7-tetrahydro-1H-purine-2,6-dione (Nakatsukasa et al, 2011)); and the A3 receptor antagonist may be MRS3777 (2-Phenoxy-6-(cyclohexylamino)purine hemioxalate).

In certain embodiments, the small molecule inhibitor of the indoleamine-2,3-dioxygenase pathway may be Indoximod (NSC-721782/NLG-9189 (1-Methyl-D-tryptophan), NewLink Genetics), INCB024360 ((4E)-4-[(3-chloro-4-fluoroanilino)-nitrosomethylidene]-1,2,5-oxadiazol-3-amine, Incyte) or NLG-919 (1-Cyclohexyl-2-(5H-imidazo[5,1-a]isoindol-5-yl)ethanol), NewLink Genetics).

The HIF-1 regulator may be M30, (5-[N-methyl-N-propargylaminomethyl]-8-hydroxyquinoline) described in Zheng et al. (Zheng et al, 2015).

In certain embodiments, an active agent that may be used according to the present invention may be any combination of an antibody disclosed herein and a small molecule disclosed herein. In aspects of this embodiment, an active agent may be any combination of antibody disclosed herein and small molecule disclosed herein.

In certain embodiments, an active agent that may be used according to the present invention may be a protein selected from the group consisting of: (a) Neem leaf glycoprotein (NLGP; (Roy et al, 2013)); and/or (b) 5CTLA-4 (soluble isoform of CTLA-4) (Ward et al, 2013).

In certain embodiments, an active agent that may be used according to the present invention may be a silencing molecule. In aspects of this embodiment, a silencing molecule is selected from the group consisting of miR-126 antisense (Qin et al, 2013) and anti-galectin-1 (Gal-1; (Dalotto-Moreno et al, 2013)).

In certain embodiments, an active agent that may be used according to the present invention may be an OK-432 (lyophilized preparation of *Streptococcus pyogenes*) (Hirayama et al, 2013).

In certain embodiments, an active agent that may be used according to the present invention may be a combination of IL-12 and anti-CTLA-4.

In certain embodiments, the agent can be derived from a broad spectrum of antibiotics which targets gram-positive and gram-negative bacteria, and thereby facilitating immunomodulation of Tregs, e.g. vancomycin which targets gram-positive bacteria and has been shown to reduce Treg levels/activity (Brestoff & Artis, 2013; Smith et al, 2013).

In certain embodiments, an active agent that may be used according to the present invention may be any combination of an antibody disclosed herein, an antibody mimetic disclosed herein, an aptamer disclosed herein, a small molecule disclosed herein, a Neem leaf glycoprotein disclosed herein, a sCTLA-4 disclosed herein, a silencing molecule disclosed herein, an OK-432 disclosed herein, and/or a combination of IL-12 and anti-CTLA-4 disclosed herein.

As stated above, the active agent is administered by a dosage regime comprising at least two courses of therapy, each course of therapy comprising in sequence a treatment session followed by an interval session of non-treatment.

The term "treatment session" is used interchangeably herein with the terms "treatment period" or "period of treatment" and refers to a session during which one or more active agents disclosed herein are administered to the individual being treated. As discussed in more detail below, a treatment session can be a single dosing event, or can be a multiple dosing regimen that occurs over a period of time. A treatment session results in a therapeutically effective amount of an active agent disclosed herein to be consistently maintained throughout the treatment session.

The term "non-treatment session" is used interchangeably herein with the terms "non-treatment period", "period of no treatment", "interval session" or "interval session of non-treatment" and refers to a period of time during which no active agent disclosed herein is administered to the individual being treated. The cessation of active agent administration during the non-treatment session results in the reduction of an active agent disclosed herein to sub-therapeutic levels in the individual being treated. As disclosed herein, a "non-treatment session" is not the same event as a period of time that intervenes between a dosing event making up a multiple dosing regimen that occurs over a period of time during a treatment session. If administration of one or more active agents disclosed herein during a treatment session is a repeated administration, the non-treatment session is longer than the intervening period between these repeated administrations during the treatment session.

The dosage regime may be determined in a number of ways. For example, the level of immunosuppression may be calibrated to a desired level for each patient who is being treated (personalized medicine), by monitoring the level or activity of IFN-γ-producing leukocytes or proliferation rate of leukocytes in response to stimulation individually, and adjusting the treatment session, the frequency of administration and the interval session empirically and personally as determined from the results of the monitoring.

Thus, the treatment session may comprise administering the active agent or pharmaceutical composition to the individual and the treatment session is maintained at least until the systemic presence or level of IFN-γ-producing leukocytes, or the rate of proliferation of leukocytes in response to stimulation rises above a reference, the administering is paused during the interval session, and the interval session is maintained as long as the level is above the reference, wherein the reference is selected from (a) the level of systemic presence or activity of IFN-γ-producing leukocytes, or the rate of proliferation of leukocytes in response to stimulation, measured in the most recent blood sample obtained from said individual before said administering; or (b) the level of systemic presence or activity of IFN-γ-producing leukocytes, or the rate of proliferation of leukocytes in response to stimulation, characteristic of a population of individuals afflicted with a disease, disorder, condition or injury of the CNS.

The length of the treatment and non-treatment or interval sessions may be determined by physicians in clinical trials directed to a certain patient population and then applied consistently to this patient population, without the need for monitoring the level of immunosuppression on a personal basis.

In certain embodiments, the treatment session comprises administering the active agent to the individual and the treatment session is maintained at least until the systemic presence of the active agent reaches therapeutic levels, the administering is paused during the interval session, and the interval session is maintained as long as the level is above about 95%, 90%, 80%, 70%, 60% or 50% of said therapeutic level. The term "therapeutic level" as used herein refers to generally accepted systemic levels of drugs used to block immune checkpoints in known therapies, such as cancer therapy (see above).

In certain embodiments, the treatment session comprises administering the active agent to the individual and the treatment session is maintained at least until the systemic presence or activity of the active agent reaches a therapeutic level, at which point the administration is then stopped, and a non-treatment period is maintained as long as the systemic presence or activity of the active agent is maintained above a threshold therapeutic level. In aspects of this embodiment, a threshold therapeutic level is a level that is, e.g. at least 10%, at least 20%, at least 30%, at least 40%, at least 50%, at least 60%, at least 70%, at least 80%, at least 90%, of the therapeutic level. The term "therapeutic level" as used herein refers to generally accepted systemic levels of drugs used to block immune checkpoints in known therapies, such as cancer therapy (see above). In aspects of this embodiment, the active agent is an anti-PD-1 antibody, an anti-PD-L1 antibody, an anti-PD-L2 antibody, an anti-CTLA-4 antibody, an anti-B7RP1 antibody, an anti-B7-H3 antibody, an anti-B7-H4 antibody, an anti-B7-H7 antibody, an anti-BTLA antibody, an anti-HVEM antibody, an anti-CD-27 antibody, an anti-CD40 antibody, an anti-CD40L antibody, an anti-CD70 antibody, an anti-CD80 antibody, an anti-CD86 antibody, an anti-CD137 antibody, an anti-CD137L antibody, an anti-OX40 antibody, an anti-OX40L antibody, an anti-TIM-3 antibody, an anti-Galectin9 antibody, an anti-KIR antibody, an anti-LAG-3 antibody, an anti-ICOS antibody, an anti-VISTA antibody, an anti-STING, an anti-TIGIT, anti-GITR or any combination thereof.

In certain embodiments, the treatment session comprises administering the active agent to the individual and the treatment session is maintained at least until the systemic presence or activity of the active agent reaches a therapeutic level, at which point the administration is then stopped, and a non-treatment period is maintained as long as a beneficial effect on cognition is maintained above the level before treatment commencement. In aspects of this embodiment, a beneficial effect on cognition is maintained is one that shows an improvement of, e.g. at least 10%, at least 20%, at least 30%, at least 40%, at least 50%, at least 60%, at least 70%, at least 80%, at least 90%, above the cognition level before treatment commencement. In aspects of this embodiment, the active agent is an anti-PD-1 antibody, an anti-PD-L1 antibody, an anti-PD-L2 antibody, an anti-CTLA-4 antibody, an anti-B7RP1 antibody, an anti-B7-H3 antibody, an anti-B7-H4 antibody, an anti-B7-H7 antibody, an anti-BTLA antibody, an anti-HVEM antibody, an anti-CD-27 antibody, an anti-CD40 antibody, an anti-CD40L antibody, an anti-CD70 antibody, an anti-CD80 antibody, an anti-CD86 antibody, an anti-CD137 antibody, an anti-CD137L antibody, an anti-OX40 antibody, an anti-OX40L antibody, an anti-TIM-3 antibody, an anti-Galectin9 antibody, an anti-KIR antibody, an anti-LAG-3 antibody, an anti-ICOS antibody, an anti-VISTA antibody, an anti-STING, an anti-TIGIT, anti-GITR or any combination thereof.

In certain embodiments, the treatment session comprises administering the active agent to the individual and the treatment session is maintained at least until the systemic presence or activity of the active agent reaches a therapeutic level, at which point the administration is then stopped, and a non-treatment period is maintained as long as a beneficial effect on vision is maintained above the level before treatment commencement. In aspects of this embodiment, a beneficial effect on vision is maintained is one that shows an improvement of, e.g. at least 10%, at least 20%, at least 30%, at least 40%, at least 50%, at least 60%, at least 70%, at least 80%, at least 90%, above the vision level before treatment commencement. In aspects of this embodiment, the active agent is an anti-PD-1 antibody, an anti-PD-L1 antibody, an anti-PD-L2 antibody, an anti-CTLA-4 antibody, an anti-B7RP1 antibody, an anti-B7-H3 antibody, an anti-B7-H4 antibody, an anti-B7-H7 antibody, an anti-BTLA antibody, an anti-HVEM antibody, an anti-CD-27 antibody, an anti-CD40 antibody, an anti-CD40L antibody, an anti-CD70 antibody, an anti-CD80 antibody, an anti-CD86 antibody, an anti-CD137 antibody, an anti-CD137L antibody, an anti-OX40 antibody, an anti-OX40L antibody, an anti-TIM-3 antibody, an anti-Galectin9 antibody, an anti-KIR antibody, an anti-LAG-3 antibody, an anti-ICOS antibody, an anti-VISTA antibody, an anti-STING, an anti-TIGIT, anti-GITR or any combination thereof.

In certain embodiments, the treatment session may be a single administration or it may comprise multiple administrations given during a prescribed period of time. In aspects of this embodiment, a treatment session may be multiple administrations given in the course of between, e.g., 1 day to four weeks, 2 days to four weeks, 3 days to four weeks, 4 days to four weeks, 5 days to four weeks, 6 days to four weeks, one week and four weeks, 10 days and four weeks, two weeks and four weeks, 17 days and four weeks or three weeks and four weeks. For example, the treatment session may comprise two administrations both given within one week, such as, e.g., the second administration given 1, 2, 3, 4, 5 or 6 days after the first administration. As another example, the treatment session may comprise three administrations all given within one week such as, e.g., given 1, 2 or 3 days after the preceding administration. As another example, the treatment session may comprise three administrations all given within two week such as, e.g., given 1, 2, 3, 4 or 5 days after the preceding administration. As another example, the treatment session may comprise four administrations all given within two week such as, e.g., given 1, 2, 3 or 4 days after the preceding administration. As another example, the treatment session may comprise four administrations all given within three week such as, e.g., given 1, 2, 3, 4, 5 or 6 days after the preceding administration. As another example, the treatment session may comprise five administrations all given within three week such as, e.g., given 1, 2, 3, 4 or 5 days after the preceding administration.

In certain embodiments, the interval session of non-treatment may be between one week and six months, for example between 2 weeks to 4 weeks, 3 weeks to 4 weeks, 2 weeks to 6 weeks, 3 weeks to 6 weeks, 4 weeks to 6 weeks, 5 weeks to 6 weeks, 2 weeks to 2 months, 3 weeks to 2 months, 4 weeks to 2 months, 5 weeks to 2 months, 6 weeks to 2 months, 7 weeks to 2 months, 2 months to 3 months, 2 months to 4 months, 3 months to 4 months, 3 months to 5 months, 3 months to 5 months, 4 months to 5 months, 1 week to 6 months, 2 weeks to 6 months, 3 weeks to 6 months, 4 weeks to 6 months, 6 weeks to 6 months, 2 months to 6 months, 3 months to 6 months, 4 months to 6 months or 5 months to 6 months. In certain embodiments, the interval session of non-treatment may be 1 to 2 months in length, 1 to 3 months in length or 2 to 3 months in length.

In the treatments session, the administration of the active agent or pharmaceutical composition may be a single administration or repeated administration, for example the active agent or pharmaceutical composition may be administered only once and then immediately followed by an interval, or it may be administered daily, or once every two, three, four, five or six days, or once weekly, once every two weeks, once every three weeks or once every four weeks. These frequencies are applicable to any active agent, may be based on commonly used practices in the art, and may finally be determined by physicians in clinical trials. Alternatively, the frequency of the repeated administration in the treatment session could be adapted according to the nature of the active agent, wherein for example, a small molecule may be administered daily and an antibody may be administered once every 3 days. It should be understood that when an agent is administered during a treatment session at a relatively low frequency, for example once per week during a treatment session of one month, or once per month during a treatment session of six months, this treatment session is followed by a non-treatment interval session, the length of which is longer than the period between the repeated administrations during the treatment session (i.e. longer than one week or one month, respectively, in this example). The pause of one week or one month between the administrations during the treatment session in this example is not considered an interval session.

The lengths of the treatment session and the non-treatment or interval session may be adjusted to the frequency of the administration such that, for example, a frequency of administering the active agent once every 3 days may result in a treatment session of 6 or 9 days and an interval session that is commenced accordingly.

If the treatment session consists of a single administration, the dosage regimen is determined by the length of the non-treatment interval, so that a single administration is followed by a non-treatment interval of 7, 8, 9, 10, 14, 18, 21, 24 or 28 days or longer before the next single-administration treatment session. In particular, the dosage regimen consists of single administrations interspersed with non-treatment intervals of non-treatment of 2, 3 or 4 weeks. In addition, the dosage regimen may consist of single administrations interspersed with non-treatment intervals of non-treatment of 2 to 4 weeks, 2 to 3 weeks or 3 to 4 weeks.

If the treatment session consists of a multiple administrations, the dosage regimen is determined by the length of the non-treatment interval, so that multiple administrations given within one week is followed by a non-treatment interval of 7, 10, 14, 18, 21, 24 or 28 days or longer before the next multiple-administration treatment session. In particular, the dosage regimen may consist of multiple administrations given within one week interspersed with non-treatment intervals of non-treatment of 2 or 3 or 4 weeks. In addition, the dosage regimen may consist of multiple administrations given within one week interspersed with intervals of non-treatment of 2 to 4 weeks, 2 to 3 weeks or 3 to 4 weeks.

As another example, the dosage regimen may comprise multiple administrations given within two weeks followed by a non-treatment interval of 2 weeks, 3 weeks or 1, 2, 3 or 4 months or longer before the next multiple-administration treatment session. In particular, the dosage regimen may consist of multiple administrations given within two weeks interspersed with intervals of non-treatment of 1, 2, 3 or 4 months. In addition, the dosage regimen may consists of multiple administrations given within two week interspersed with intervals of non-treatment of 1 to 2 months, 1 to 3 months, 1 to 4 months, 2 to 3 months, 2 to 4 months or 3 to 4 months.

As another example, the dosage regimen may comprise multiple administrations given within three week followed by 1, 2, 3, 4, 5 or 6 months or longer of non-treatment before the next multiple-administration treatment session. In particular, the dosage regimen may consist of multiple administrations given within three weeks interspersed with intervals of non-treatment of 1, 2, 3, 4, 5 or 6 months. In addition, the dosage regimen may consists of multiple administrations given within three weeks interspersed with intervals of non-treatment of 1 to 2 months, 1 to 3 months, 1 to 4 months, 1 to 5 months, 1 to 6 months, 2 to 3 months, 2 to 4 months, 2 to 5 months, 2 to 6 months, 3 to 4 months, 3 to 5 months, 3 to 6 months, 4 to 5 months, 4 to 6 months or 5 to 6 months.

Of course, a flexible dosage regimen is envisioned that starts with a certain regimen and is replaced with another. For example, treatment sessions, each one including 2 single administrations 3 days apart, with an interval of for example 1 week between the treatment sessions, could be replaced when considered appropriate by a dosage regimen including treatment sessions of single administrations separated by for example 2, 3 or 4 weeks intervals. As another example, treatment sessions, each one including 2 single administrations 7 days apart, with an interval of for example 2 weeks between the treatment sessions, could be replaced when considered appropriate by a dosage regimen including treatment sessions of single administrations separated by for example 2, 3, 4, 5 or 6 weeks intervals. As another example, treatment sessions, each one including 3 single administrations 3 days apart, with an interval of for example 2 weeks between the treatment sessions, could be replaced when considered appropriate by a dosage regimen including treatment sessions of single administrations separated by for example 2, 3, 4, 5 or 6 weeks intervals.

In any case, the dosage regimen, i.e. the length of the treatment session and the interval session, is calibrated such that the reduction in the level of immunosuppression, for example as measured by a reduction in the level of systemic presence or activity of regulatory T cells or the increase in the level of systemic presence or activity of IFN-γ producing leukocytes in the individual, is transient.

The method, active agent or pharmaceutical composition according to the present invention may be for treating a disease, disorder or condition of the CNS that is a neurodegenerative disease, disorder or condition. In aspects of this embodiment, the neurodegenerative disease, disorder or condition is Alzheimer's disease, amyotrophic lateral sclerosis, Parkinson's disease Huntington's disease, primary progressive multiple sclerosis; secondary progressive multiple sclerosis, corticobasal degeneration, Rett syndrome, a tauopathy, a retinal degeneration disorder; anterior ischemic optic neuropathy; glaucoma; uveitis; depression; trauma-associated stress or post-traumatic stress disorder, frontotemporal dementia, Lewy body dementias, mild cognitive impairments, posterior cortical atrophy, primary progressive aphasia or progressive supranuclear palsy. In certain embodiments, the condition of the CNS is aged-related dementia. In certain aspects of this embodiment, the condition of the CNS is Alzheimer's disease, amyotrophic lateral sclerosis, Parkinson's disease Huntington's disease.

Tauopathies are a clinically, morphologically and biochemically heterogeneous class of neurodegenerative diseases characterized by a pathological aggregation of tau protein in neurofibrillary or gliofibrillary tangles in the human brain. Tau is a microtubule-associated protein (MAP) that binds to microtubules and promotes their polymerization. It plays an important role in maintaining axonal transport and neuronal integrity but has a physiological role in dendrites, and it is expressed at low levels in glial cells. In a tauopathy, tangles are formed by hyperphosphorylation of tau causing it to aggregate in an insoluble form. Non-limiting examples of tauopathies include Alzheimer's disease, argyrophilic grain disease, chronic traumatic encephalopathy, corticobasal degeneration, dementia pugilistica, frontotemporal dementia, frontotemporal lobar degeneration, Hallervorden-Spatz disease, Huntington's disease, ganglioglioma, gangliocytoma, globular glial tauopathy, lead encephalopathy, lipofuscinosis, Lytico-Bodig disease (Parkinson-dementia complex of Guam), meningioangiomatosis, Parkinsonism disease linked to chromosome 17, Pick's disease, primary age-related tauopathy (PART), formerly known as neurofibrillary tangle-only dementia (NFT-dementia), postencephalitic parkinsonism, progressive supranuclear palsy, subacute sclerosing panencephalitis and tuberous sclerosis.

Retinal degeneration disorders are ones that result in the deterioration of the retina due to the death of photoreceptor cells. There are several causes for retinal degeneration, including artery or vein occlusion, diabetic retinopathy, retrolental fibroplasia/retinopathy of prematurity, or disease (usually hereditary). Symptoms include, without limitation, impaired vision, night blindness, retinal detachment, light sensitivity, glare sensitivity, tunnel vision, loss of depth perception, loss of contrast, night blindness, loss of central vision, loss of peripheral vision and total loss of vision. Retinal degeneration disorders include, without limitation, Age-Related Macular Degeneration (wet and dry), Retinitis Pigmentosa, Choroideremia, Cone-Rod Retinal Dystrophy, Gyrate Atrophy, Juvenile Retinoschisis, Vitelliform Macular Dystrophy (Best's Disease), Abetalipoproteinemia (Bassen-Kornzweig Disease), Bardet-Biedl Syndrome, Blue Cone Monochromatism Disease, Dominant Drusen, Goldman-Favre Vitreoretinal Dystrophy (Enhanced S-cone Syndrome), Kearns-Sayre Syndrome, Laurence-Moon Syndrome, Leber's Congenital Amaurosis, Leber's Refsum disease, Oguchi Disease, Peripapillary (pericentral) Choroidal Dystrophy, Pigment Pattern Dystrophy, Sorsby Macular Dystrophy, Stargardt's Disease, Stickler's Syndrome, Usher Syndrome and Wagner's Vitreoretinal Dystrophy.

In certain embodiments, each one of the active agents described above that blocks one of the immune checkpoints selected from ICOS-B7RP1, V-domain Ig suppressor of T cell activation (VISTA), B7-CD28-like molecule, CD40L-CD40, CD28-CD80, CD28-CD86, B7H3, B7H4, B7H7, BTLA-HVEM, CD137-CD137L, OX40L, CD27-CD70, STING, TIGIT and A2aR-Adenosine and indoleamine-2,3-dioxygenase (IDO)-L-tryptophan, such as an antibody against one of the two partners of the immune checkpoint, is for use in treating either one of a neurodegenerative disease, disorder or condition selected from Alzheimer's disease, amyotrophic lateral sclerosis, Parkinson's disease Huntington's disease, primary progressive multiple sclerosis; secondary progressive multiple sclerosis, corticobasal degeneration, Rett syndrome, a retinal degeneration disorder selected from the group consisting of age-related macular degeneration and retinitis pigmentosa; anterior ischemic optic neuropathy; glaucoma; uveitis; depression; trauma-associated stress or post-traumatic stress disorder, frontotemporal dementia, Lewy body dementias, mild cognitive impairments, posterior cortical atrophy, primary progressive aphasia or progressive supranuclear palsy. The treatment of any one of these diseases comprising the use of any one of these active agents can be done according to the regiment described above.

The method, active agent and pharmaceutical composition according to the present invention may further be for treating an injury of the CNS selected from spinal cord injury, closed head injury, blunt trauma, penetrating trauma, hemorrhagic stroke, ischemic stroke, cerebral ischemia, optic nerve injury, myocardial infarction, organophosphate poisoning and injury caused by tumor excision.

In certain embodiments, each one of the active agents described above that blocks one of the immune checkpoints selected from ICOS-B7RP1, V-domain Ig suppressor of T cell activation (VISTA), B7-CD28-like molecule, CD40L-CD40, CD28-CD80, CD28-CD86, B7H3, B7H4, B7H7, BTLA-HVEM, CD137-CD137L, OX40L, CD27-CD70, STING, TIGIT and A2aR-Adenosine and indoleamine-2,3-dioxygenase (IDO)-L-tryptophan, such as an antibody against one of the two partners of the immune checkpoint, is for use in treating an injury of the CNS selected from spinal cord injury, closed head injury, blunt trauma, penetrating trauma, hemorrhagic stroke, ischemic stroke, cerebral ischemia, optic nerve injury, myocardial infarction, organophosphate poisoning and injury caused by tumor excision. The treatment of any one of these injuries comprising the use of any one of these active agents can be done according to the regiment described above.

As stated above, the inventors have found that the present invention improves the cognitive function in mice that emulates Alzheimer's disease. Thus, the method, active agent and pharmaceutical composition may be for use in improving CNS motor and/or cognitive function, for example for use in alleviating age-associated loss of cognitive function, which may occur in individuals free of a diagnosed disease, as well as in people suffering from neurodegenerative disease. Furthermore, the method, active agent and pharmaceutical composition may be for use in alleviating loss of cognitive function resulting from acute stress or traumatic episode. The cognitive function mentioned herein above may comprise learning, memory or both.

It should be emphasized, that the improvement of cognitive function in mice that emulates Alzheimer's disease (5XFAD AD-Tg mice) were observed and characterized by the inventors in various stages of disease manifestation; both early and late progressive stages of disease pathology could be mitigated by the treatment. 5XFAD AD-Tg mice begin to display cerebral plaque pathology at the ages of 2.5 months and cognitive deficits at the ages of 5 months (Oakley et al, 2006). Of note, while in Example 2 below the inventors describe the therapeutic effect in 5XFAD mice at 6 months of age, in Example 5 they characterize the therapeutic effect in 5XFAD mice at 11 and 12 months of age—an extremely progressive stage of amyloid beta plaque deposition and cognitive deficits in this model. It is therefore expected that the proposed invention would be of relevance to patients of different stages of disease progression, such as Stage 1—Mild/Early (lasts 2-4 years); Stage 2—Moderate/Middle (lasts 2-10 years); and Stage 3—Severe/Late (lasts 1-3+ years).

The term "CNS function" as used herein refers, inter alia, to receiving and processing sensory information, thinking, learning, memorizing, perceiving, producing and understanding language, controlling motor function and auditory and visual responses, maintaining balance and equilibrium, movement coordination, the conduction of sensory information and controlling such autonomic functions as breathing, heart rate, and digestion.

The terms "cognition", "cognitive function" and "cognitive performance" are used herein interchangeably and are related to any mental process or state that involves but is not limited to learning, memory, creation of imagery, thinking, awareness, reasoning, spatial ability, speech and language skills, language acquisition and capacity for judgment attention. Cognition is formed in multiple areas of the brain such as hippocampus, cortex and other brain structures. However, it is assumed that long term memories are stored at least in part in the cortex and it is known that sensory information is acquired, consolidated and retrieved by a specific cortical structure, the gustatory cortex, which resides within the insular cortex.

In humans, cognitive function may be measured by any know method, for example and without limitation, by the clinical global impression of change scale (CIBIC-plus scale); the Mini Mental State Exam (MMSE); the Neuropsychiatric Inventory (NPI); the Clinical Dementia Rating Scale (CDR); the Cambridge Neuropsychological Test Automated Battery (CANTAB) or the Sandoz Clinical Assessment-Geriatric (SCAG). Cognitive function may also be measured indirectly using imaging techniques such as Positron Emission Tomography (PET), functional magnetic resonance imaging (fMRI), Single Photon Emission Computed Tomography (SPECT), or any other imaging technique that allows one to measure brain function.

An improvement of one or more of the processes affecting the cognition in a patient will signify an improvement of the cognitive function in said patient, thus in certain embodiments improving cognition comprises improving learning, plasticity, and/or long term memory. The terms "improving" and "enhancing" may be used interchangeably.

The term "learning" relates to acquiring or gaining new, or modifying and reinforcing, existing knowledge, behaviors, skills, values, or preferences.

The term "plasticity" relates to synaptic plasticity, brain plasticity or neuroplasticity associated with the ability of the brain to change with learning, and to change the already acquired memory. One measurable parameter reflecting plasticity is memory extinction.

The term "memory" relates to the process in which information is encoded, stored, and retrieved. Memory has three distinguishable categories: sensory memory, short-term memory, and long-term memory.

The term "long term memory" is the ability to keep information for a long or unlimited period of time. Long term memory comprises two major divisions: explicit memory (declarative memory) and implicit memory (non-declarative memory). Long term memory is achieved by memory consolidation which is a category of processes that stabilize a memory trace after its initial acquisition. Consolidation is distinguished into two specific processes, synaptic consolidation, which occurs within the first few hours after learning, and system consolidation, where hippocampus-dependent memories become independent of the hippocampus over a period of weeks to years.

The embodiments above that describe different features of the pharmaceutical composition of the present invention are relevant also for the method of the invention, because the method employs the same pharmaceutical composition.

In yet another aspect, the present invention provides methods for reducing Aβ-plaque burden in a patient diagnosed with Alzheimer's disease, comprising administering to said patient an active agent or pharmaceutical composition as defined herein above that causes reduction of the level of systemic immunosuppression by release of a restraint imposed on the immune system by one or more immune checkpoints.

In still another aspect, the present invention provides a method for reducing hippocampal gliosis in a patient diagnosed with Alzheimer's disease, comprising administering to said patient an active agent or pharmaceutical composition as defined herein above that causes reduction of the level of systemic immunosuppression by release of a restraint imposed on the immune system by one or more immune checkpoints.

Pharmaceutical compositions for use in accordance with the present invention may be formulated in conventional manner using one or more physiologically acceptable carriers or excipients. The carrier(s) must be "acceptable" in the sense of being compatible with the other ingredients of the composition and not deleterious to the recipient thereof.

The following exemplification of carriers, modes of administration, dosage forms, etc., are listed as known possibilities from which the carriers, modes of administration, dosage forms, etc., may be selected for use with the present invention. Those of ordinary skill in the art will understand, however, that any given formulation and mode of administration selected should first be tested to determine that it achieves the desired results.

Methods of administration include, but are not limited to, parenteral, e.g., intravenous, intraperitoneal, intramuscular, subcutaneous, mucosal (e.g., oral, intranasal, buccal, vaginal, rectal, intraocular), intrathecal, topical and intradermal routes. Administration can be systemic or local.

The term "carrier" refers to a diluent, adjuvant, excipient, or vehicle with which the active agent is administered. The carriers in the pharmaceutical composition may comprise a binder, such as microcrystalline cellulose, polyvinylpyrrolidone (polyvidone or povidone), gum tragacanth, gelatin, starch, lactose or lactose monohydrate; a disintegrating agent, such as alginic acid, maize starch and the like; a lubricant or surfactant, such as magnesium stearate, or sodium lauryl sulphate; and a glidant, such as colloidal silicon dioxide.

For oral administration, the pharmaceutical preparation may be in liquid form, for example, solutions, syrups or suspensions, or may be presented as a drug product for reconstitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid). The pharmaceutical compositions may take the form of, for example, tablets or capsules prepared by conventional means with pharmaceutically acceptable excipients such as binding agents (e.g., pregelatinized maize starch, polyvinyl pyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well-known in the art.

Preparations for oral administration may be suitably formulated to give controlled release of the active compound.

For buccal administration, the compositions may take the form of tablets or lozenges formulated in conventional manner.

The compositions may be formulated for parenteral administration by injection, e.g., by bolus injection or continuous infusion. Formulations for injection may be presented in unit dosage form, e.g., in ampoules or in multidose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen free water, before use.

The compositions may also be formulated in rectal compositions such as suppositories or retention enemas, e.g., containing conventional suppository bases such as cocoa butter or other glycerides.

For administration by inhalation, the compositions for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin, for use in an inhaler or insufflator may be formulated containing a powder mix of the compound and a suitable powder base such as lactose or starch.

The determination of the doses of the active ingredient to be used for human use is based on commonly used practices in the art, and will be finally determined by physicians in clinical trials. An expected approximate equivalent dose for administration to a human can be calculated based on the in vivo experimental evidence disclosed herein below, using known formulas (e.g. Reagan-Show et al. (2007) Dose translation from animal to human studies revisited. The FASEB Journal 22:659-661). According to this paradigm, the adult human equivalent dose (mg/kg body weight) equals a dose given to a mouse (mg/kg body weight) multiplied with 0.081.

Aspects of the present specification can also be described as follows:

1. A method of treating a treating a disease, disorder, condition or injury of the Central Nervous System to an individual in need thereof, the method comprising administering to the individual a composition comprising an active agent that causes reduction of the level of systemic immunosuppression by release of a restraint imposed on the immune system by one or more immune checkpoints, wherein the composition is administered by a dosage regime comprising at least one course of therapy, each course of therapy comprising in sequence a treatment session where the composition is administered to the individual followed by a non-treatment session where the composition is not administered to the individual, wherein the non-treatment period is longer than the treatment session; wherein, if administration of the composition during the treatment session is a repeated administration, the non-treatment period is longer than the period between repeated administrations during the treatment session; wherein administration of the composition transiently reduces levels of systemic immunosuppression and increases choroid plexus gateway activity in facilitating selective recruitment of immune cells into the central nervous system, thereby treating the individual.

2. Use of an active agent that causes reduction of the level of systemic immunosuppression by release of a restraint imposed on the immune system by one or more immune checkpoints in the treatment of a disease, disorder, condition or injury of the Central Nervous System.

3. Use of an active agent that causes reduction of the level of systemic immunosuppression by release of a restraint imposed on the immune system by one or more immune checkpoints in the manufacture of a medicament for the treatment of a disease, disorder, condition or injury of the Central Nervous System.

4. The method according to embodiment 1 or the use according to embodiments 2 or 3, wherein the active agent is an antibody, an antibody mimetic, an aptamer, a small molecule, a Neem leaf glycoprotein, a sCTLA-4, a silencing molecule, an OK-432, a combination of IL-12 and anti-CTLA-4, or any combination thereof.

5. The method according to embodiment 4 or the use according to embodiment 4, wherein the antibody is a polyclonal antibody or a monoclonal antibody.

6. The method according to embodiments 4 or 5 or the use according to embodiments 4 or 5, wherein the antibody is a dimer, a multimer, a multispecific antibody, a recombinant antibody, a chimeric antibody, bi-functional antibody, a cell-associated antibody like an Ig receptor, a linear antibody, a diabody, a minibody or a nanobody.

7. The method according to any one of embodiments 4-6 or the use according to any one of embodiments 4-6, wherein the antibody is a human antibody or a humanized antibody.

8. The method according to any one of embodiments 4-7 or the use according to any one of embodiments 4-7, wherein the antibody is an antagonistic antibody or an agonistic antibody.

9. The method according to any one of embodiments 4-8 or the use according to any one of embodiments 4-8, wherein the antibody is a neutralizing antibody.

10. The method according to any one of embodiments 4-9 or the use according to any one of embodiments 4-9, wherein the antibody is a full-length immunoglobulin molecule or an immunologically active fragment.
11. The method according to embodiment 10 or the use according to embodiment 10, wherein the immunologically active fragment is a single domain antibody (sdAb), a single-chain variable fragment (scFv), a Fab fragment, a F(ab')2 fragment, a Fc fragment, a Fd fragment, a Fv fragment.
12. The method according to any one of embodiments 4-11 or the use according to any one of embodiments 4-11, wherein the antibody is an anti-PD-1, an anti-PD-L1, an anti-PD-L2, an anti-CTLA-4, an anti-CD80, an anti-CD86, an anti-B7RP1, an anti-B7-H3, an anti-B7-H4, an anti-B7-H7, an anti-BTLA, an anti-HVEM, an anti-CD-27, an anti-CD40, an anti-CD40L, an anti-CD70, an anti-CD80, an anti-CD86, an anti-CD137, an anti-CD137L, an anti-OX40, an anti-OX40L, an anti-TIM-3, an anti-Galectin9, an anti-KIR, an anti-LAG-3, an anti-ICOS, an anti-VISTA, an anti-STING, an anti-TIGIT, anti-GITR or any combination thereof.
13. The method according to embodiment 4 or the use according to embodiment 4, wherein the antibody mimetic is an affibody molecule, an affilin, an affimer, an affitin, an alphabody, an anticalin, an avimer, a DARPin, a fynomer, a Kunitz domain peptide, or a monobody.
14. The method according to embodiment 4 or the use according to embodiment 4, wherein the aptamer is a DNA aptamer, a RNA aptamer, a XNA aptamer or a peptide aptamer.
15. The method according to embodiment 4 or the use according to embodiment 4, wherein the small molecule is a p300 inhibitor, a Sunitinib, a Polyoxometalate-1, an α,β-methyleneadenosine 5'-diphosphate, an arsenic trioxide, a GX15-070, a retinoic acid antagonist, a CCR4 antagonist, an adenosine receptor antagonist, an adenosine A1 receptor antagonist; an adenosine A2a receptor, an adenosine A2b receptor antagonist, an A3 receptor antagonist, an antagonist of indoleamine-2,3-dioxygenase or an HIF-1 regulator.
16. The method according to any one of embodiments 1-15 or the use according to any one of embodiments 4-15, wherein the administration of the composition during the treatment session is a single administration.
17. The method according to any one of embodiments 1-15 or the use according to any one of embodiments 4-15, wherein the administration of the composition during the treatment session is a repeated administration.
18. The method according to embodiment 17 or the use according to embodiment 17, wherein the repeated administration occurs once every day, once every two days, once every three days, once every four days, once every five days or once every six days.
19. The method according to embodiment 17 or the use according to embodiment 17, wherein the repeated administration occurs once weekly or once every two weeks, once every three weeks or once every four weeks.
20. The method according to any one of embodiments 1-19 or the use according to any one of embodiments 1-19, wherein the treatment session is from 1 day to four weeks.
21. The method according to embodiment 20 or the use according to embodiment 20, wherein the treatment session is from 3 days to four weeks.
22. The method according to embodiment 21 or the use according to embodiment 21, wherein the treatment session is from one week to four weeks.
23. The method according to any one of embodiments 1-22 or the use according to any one of embodiments 1-22, wherein the non-treatment period is from one week to six months.
24. The method according to embodiment 23 or the use according to embodiment 23, wherein the non-treatment period is from two weeks to six months.
25. The method according to embodiment 24 or the use according to embodiment 24, wherein the non-treatment period is from three weeks to six months.
26. The method according to embodiment 25 or the use according to embodiment 25, wherein the non-treatment period is from one month to three months.
27. The method according to embodiment 26 or the use according to embodiment 26, wherein the non-treatment period is from one month to two months.
28. The method according to any one of embodiments 1-27 or the use according to any one of embodiments 1-27, wherein the transient reduction in the level of systemic immunosuppression is associated with an increase in a systemic presence or activity of IFNγ-producing leukocytes and/or an increase in a systemic presence or activity of an IFNγ cytokine.
29. The method according to any one of embodiments 1-28 or the use according to any one of embodiments 1-28, wherein the transient reduction in the level of systemic immunosuppression is associated with an increase in a systemic presence or activity of effector T cells.
30. The method according to any one of embodiments 1-29 or the use according to any one of embodiments 1-29, wherein the transient reduction in the level of systemic immunosuppression is associated with a decrease in a systemic presence or activity of regulatory T cells and/or a decrease in a systemic presence of an IL-10 cytokine.
31. The method according to any one of embodiments 1-30 or the use according to any one of embodiments 1-30, wherein the transient reduction in the level of systemic immunosuppression is associated with a decrease in a systemic presence or myeloid-derived suppressor cells (MDSCs).
32. The method according to any one of embodiments 1-31 or the use according to any one of embodiments 1-31, wherein the transient reduction in the level of systemic immunosuppression occurs by release of a restraint imposed on the immune system by one or more immune checkpoints.
33. The method according to embodiment 32 or the use according to embodiment 32, wherein administration of the composition blocks the one or more immune checkpoints, thereby causing the transient reduction in the level of systemic immunosuppression.
34. The method according to embodiment 33 or the use according to embodiment 33, wherein the one or more immune checkpoints includes a PD-1-PD-L1, a PD-1-PD-L2, a CD28-CD80, a CD28-CD86, a CTLA-4-CD80, a CTLA-4-CD86, an ICOS-B7RP1, a B7H3, a B7H4, a B7H7, a B7-CD28-like molecule, a BTLA-HVEM, a KIR-MHC class I or II, a LAG3-MHC class I or II, a CD137-CD137L, an OX40-OX40L, a CD27-CD70, a CD40L-CD40, a TIM3-GAL9, a V-domain Ig suppressor of T cell activation (VISTA), a STimulator of INterferon Genes (STING), a T cell immunoglobulin and immunoreceptor tyrosine-based inhibitory motif domain (TIGIT), a glucocorticoid-induced tumor necrosis factor receptor related protein (GITR), an A2aR-Adenosine or an indoleamine-2,3-dioxygenase (IDO)-L-tryptophan.

35. The method according to any one of embodiments 1-34 or the use according to any one of embodiments 1-34, wherein the administration of the composition during the treatment session is maintained at least until a systemic presence or activity of IFNγ-producing leukocytes and/or an IFNγ cytokine rises above a reference, at which point the administration is stopped, and the non-treatment period is maintained as long as the systemic presence or activity of IFNγ-producing leukocytes and/or an IFNγ cytokine is above the reference, wherein the reference includes a) a level of a systemic presence or activity of IFNγ-producing leukocytes and/or an IFNγ cytokine measured in the most recent blood sample obtained from the individual before the administering; or b) a level of a systemic presence or activity of IFNγ-producing leukocytes and/or an IFNγ cytokine characteristic of a population of individuals afflicted with the disease, disorder, condition or injury of the Central Nervous System.

36. The method according to any one of embodiments 1-35 or the use according to any one of embodiments 1-35, wherein a cerebral level of soluble amyloid beta peptide is reduced in the individual, a cerebral amyloid beta (Aβ) plaque burden is reduced or cleared in the individual, a hippocampal gliosis is reduced in the individual, a cerebral level of a pro-inflammatory cytokine is reduced in the individual, a brain inflammation is decreased in the individual and/or a cognitive function is improved in the individual.

37. The method according to embodiment 36 or the use according to embodiment 36, wherein the improved cognitive function is learning, memory, creation of imagery, plasticity, thinking, awareness, reasoning, spatial ability, speech and language skills, language acquisition, capacity for judgment attention or any combination thereof.

38. The method according to any one of embodiments 1-37 or the use according to any one of embodiments 1-37, wherein the immune cells include monocytes, macrophages, or T cells.

39. The method according to embodiment 38 or the use according to embodiment 38, wherein the T cells include regulatory T cells.

40. The method according to any one of embodiments 1-39 or the use according to any one of embodiments 1-39, wherein the disease, disorder, condition or injury of the Central Nervous System is Alzheimer's disease, amyotrophic lateral sclerosis, Parkinson's disease Huntington's disease, primary progressive multiple sclerosis, secondary progressive multiple sclerosis, corticobasal degeneration, Rett syndrome, anterior ischemic optic neuropathy, glaucoma, uveitis, depression, trauma-associated stress or post-traumatic stress disorder, frontotemporal dementia, Lewy body dementias, mild cognitive impairments, posterior cortical atrophy, primary progressive aphasia or progressive supranuclear palsy 41. The method according to any one of embodiments 1-39 or the use according to any one of embodiments 1-39, wherein the disease, disorder, condition or injury of the Central Nervous System is a tauopathy.

42. The method according to embodiment 41 or the use according to embodiment 41, wherein the tauopathy is Alzheimer's disease, argyrophilic grain disease, chronic traumatic encephalopathy, corticobasal degeneration, dementia pugilistica, frontotemporal dementia, frontotemporal lobar degeneration, Hallervorden-Spatz disease, Huntington's disease, ganglioglioma, gangliocytoma, globular glial tauopathy, lead encephalopathy, lipofuscinosis, Lytico-Bodig disease (Parkinson-dementia complex of Guam), meningioangiomatosis, Parkinsonism disease linked to chromosome 17, Pick's disease, primary age-related tauopathy (PART), formerly known as neurofibrillary tangle-only dementia (NFT-dementia), postencephalitic parkinsonism, progressive supranuclear palsy, subacute sclerosing panencephalitis or tuberous sclerosis.

43. The method according to any one of embodiments 1-39 or the use according to any one of embodiments 1-39, wherein the disease, disorder, condition or injury of the Central Nervous System is a retinal degeneration disorder.

44. The method according to embodiment 43 or the use according to embodiment 43, wherein the retinal degeneration disorder is wet Age-Related Macular Degeneration, dry Age-Related Macular Degeneration, Retinitis Pigmentosa, Choroideremia, Cone-Rod Retinal Dystrophy, Gyrate Atrophy, Juvenile Retinoschisis, Vitelliform Macular Dystrophy (Best's Disease), Abetalipoproteinemia (Bassen-Kornzweig Disease), Bardet-Biedl Syndrome, Blue Cone Monochromatism Disease, Dominant Drusen, Goldman-Favre Vitreoretinal Dystrophy (Enhanced S-cone Syndrome), Kearns-Sayre Syndrome, Laurence-Moon Syndrome, Leber's Congenital Amaurosis, Leber's Refsum disease, Oguchi Disease, Peripapillary (pericentral) Choroidal Dystrophy, Pigment Pattern Dystrophy, Sorsby Macular Dystrophy, Stargardt's Disease, Stickler's Syndrome, Usher Syndrome or Wagner's Vitreoretinal Dystrophy.

EXAMPLES

The following non-limiting examples are provided for illustrative purposes only in order to facilitate a more complete understanding of representative embodiments now contemplated. These examples should not be construed to limit any of the embodiments described in the present specification, including those pertaining to the active agents, pharmaceutical compositions, or methods and uses disclosed herein.

Materials and Methods

Animals. 5XFAD transgenic mice (Tg6799) that co-overexpress familial AD mutant forms of human APP (the Swedish mutation, K670N/M671L; the Florida mutation, I716V; and the London mutation, V7171) and PS1 (M146L/L286V) transgenes under transcriptional control of the neuron-specific mouse Thy-1 promoter (Oakley et al, 2006), and AD double transgenic B6.Cg-Tg (APPswe, PSEN1dE9) 85Dbo/J mice (Borchelt et al, 1997) were purchased from The Jackson Laboratory. Genotyping was performed by PCR analysis of tail DNA, as previously described (Oakley et al, 2006). Heterozygous mutant $cx_3cr1^{GFP/+}$ mice (Jung et al, 2000) (B6.129P-$cx3cr1^{tm1Litt}$/J, in which one of the $CX_3CR1$ chemokine receptor alleles was replaced with a gene encoding GFP) were used as donors for BM chimeras. Foxp3.LuciDTR mice (Suffner et al, 2010) were bred with 5XFAD mice to enable conditional depletion of Foxp3$^+$ Tregs. Animals were bred and maintained by the Animal Breeding Center of the Weizmann Institute of Science. All experiments detailed herein complied with the regulations formulated by the Institutional Animal Care and Use Committee (IACUC) of the Weizmann Institute of Science.

RNA purification, cDNA synthesis, and quantitative real-time PCR analysis. Total RNA of the hippocampal dentate gyrus (DG) was extracted with TRI Reagent (Molecular Research Center) and purified from the lysates using an RNeasy Kit (Qiagen). Total RNA of the choroid plexus was extracted using an RNA MicroPrep Kit (Zymo Research). mRNA (1 μg) was converted into cDNA using a High Capacity cDNA Reverse Transcription Kit (Applied Biosystems). The expression of specific mRNAs was assayed using fluorescence-based quantitative real-time PCR (RT-qPCR). RT-qPCR reactions were performed using Fast-SYBR PCR Master Mix (Applied Biosystems). Quantification reactions were performed in triplicate for each sample using the standard curve method. Peptidylprolyl isomerase A (ppia) was chosen as a reference (housekeeping) gene. The amplification cycles were 95° C. for 5 s, 60° C. for 20 s, and 72° C. for 15 s. At the end of the assay, a melting curve was constructed to evaluate the specificity of the reaction. For ifn-γ and ppia gene analysis, the cDNA was pre-amplified in 14 PCR cycles with non-random PCR primers, thereby increasing the sensitivity of the subsequent real-time PCR analysis, according to the manufacturer's protocol (PreAmp Master Mix Kit; Applied Biosystems). mRNA expression was determined using TaqMan RT-qPCR, according to the manufacturer's instructions (Applied Biosystems). All RT-qPCR reactions were performed and analyzed using StepOne software V2.2.2 (Applied Biosystems). The following TaqMan Assays-on-Demand™ probes were used: Mm02342430_g1 (ppia) and Mm01168134_m1 (ifn-γ).

For all other genes examined, the following primers were used:

```
ppia
                                    (SEQ ID NO: 33)
forward 5'-AGCATACAGGTCCTGGCATCTTGT-3'
and (SEQ ID NO: 34)
reverse 5'-CAAAGACCACATGCTTGCCATCCA-3';

icam1
                                    (SEQ ID NO: 35)
forward 5'-AGATCACATTCACGGTGCTGGCTA-3'
and (SEQ ID NO: 36)
reverse 5'-AGCTTTGGGATGGTAGCTGGAAGA-3';

vcam1
                                    (SEQ ID NO: 37)
forward 5'-TGTGAAGGGATTAACGAGGCTGGA-3'
and (SEQ ID NO: 38)
reverse 5'-CCATGTTTCGGGCACATTTCCACA-3';

cxcl10
                                    (SEQ ID NO: 39)
forward 5'-AACTGCATCCATATCGATGAC-3'
and (SEQ ID NO: 40)
reverse 5'-GTGGCAATGATCTCAACAC-3';

ccl2
                                    (SEQ ID NO: 41)
forward 5'-CATCCACGTGTTGGCTCA-3'
and (SEQ ID NO: 42)
reverse 5'-GATCATCTTGCTGGTGAATGAGT-3';

tnf-γ
                                    (SEQ ID NO: 43)
forward 5'-GCCTCTTCTCATTCCTGCTT-3'
and (SEQ ID NO: 44)
reverse CTCCTCCACTTGGTGGTTTG-3';
```

```
-continued
il-1β
                                    (SEQ ID NO: 45)
forward 5'-CCAAAAGATGAAGGGCTGCTT-3'
and (SEQ ID NO: 46)
reverse 5'-TGCTGCTGCGAGATTTGAAG-3';

il-12p40
                                    (SEQ ID NO: 47)
forward 5'-GAAGTTCAACATCAAGAGCA-3'
and (SEQ ID NO: 48)
reverse 5'-CATAGTCCCTTTGGTCCAG-3';

il-10
                                    (SEQ ID NO: 49)
forward 5'-TGAATTCCCTGGGTGAGAAGCTGA-3'
and (SEQ ID NO: 50)
reverse 5'-TGGCCTTGTAGACACCTTGGTCTT-3';

tgfβ2
                                    (SEQ ID NO: 51)
forward 5'-AATTGCTGCCTTCGCCCTCTTTAC-3'
and (SEQ ID NO: 52)
reverse 5'-TGTACAGGCTGAGGACTTTGGTGT-3';

igf-1
                                    (SEQ ID NO: 53)
forward 5'-CCGGACCAGAGACCCTTTG
and (SEQ ID NO: 54)
reverse 5'-CCTGTGGGCTTGTTGAAGTAAAA-3';

bdnf
                                    (SEQ ID NO: 55)
forward 5'-GATGCTCAGCAGTCAAGTGCCTTT-3'
and (SEQ ID NO: 56)
reverse 5'-GACATGTTTGCGGCATCCAGGTAA-3';
```

Immunohistochemistry. Tissue processing and immunohistochemistry were performed on paraffin embedded sectioned mouse (6 μm thick) and human (10 μm thick) brains. For human ICAM-1 staining, primary mouse anti-ICAM (1:20 Abcam; ab2213) antibody was used. Slides were incubated for 10 min with 3% H2O2, and a secondary biotin-conjugated anti-mouse antibody was used, followed by biotin/avidin amplification with Vectastain ABC kit (Vector Laboratories). Subsequently, 3,3'-diaminobenzidine (DAB substrate) (Zytomed kit) was applied; slides were dehydrated and mounted with xylene-based mounting solution. For tissue stainings, mice were transcardially perfused with PBS prior to tissue excision and fixation. CP tissues were isolated under a dissecting microscope (Stemi DV4; Zeiss) from the lateral, third, and fourth ventricles of the brain. For whole mount CP staining, tissues were fixated with 2.5% paraformaldehyde (PFA) for 1 hour at 4° C., and subsequently transferred to PBS containing 0.05% sodium azide. Prior to staining, the dissected tissues were washed with PBS and blocked (20% horse serum, 0.3% Triton X-100, and PBS) for 1 h at room temperature. Whole mount staining with primary antibodies (in PBS containing 2% horse serum and 0.3% Triton X-100), or secondary antibodies, was performed for 1 h at room temperature. Each step was followed by three washes in PBS. The tissues were applied to slides, mounted with Immu-mount (9990402, from Thermo Scientific), and sealed with cover-slips. For staining of sectioned brains, two different tissue preparation protocols (paraffin embedded or microtomed free-floating sections) were applied, as previously described (Baruch et al, 2013; Kunis et al, 2013). The following primary antibodies were used: mouse anti-Aβ (1:300, Covance, #SIG-39320); rabbit anti-GFP (1:100, MBL, #598); rat anti-CD68 (1:300, eBioscience, #14-0681); rat anti-ICAM-1 (1:200, Abcam, #AB2213); goat anti-GFP (1:100, Abcam, #ab6658); rabbit anti-IBA-1 (1:300, Wako, #019-19741); goat anti-IL-10 (1:20, R&D systems, #AF519); rat anti-Foxp3 (1:20, eBioscience, #13-5773-80); rabbit anti-CD3 (1:500, Dako, #IS503); mouse anti-ZO-1, mouse anti-E-Cahedrin, and rabbit anti-Claudin-1 (all 1:100, Invitrogen, #33-9100, #33-4000, #51-9000); rabbit anti-GFAP (1:200, Dako, #Z0334). Secondary antibodies included: Cy2/Cy3/Cy5-conjugated donkey anti-mouse/goat/rabbit/rat antibodies (1:200; all from Jackson Immunoresearch). The slides were exposed to Hoechst nuclear staining (1:4000; Invitrogen Probes) for 1 min. Two negative controls were routinely used in immunostaining procedures, staining with isotype control antibody followed by secondary antibody, or staining with secondary antibody alone. For Foxp3 intracellular staining, antigen retrieval from paraffin-embedded slides was performed using Retreivagen Kit (#550524, #550527; BD Pharmingen™). Microscopic analysis, was performed using a fluorescence microscope (E800; Nikon) or laser-scanning confocal microscope (Carl Zeiss, Inc.). The fluorescence microscope was equipped with a digital camera (DXM 1200F; Nikon), and with either a 20× NA 0.50 or 40× NA 0.75 objective lens (Plan Fluor; Nikon). The confocal microscope was equipped with LSM 510 laser scanning capacity (three lasers: Ar 488, HeNe 543, and HeNe 633). Recordings were made on postfixed tissues using acquisition software (NIS-Elements, F3 [Nikon] or LSM [Carl Zeiss, Inc.]). For quantification of staining intensity, total cell and background staining was measured using ImageJ software (NIH), and intensity of specific staining was calculated, as previously described (Burgess et al, 2010). Images were cropped, merged, and optimized using Photoshop CS6 13.0 (Adobe), and were arranged using Illustrator CS5 15.1 (Adobe).

Paraffin embedded sections of human CP. Human brain sections of young and aged postmortem non-CNS-disease individuals, as well as AD patients, were obtained from the Oxford Brain Bank (formerly known as the Thomas Willis Oxford Brain Collection (TWOBC)) with appropriate consent and Ethics Committee approval (TW220). The experiments involving these sections were approved by the Weizmann Institute of Science Bioethics Committee.

Flow cytometry, sample preparation and analysis. Mice were transcardially perfused with PBS, and tissues were treated as previously described (Baruch et al, 2013). Brains were dissected and the different brain regions were removed under a dissecting microscope (Stemi DV4; Zeiss) in PBS, and tissues were dissociated using the gentleMACS™ dissociator (Miltenyi Biotec). Choroid plexus tissues were isolated from the lateral, third and fourth ventricles of the brain, incubated at 37° C. for 45 min in PBS (with $Ca^{2+}$/$Mg^{2+}$) containing 400 U/ml collagenase type IV (Worthington Biochemical Corporation), and then manually homogenized by pipetting. Spleens were mashed with the plunger of a syringe and treated with ACK (ammonium chloride potassium) lysing buffer to remove erythrocytes. In all cases, samples were stained according to the manufacturers protocols. All samples were filtered through a 70 µm nylon mesh, and blocked with anti-Fc CD16/32 (1:100; BD Biosciences). For intracellular staining of IFN-γ, the cells were incubated with para-methoxyamphetamine (10 ng/ml; Sigma-Aldrich) and ionomycin (250 ng/ml; Sigma-Aldrich) for 6 h, and Brefeldin-A (10 µg/ml; Sigma-Aldrich) was added for the last 4 h. Intracellular labeling of cytokines was done with BD Cytofix/Cytoperm™ Plus fixation/permeabilization kit (cat. no. 555028). For Treg staining, an eBioscience FoxP3 staining buffer set (cat. no. 00-5523-00) was used. The following fluorochrome-labeled monoclonal antibodies were purchased from BD Pharmingen, BioLegend, R&D Systems, or eBiosciences, and used according to the manufacturers protocols: PE or Alexa Fluor 450-conjugated anti-CD4; PE-conjugated anti-CD25; PerCP-Cy5.5-conjugated anti-CD45; FITC-conjugated anti-TCRβ; APC-conjugated anti-IFN-γ; APC-conjugated anti-FoxP3; Brilliant-violet-conjugated anti-CD45. Cells were analyzed on an LSRII cytometer (BD Biosciences) using FlowJo software. In each experiment, relevant negative control groups, positive controls, and single stained samples for each tissue were used to identify the populations of interest and to exclude other populations.

Preparation of BM chimeras. BM chimeras were prepared as previously described (Shechter et al, 2009; Shechter et al, 2013). In brief, gender-matched recipient mice were subjected to lethal whole-body irradiation (950 rad) while shielding the head (Shechter et al, 2009). The mice were then injected intravenously with $5 \times 10^6$ BM cells from $CX_3CR1^{GFP/+}$ donors. Mice were left for 8-10 weeks after BM transplantation to enable reconstitution of the hematopoietic lineage, prior to their use in experiments. The percentage of chimerism was determined by FACS analysis of blood samples according to percentages of GFP expressing cells out of circulating monocytes ($CD11b^+$). In this head-shielded model, an average of 60% chimerism was achieved, and CNS-infiltrating $GFP^+$ myeloid cells were verified to be $CD45^{high}/CD11b^{high}$, representing monocyte-derived macrophages and not microglia (Shechter et al, 2013).

Morris Water Maze. Mice were given three trials per day, for 4 consecutive days, to learn to find a hidden platform located 1.5 cm below the water surface in a pool (1.1 m in diameter). The water temperature was kept between 21-22° C. Water was made opaque with milk powder. Within the testing room, only distal visual shape and object cues were available to the mice to aid in location of the submerged platform. The escape latency, i.e., the time required to find and climb onto the platform, was recorded for up to 60 s. Each mouse was allowed to remain on the platform for 15 s and was then removed from the maze to its home cage. If the mouse did not find the platform within 60 s, it was manually placed on the platform and returned to its home cage after 15 s. The inter-trial interval for each mouse was 10 min. On day 5, the platform was removed, and mice were given a single trial lasting 60 s without available escape. On days 6 and 7, the platform was placed in the quadrant opposite the original training quadrant, and the mouse was retrained for three sessions each day. Data were recorded using the EthoVision V7.1 automated tracking system (Noldus Information Technology). Statistical analysis was performed using analysis of variance (ANOVA) and the Bonferroni post-hoc test. All MWM testing was performed between 10 a.m. and 5 p.m. during the lights-off phase.

Radial Arm Water Maze. The radial-arm water maze (RAWM) was used to test spatial learning and memory, as was previously described in detail (Alamed et al, 2006). Briefly, six stainless steel inserts were placed in the tank, forming six swim arms radiating from an open central area.

The escape platform was located at the end of one arm (the goal arm), 1.5 cm below the water surface, in a pool 1.1 m in diameter. The water temperature was kept between 21-22° C. Water was made opaque with milk powder. Within the testing room, only distal visual shape and object cues were available to the mice to aid in location of the submerged platform. The goal arm location remained constant for a given mouse. On day 1, mice were trained for 15 trials (spaced over 3 h), with trials alternating between a visible and hidden platform, and the last 4 trails with hidden platform only. On day 2, mice were trained for 15 trials with the hidden platform. Entry into an incorrect arm, or failure to select an arm within 15 sec, was scored as an error. Spatial learning and memory were measured by counting the number of arm entry errors or the escape latency of the mice on each trial. Training data were analyzed as the mean errors or escape latency, for training blocks of three consecutive trials.

Figure 16:
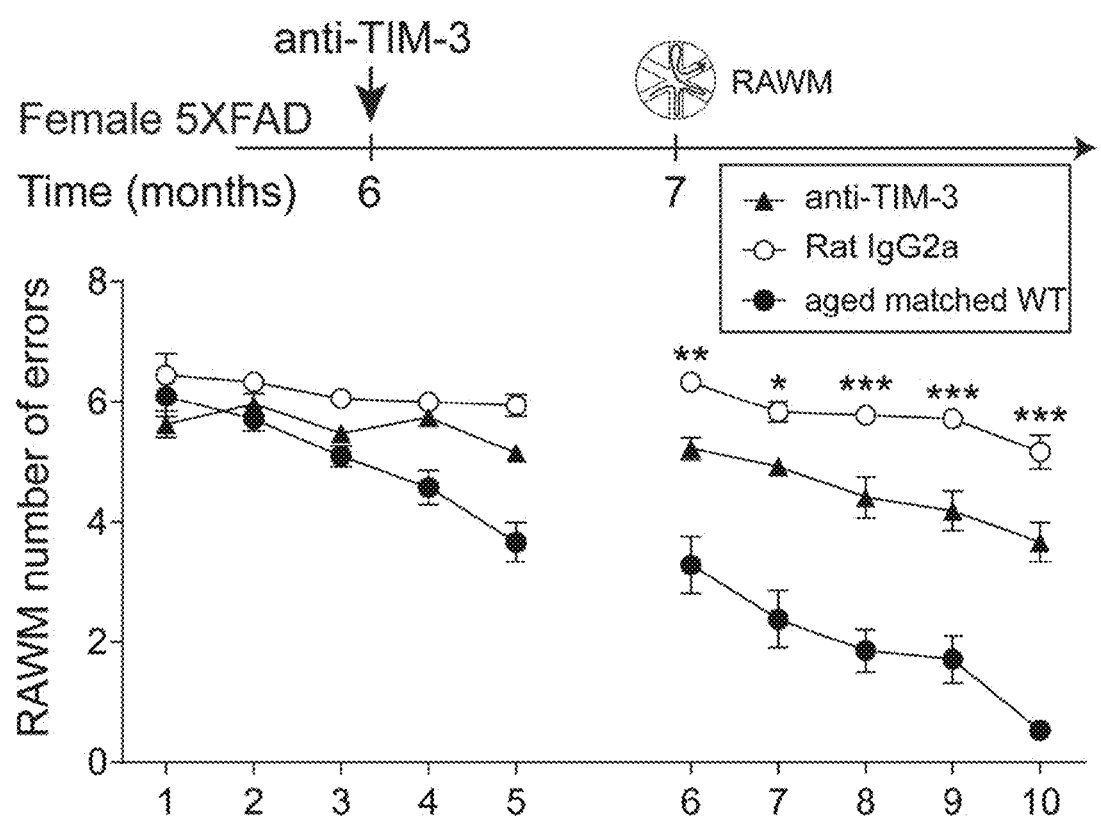
FIG. 16 shows the effect of a single administration of anti-TIM-3 antibody on cognitive decline in AD-Tg mice and illustrates the dosage scheme and the effect of anti-TIM-3 antibody treatment on spatial learning and memory performance using the radial arm water maze (RAWM) task at 7 months of age. Black arrows indicate time points of treatment, and illustrations indicate time points of cognitive testing.

GA administration. Each mouse was subcutaneously (s.c.) injected with a total dose of 100 μg of GA (batch no. P53640; Teva Pharmaceutical Industries, Petah Tiqva, Israel) dissolved in 200 μl of PBS. Mice were either injected according to a weekly-GA regimen (Butovsky et al, 2006), or daily-GA administration (FIG. 8 and FIG. 16). Mice were euthanized either 1 week after the last GA injection, or 1 month after treatment, as indicated for each experiment.

Figure 4:
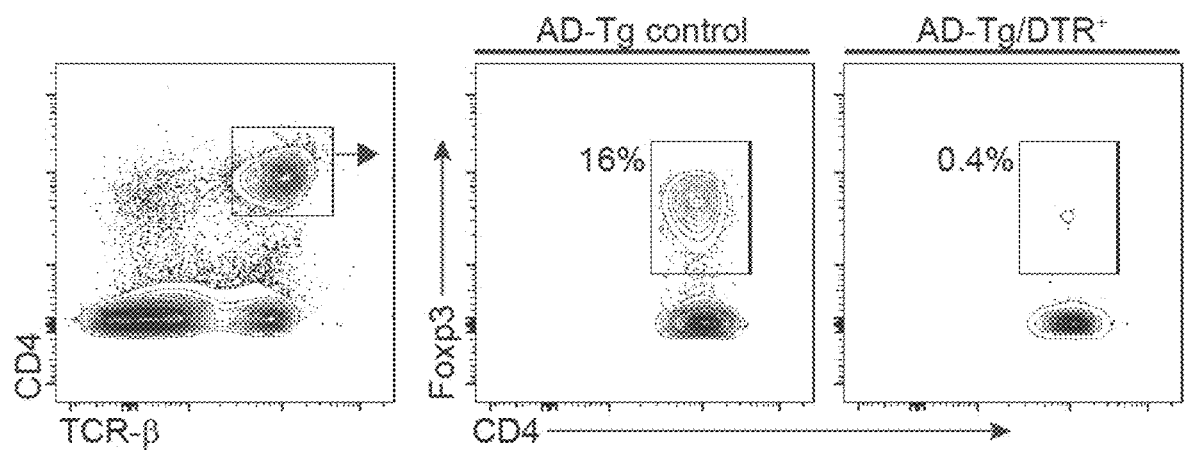
FIG. 4 shows gating strategy and representative flow cytometry plots of splenocytes from AD-Tg/Foxp3-DTR$^{+/-}$ mice, 1 day after the last injection of DTx. DTx was injected i.p. for 4 constitutive days, achieving ~99% depletion of Foxp3$^+$ cells.

Conditional ablation of Treg. Diphtheria toxin (DTx; 8 ng/g body weight; Sigma) was injected intraperitoneally (i.p.) daily for 4 consecutive days to Foxp3.LuciDTR mice (Suffner et al, 2010). The efficiency of DTx was confirmed by flow cytometry analysis of immune cells in the blood and spleen, achieving almost complete (>99%) depletion of the GFP-expressing FoxP3$^+$ CD4$^+$ Treg cells (FIG. 4).

P300 inhibition. Inhibition of p300 in mice was performed similarly to previously described (Liu et al, 2013). p300i (C646; Tocris Bioscience) was dissolved in DMSO and injected i.p. daily (8.9 mg kg$^{-1}$ d$^{-1}$, i.p.) for 1 week. Vehicle-treated mice were similarly injected with DMSO.

ATRA treatment. All-trans retinoic acid (ATRA) administration to mice was performed similarly to previously described (Walsh et al, 2014). ATRA (Sigma) was dissolved in DMSO and injected i.p. (8 mg kg$^{-1}$ d$^{-1}$) every other day over the course of 1 week. Vehicle-treated mice were similarly injected with DMSO.

Soluble Aβ (sAβ) protein isolation and quantification. Tissue homogenization and sAβ protein extraction was performed as previously described (Schmidt et al, 2005). Briefly, cerebral brain parenchyma was dissected and snap-frozen and kept at −80° C. until homogenization. Proteins were sequentially extracted from samples to obtain separate fractions containing proteins of differing solubility. Samples were homogenized in 10 volumes of ice-cold tissue homogenization buffer, containing 250 mM of sucrose, 20 mM of Tris base, 1 mM of ethylenediaminetetraacetic acid (EDTA), and 1 mM of ethylene glycol tetraacetic acid (pH 7.4), using a ground glass pestle in a Dounce homogenizer. After six strokes, the homogenate was mixed 1:1 with 0.4% diethylamine (DEA) in a 100-mM NaCl solution before an additional six strokes, and then centrifuged at 135,000 g at 4° C. for 45 min. The supernatant (DEA-soluble fraction containing extracellular and cytosolic proteins) was collected and neutralized with 10% of 0.5M of Tris-HCl (pH 6.8). Aβ$_{1-40}$ and Aβ$_{1-42}$ were individually measured by enzyme-linked immunosorbant assay (ELISA) from the soluble fraction using commercially available kits (Biolegend; #SIG-38954 and #SIG-38956, respectively) according to the manufacturer instructions.

Aβ Plaque Quantitation. From each brain, 6 μm coronal slices were collected, and eight sections per mouse, from four different pre-determined depths throughout the region of interest (dentate gyrus or cerebral cortex) were immunostained. Histogram-based segmentation of positively stained pixels was performed using the Image-Pro Plus software (Media Cybernetics, Bethesda, Md., USA). The segmentation algorithm was manually applied to each image, in the dentate gyrus area or in the cortical layer V, and the percentage of the area occupied by total Aβ immunostaining was determined. Plaque numbers were quantified from the same 6 μm coronal brain slices, and are presented as average number of plaques per brain region. Prior to quantification, slices were coded to mask the identity of the experimental groups, and plaque burden was quantified by an observer blinded to the identity of the groups.

Statistical analysis. The specific tests used to analyze each set of experiments are indicated in the figure legends. Data were analyzed using a two-tailed Student's t test to compare between two groups, one-way ANOVA was used to compare several groups, followed by the Newman-Keuls post-hoc procedure for pairwise comparison of groups after the null hypothesis was rejected (P<0.05). Data from behavioral tests were analyzed using two-way repeated-measures ANOVA, and Bonferroni post-hoc procedure was used for follow-up pairwise comparison. Sample sizes were chosen with adequate statistical power based on the literature and past experience, and mice were allocated to experimental groups according to age, gender, and genotype. Investigators were blinded to the identity of the groups during experiments and outcome assessment. All inclusion and exclusion criteria were pre-established according to the IACUC guidelines. Results are presented as means±s.e.m. In the graphs, y-axis error bars represent s.e.m. Statistical calculations were performed using the GraphPad Prism software (GraphPad Software, San Diego, Calif.).

Example 1

Figure 1B:
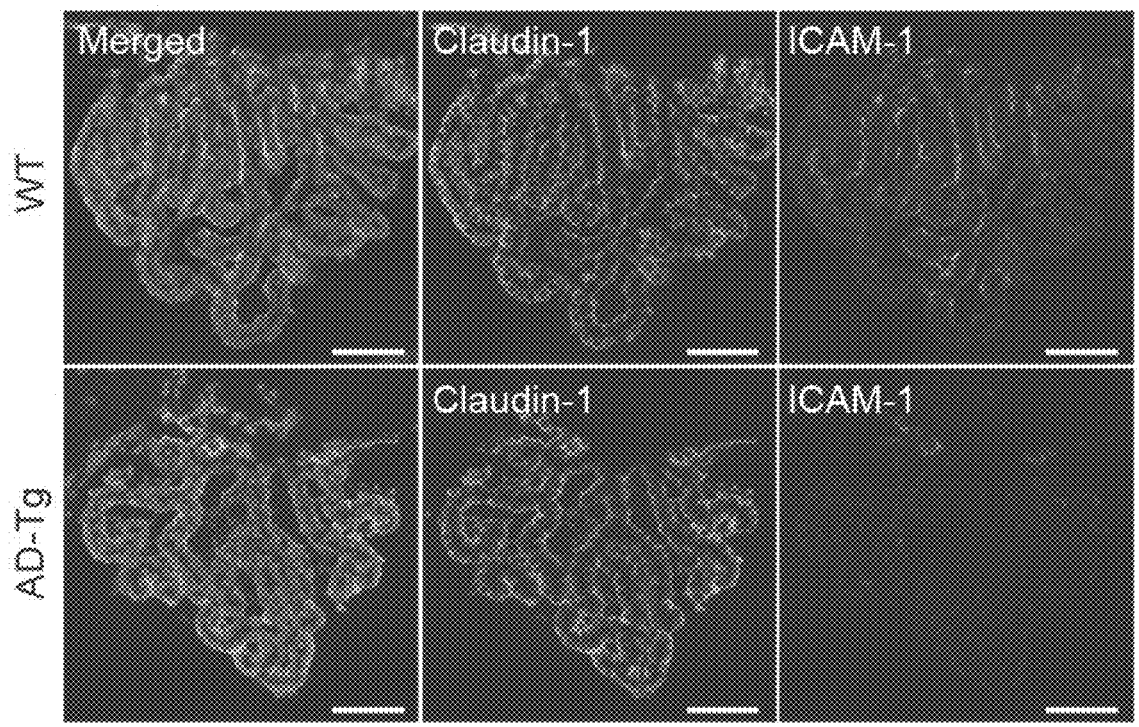
Figure 2A:
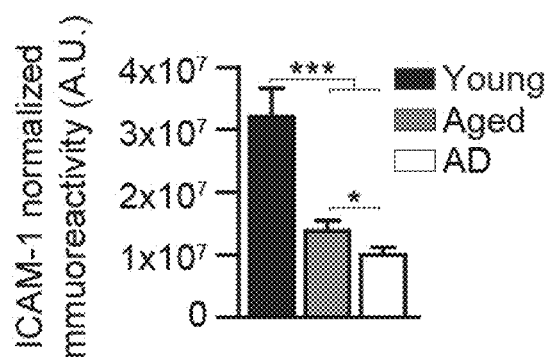
FIGS. 2A-C show (A) Quantification of ICAM-1 immunoreactivity in human postmortem CP of young and aged non-CNS diseased, and AD patients (n=5 per group; one-way ANOVA followed by Newman-Keuls post hoc analysis); (B) flow cytometry analysis for IFN-γ-expressing immune cells (intracellularly stained, and pre-gated on CD45) in CPs of 8-month old AD-Tg mice and age-matched WT controls. Shaded histogram represents isotype control (n=4-6 per group; Student's t test); and (C) mRNA expression levels of ifn-γ, measured by RT-qPCR, in CP tissues isolated from 4- and 8-month old AD-Tg mice, compared to age-matched WT controls (n=5-8 per group; Student's t test for each time point). In all panels, error bars represent mean±s.e.m.; *, $P<0.05$; , $P<0.01$;*, $P<0.001$.
Figure 2B:
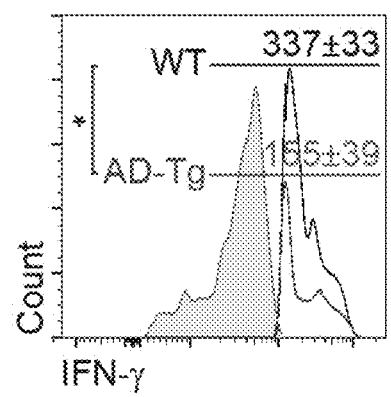
Figure 2C:
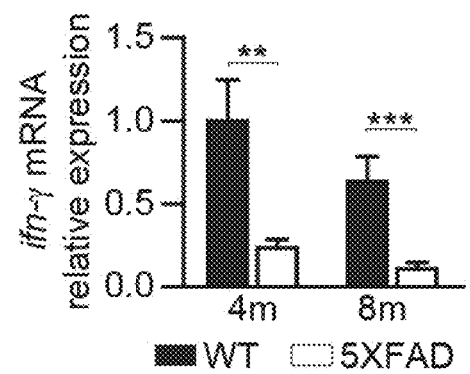

Choroid Plexus (CP) Gateway Activity Along Disease Progression in the Mouse Model of AD We first examined CP activity along disease progression in the 5XFAD transgenic mouse model of AD (AD-Tg); these mice co-express five mutations associated with familial AD and develop cerebral Aβ pathology and gliosis as early as 2 months of age (Oakley et al, 2006). We found that along the progressive stages of disease pathology, the CP of AD-Tg mice, compared to age-matched wild-type (WT) controls, expressed significantly lower levels of leukocyte homing and trafficking determinants, including icam1, vcam1, cxcl10, and ccl2 (FIG. 1A), shown to be upregulated by the CP in response to acute CNS damage, and needed for transepithelial migration of leukocytes (Kunis et al, 2013; Shechter et al, 2013). Immunohistochemical staining for the integrin ligand, ICAM-1, confirmed its reduced expression by the CP epithelium of AD-Tg mice (FIG. 1b). In addition, staining for ICAM-1 in human postmortem brains, showed its age-associated reduction in the CP epithelium, in line with our previous observations (Baruch et al, 2014), and quantitative assessment of this effect revealed further decline in AD patients compared to aged individuals without CNS disease (FIG. 2A). Since the induction of leukocyte trafficking determinants by the CP is dependent on epithelial interferon (IFN)-γ signaling (Kunis et al, 2013), we next tested whether the observed effects could reflect loss of IFN-γ availability at the CP. Examining the CP of 5XFAD AD-Tg mice using flow cytometry intracellular staining, revealed significantly lower numbers of IFN-γ-producing cells in this compartment (FIG. 2B), and quantitative real-time PCR (RT-qPCR) analysis confirmed lower mRNA expression levels of ifn-γ at the CP of AD-Tg mice compared to age-matched WT controls (FIG. 2C).

Example 2

Figure 3A:
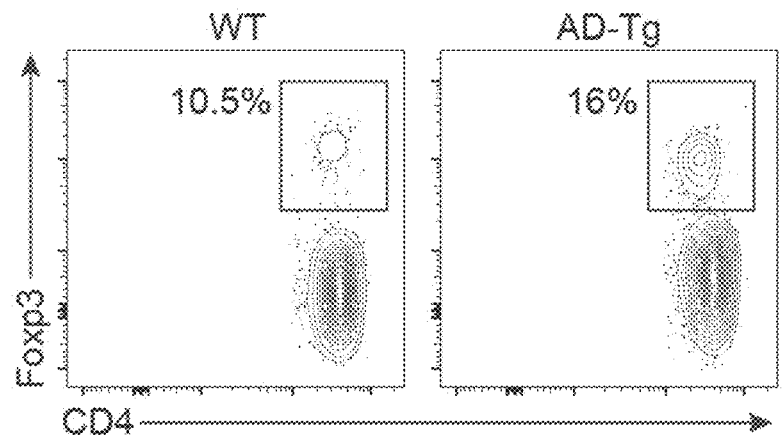
FIGS. 3A-B depict (A) representative flow cytometry plots of CD4$^+$Foxp3$^+$ splenocyte frequencies (pre-gated on TCRβ) in 8-month old AD-Tg and WT control mice; and (B) quantitative analysis of splenocytes from 1, 2, 4 and 8-month AD-Tg and WT control mice (n=6-8 per group; Student's t test for each time point). In all panels, error bars represent mean±s.e.m.; *, $P<0.05$; , $P<0.01$;*, $P<0.001$.
Figure 3B:
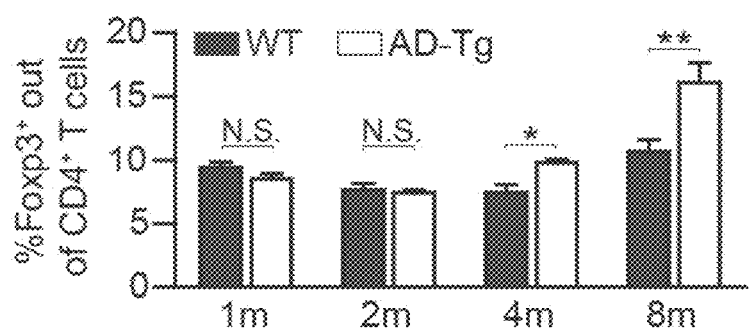
Figure 5A:
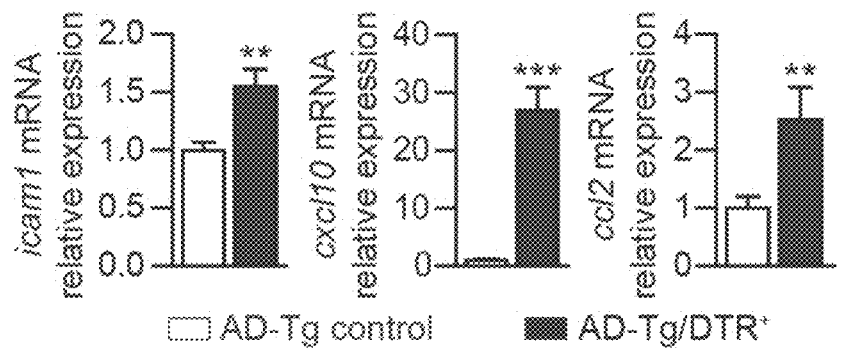
FIGS. 5A-G show the effects of transient depletion of Tregs in AD-Tg mice. (A) AD-Tg/Foxp3-DTR$^+$ (which express the DTR transgene) and a non-DTR-expressing AD-Tg littermate (AD-Tg/Foxp3-DTR⁻) control group were treated with DTx for 4 constitutive days. CP mRNA expression levels for the genes icam1, cxcl10 and ccl2, measured by RT-qPCR, in 6-month old DTx-treated AD-Tg mice; 1 day after the last DTx injection (n=6-8 per group; Student's t test). (B-D) Flow cytometry analysis of the brain parenchyma (excluding the choroid plexus, which was separately excised) of 6-month old DTx-treated AD-Tg mice and controls. 3 weeks following the last DTx injection. Quantitative flow cytometry analysis showing increased numbers of CD11b$^{high}$/CD45$^{high}$ mo-MΦ and CD4⁺ T cells (B), and representative flow cytometry plots (C) and quantitative analysis (D) of CD4⁺Foxp3⁺ Treg frequencies, in the brain parenchyma of AD-Tg/Foxp3-DTR⁺ mice and AD-Tg/Foxp3-DTR⁻ controls treated with DTx (n=3-7 per group; Student's t test). (E) mRNA expression levels of foxp3 and il10 in the brain parenchyma of 6-month old DTx-treated AD-Tg AD-Tg/Foxp3-DTR⁺ and AD-Tg/Foxp3-DTR-contros, 3 weeks after the last DTx injection (n=6-8 per group; Student's t test). (F) quantitative analysis of GFAP immunostaining, showing reduced astrogliosis in hippocampal sections from 6-month old DTx-treated AD-Tg/Foxp3-DTR⁺ and AD-Tg/Foxp3-DTR⁻ control mice, 3 weeks following the last DTx injection (scale bar, 50 μm; n=3-5 per group; Student's t test). (G) mRNA expression levels of il-12p40 and tnf-a in the brain parenchyma, 3 weeks following the last DTx injection (n=6-8 per group; Student's t test). In all panels, error bars represent mean±s.e.m.; *, P<0.05; , P<0.01;*, P<0.001.
Figure 5B:
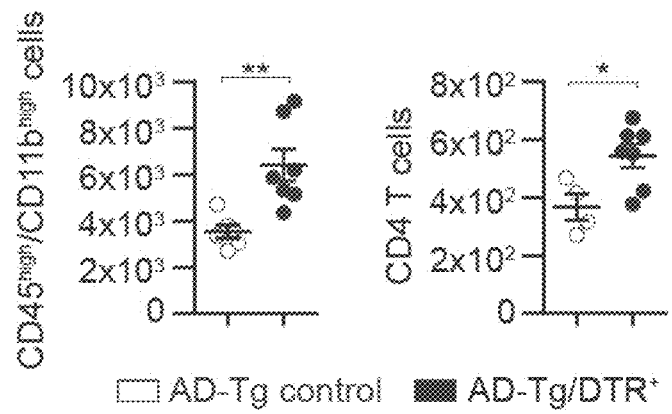
Figure 5C:
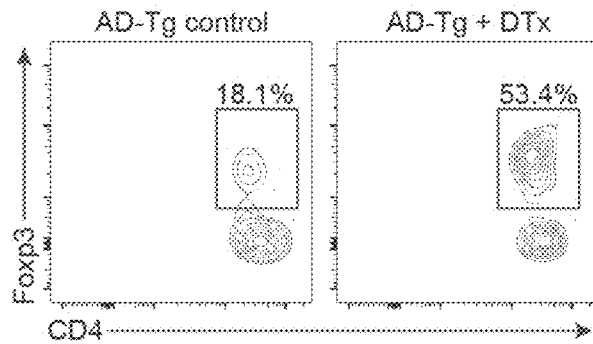
Figure 5D:
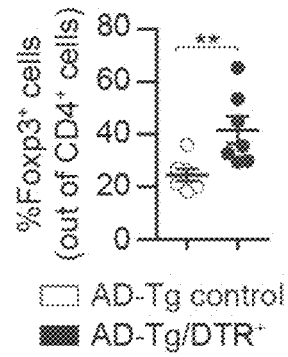
Figure 5E:
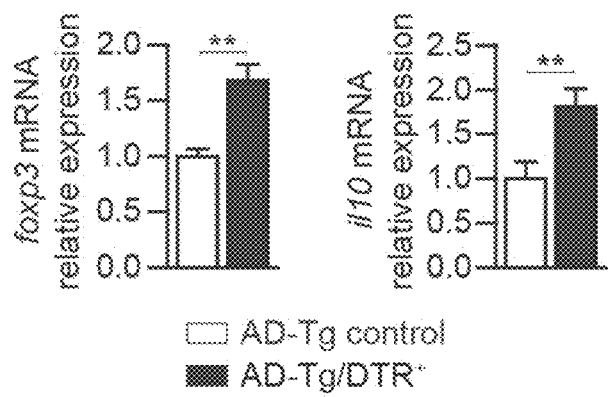

The Functional Relationships Between Treg-Mediated Systemic Immune Suppression, CP Gateway Activity, and AD Pathology Regulatory T cells (Tregs) play a pivotal role in suppressing systemic effector immune responses (Sakaguchi et al, 2008). We envisioned that Treg-mediated systemic immune suppression affects IFN-γ availability at the CP, and therefore focused on the involvement of Tregs in AD pathology. In line with previous reports of elevated Treg levels and suppressive activities in AD patients (Rosenkranz et al, 2007; Saresella et al, 2010; Torres et al, 2013), evaluating Foxp3$^+$ Treg frequencies in splenocytes of 5XFAD AD-Tg mice, relative to their age-matched WT littermates, revealed their elevated levels along disease progression (FIG. 3A, B). To study the functional relationships between Treg-mediated systemic immune suppression, CP gateway activity, and AD pathology, we crossbred 5XFAD AD-Tg mice with Foxp3-diphtheria toxin receptor (DTR$^+$) mice, enabling transient conditional in vivo depletion of Foxp3$^+$ Tregs in AD-Tg/DTR$^+$ mice by administration of diphtheria toxin (DTx) (FIG. 4A). Transient depletion of Tregs resulted in elevated mRNA expression of leukocyte trafficking molecules by the CP of AD-Tg/DTR$^+$ mice relative to DTx-treated AD-Tg/DTR$^-$ littermates (FIG. 5A). Analysis of the long-term effect of the transient Treg depletion on the brain parenchyma (3 weeks later), revealed immune cell accumulation in the brain, including elevated numbers of CD45$^{high}$/CD11b$^{high}$ myeloid cells, representing infiltrating mo-MΦ (Shechter et al, 2013), and CD4$^+$ T cells (FIG. 5B). In addition, the short and transient depletion of Tregs resulted in a marked enrichment of Foxp3$^+$ Tregs among the CD4$^+$ T cells that accumulated within the brain, as assessed by flow cytometry (FIG. 5C, D). RT-qPCR analysis of the hippocampus showed increased expression of foxp3 and il10 mRNA (FIG. 5E).

Figure 5F:
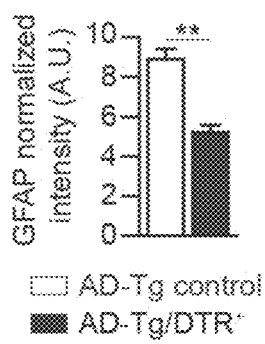
Figure 5G:
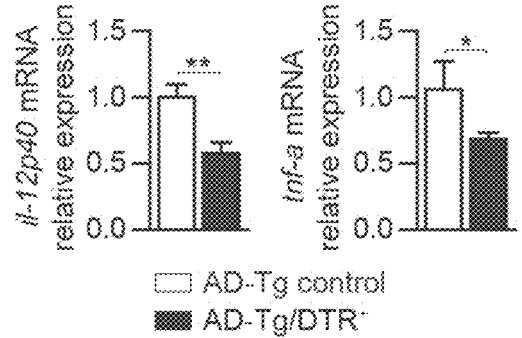
Figure 6A:
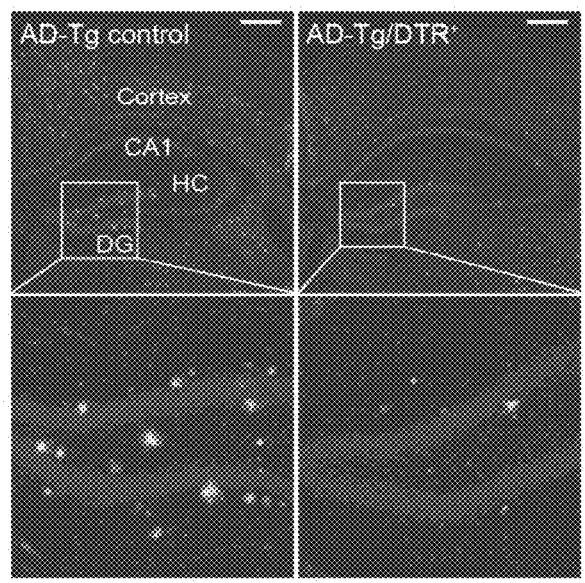
FIGS. 6A-E show the effect of transient depletion of Tregs on Aβ plaques learning/memory performance. (A) Representative microscopic images and (B) quantitative analysis of the brains of 5-month old DTx-treated AD-Tg/Foxp3-DTR⁺ and AD-Tg/Foxp3-DTR⁻ control mice, 3 weeks after the last DTx injection; immunostained for Aβ plaques and Hoechst nuclear staining (scale bar, 250 μm). Mean Aβ plaque area and numbers in the hippocampal dentate gyrus (DG) and the 5$^{th}$ layer of the cerebral cortex were quantified (in 6 μm brain slices; n=5-6 per group; Student's t test).
Figure 6B:
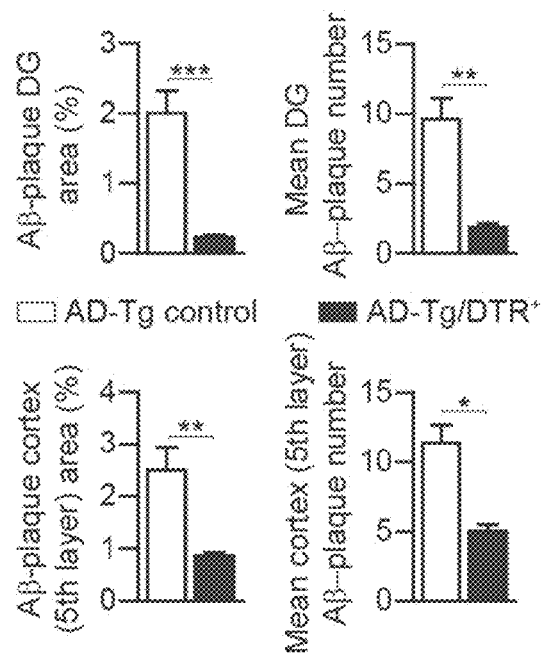
Figure 6C:
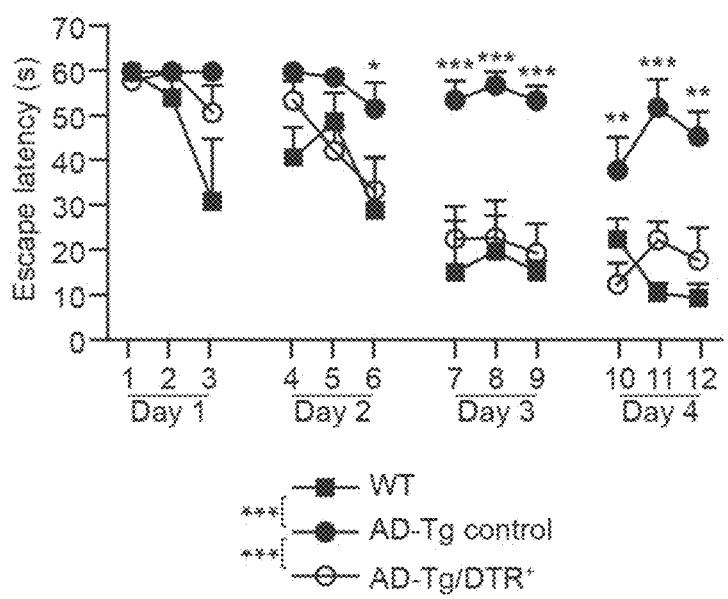
Figure 6D:
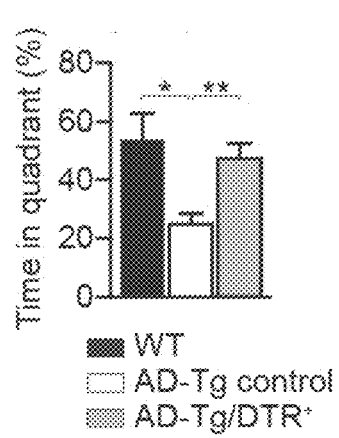
Figure 6E:
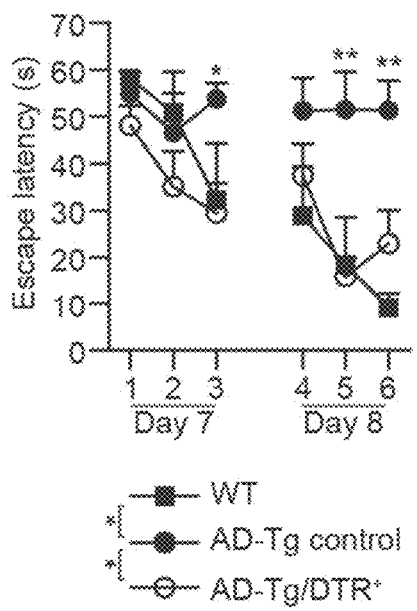

We next examined whether the short-term depletion of Tregs, which was followed by accumulation of immunoregulatory cells in sites of brain pathology, led to a long-term effect on brain function. We observed reduction in hippocampal gliosis (FIG. 5F), and reduced mRNA expression levels of pro-inflammatory cytokines, such as il-12p40 and tnf-α (FIG. 5G). Moreover, cerebral Aβ plaque burden in the hippocampal dentate gyrus, and the cerebral cortex (5$^{th}$ layer), two brain regions exhibiting robust Aβ plaque pathology in 5XFAD AD-Tg mice (Oakley et al, 2006), was reduced (FIG. 6A, B). Evaluating the effect on cognitive function, using the Morris water maze (MWM) test, revealed a significant improvement in spatial learning and memory in AD-Tg/DTR$^+$ mice following the Treg depletion, relative to DTx-treated AD-Tg/DTR$^-$ aged matched mice, reaching performance similar to that of WT mice (FIG. 6C-E). Taken together, these data demonstrated that transiently breaking Treg-mediated systemic immune suppression in AD-Tg mice resulted in accumulation of inflammation-resolving cells, including mo-MΦ and Tregs, in the brain, and was followed by resolution of the neuroinflammatory response, clearance of Aβ, and reversal of cognitive decline.

Example 3

Figure 7:
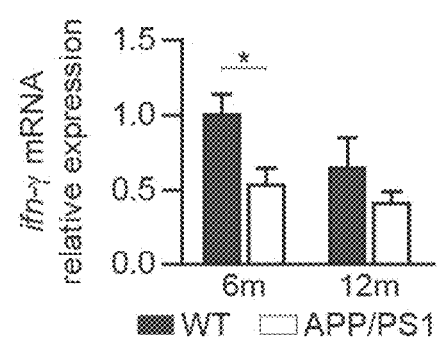
FIG. 7 shows mRNA expression levels of ifn-γ, measured by RT-qPCR, in CPs isolated from 6- and 12-month old APP/PS1 AD-Tg mice (a mouse model for Alzheimer's disease (see Materials and Methods)), compared to age-matched WT controls (n=5-8 per group; Student's t test). Error bars represent mean±s.e.m.; *, P<0.05.
Figure 8A:
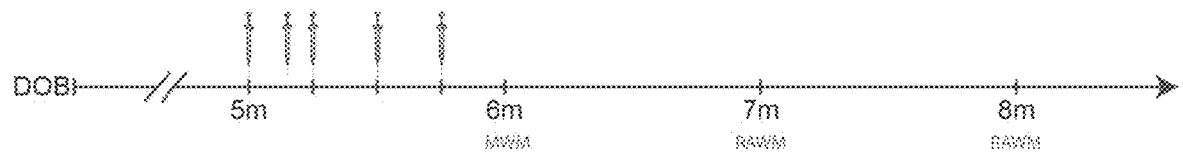
FIGS. 8A-I show the therapeutic effect of administration of weekly Glatiramer acetate (GA) in AD-Tg mice. (A) Schematic representation of weekly-GA treatment regimen. Mice (5-month old) were s.c. injected with GA (100 μg), twice during the first week (on day 1 and 4), and once every week thereafter, for an overall period of 4 weeks. The mice were examined for cognitive performance, 1 week (MWM), 1 month (RAWM) and 2 months (RAWM, using different experimental spatial settings) after the last injection, and for hippocampal inflammation.
Figure 8B:
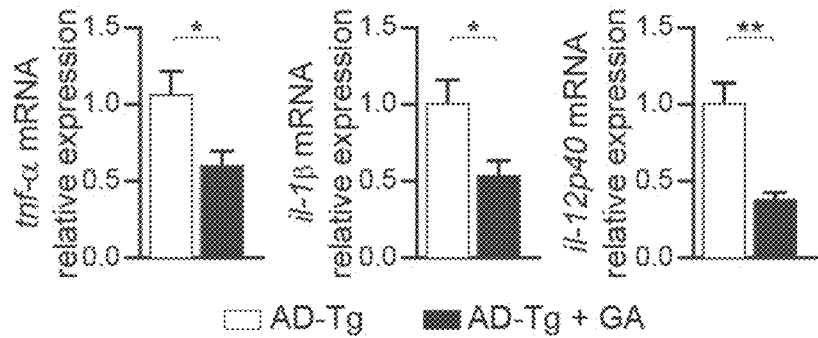
Figure 8C:
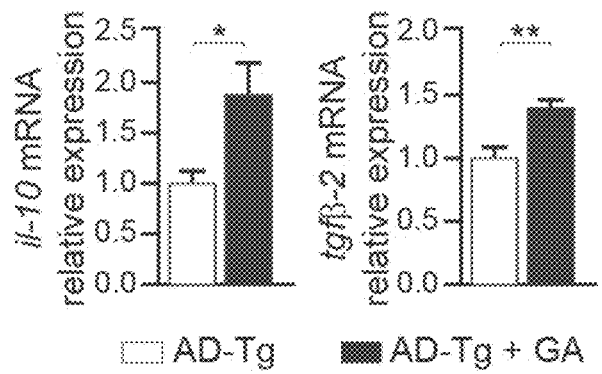
Figure 8D:
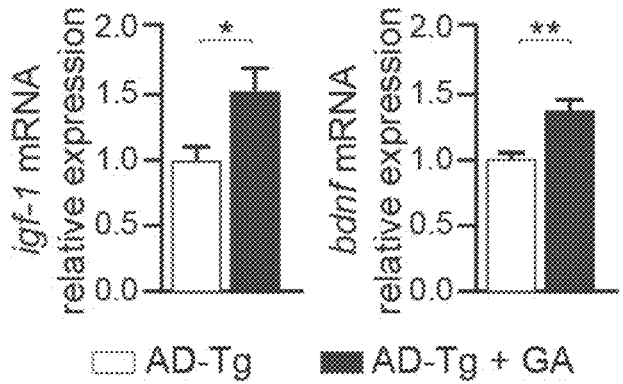
Figure 8E:
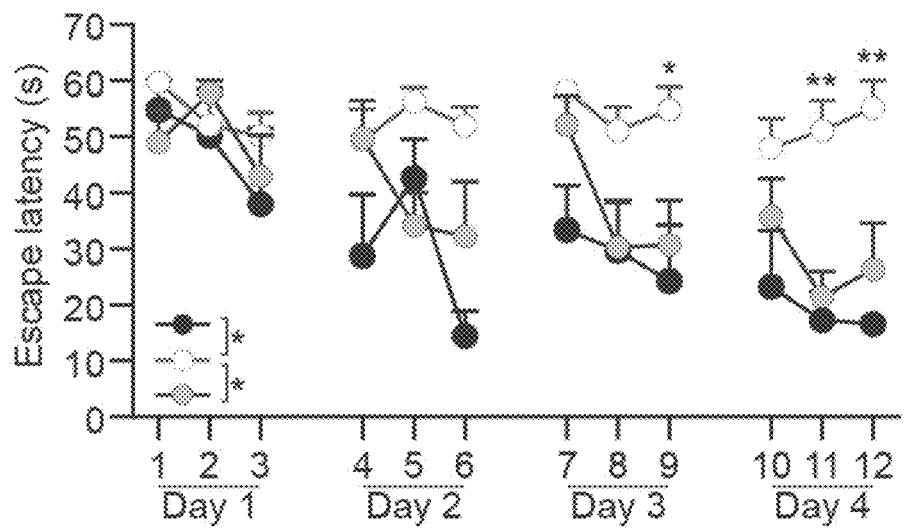
Figure 8F:
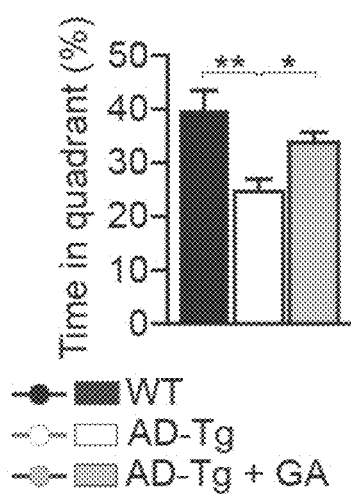
Figure 8G:
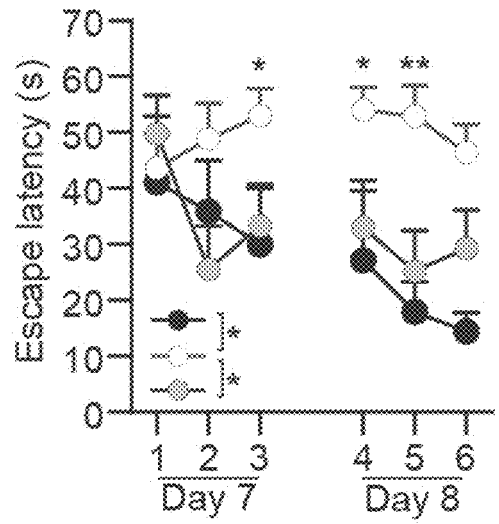
Figure 8H:
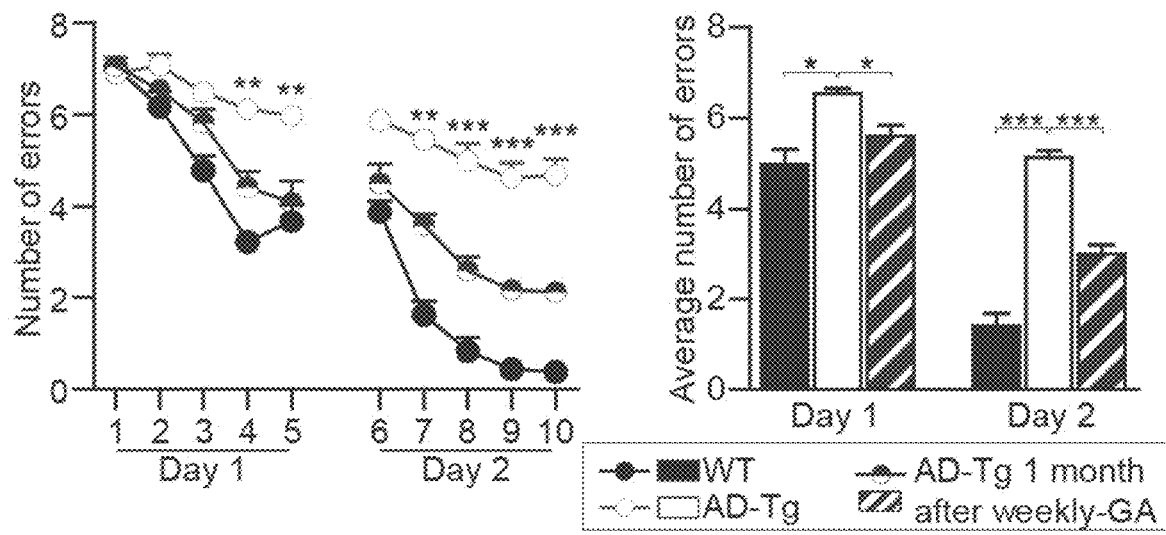
Figure 8I:
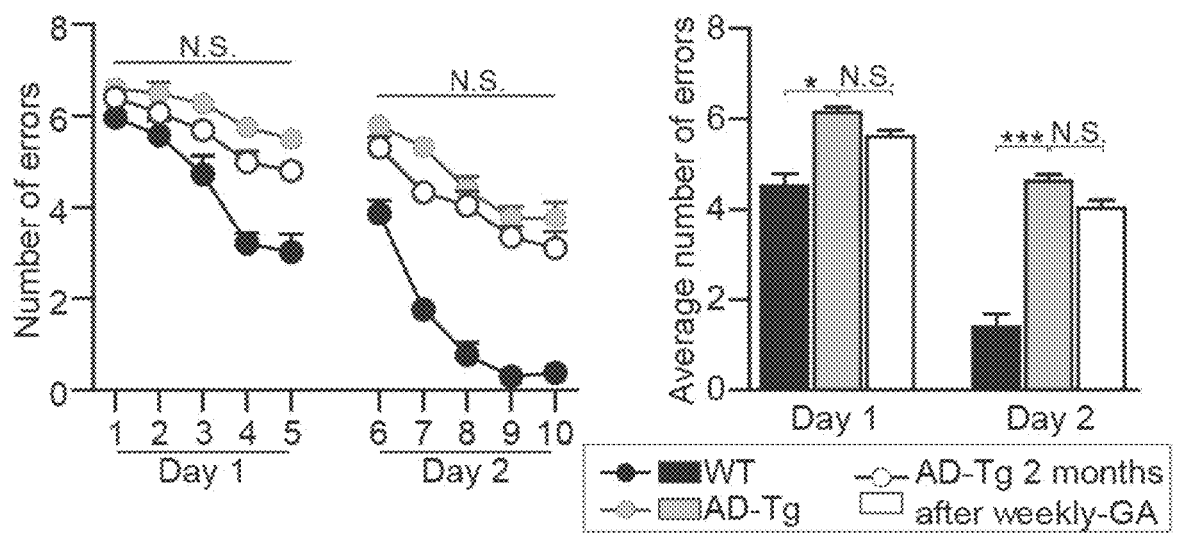
Figure 9A:
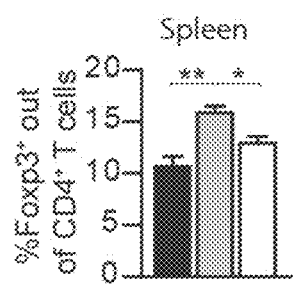
FIGS. 9A-H show further therapeutic effects of administration of weekly-GA in AD-Tg mice. A-B shows 5XFAD AD-Tg mice that were treated with either weekly-GA, or vehicle (PBS), and were examined at the end of the 1$^{st}$ week of the administration regimen (after a total of two GA injections). Flow cytometry analysis for CD4⁺Foxp3⁺ splenocyte frequencies (A), and CP IFN-γ-expressing immune cells (B; intracellularly stained and pre-gated on CD45), in treated 6-month old AD-Tg mice, compared to age-matched WT controls (n=4-6 per group; one-way ANOVA followed by Newman-Keuls post hoc analysis). (C) mRNA expression levels for the genes icam1, cxcl10 and ccl2, measured by RT-qPCR, in CPs of 4-month old AD-Tg mice, treated with either weekly-GA or vehicle, and examined either at the end of the 1$^{st}$ or 4$^{th}$ week of the weekly-GA regimen (n=6-8 per group; one-way ANOVA followed by Newman-Keuls post hoc analysis).
Figure 9B:
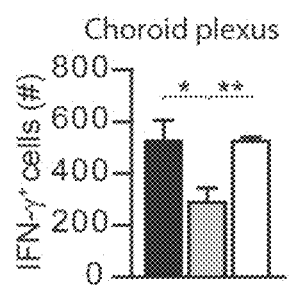
Figure 9C:
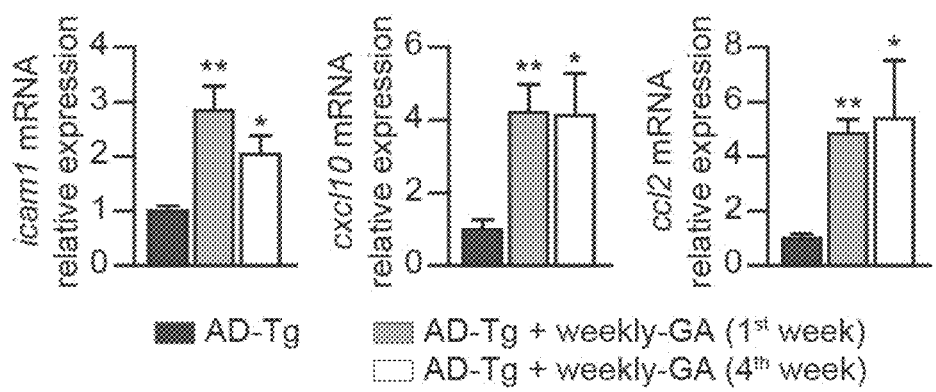

Weekly Administration of Copolymer-1 Reduces Treg-Mediated Systemic Immune Suppression, Improves CP Gateway Activity, and Mitigates AD Pathology To further substantiate the causal nature of the inverse relationship between systemic immune suppression, CP function and AD pathology, we next made use of the immunomodulatory compound, Glatiramer acetate (GA; also known as Copolymer-1, or Copaxone®), which in a weekly administration regimen was found to have a therapeutic effect in the APP/PS1 mouse model of AD (Butovsky et al, 2006); this effect was functionally associated with mo-MΦ recruitment to cerebral sites of disease pathology (Butovsky et al, 2007). Here, we first examined whether the CP in APP/PS1 AD-Tg mice, similarly to our observation in 5XFAD AD-Tg mice, is also deficient with respect to IFN-γ expression levels. We found that in APP/PS1 AD-Tg mice, IFN-γ levels at the CP were reduced relative to age-matched WT controls (FIG. 7A). These results encouraged us to test whether the therapeutic effect of weekly-GA in APP/PS1 mice (Butovsky et al, 2006), could be reproduced in 5XFAD AD-Tg mice, and if so, whether it would affect systemic Tregs, and activation of the CP for mo-MΦ trafficking. We therefore treated 5XFAD AD-Tg mice with a weekly administration regimen of GA over a period of 4 weeks (henceforth, "weekly-GA"; schematically depicted in FIG. 8A). We found that 5XFAD AD-Tg mice treated with weekly-GA, showed reduced neuroinflammation (FIG. 8B-D), and improved cognitive performance, which lasted up to 2 months after the treatment (FIG. 8E-I). Examining by flow cytometry the effect of weekly-GA on systemic immunity and on the CP, we found reduced splenocyte Foxp3$^+$ Treg levels (FIG. 9A), and an increase in IFN-γ-producing cells at the CP of the treated 5XFAD AD-Tg mice, reaching similar levels as those observed in WT controls (FIG. 9B). The elevated level of IFN-γ-expressing cells at the CP in the weekly-GA treated mice, was accompanied by upregulated epithelial expression of leukocyte trafficking molecules (FIG. 9C).

Figure 9D:
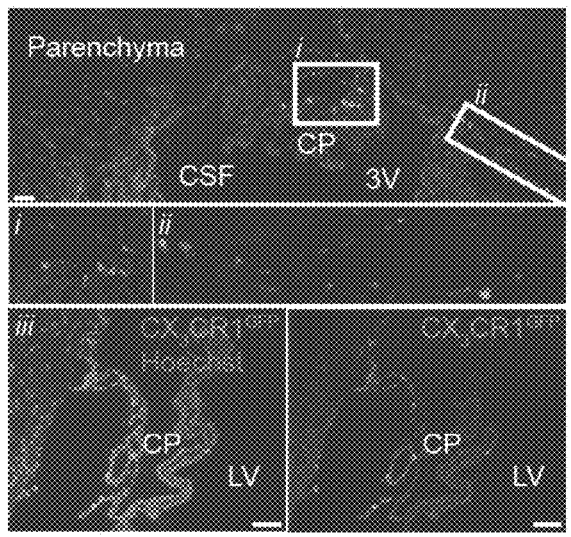
Figure 9E:
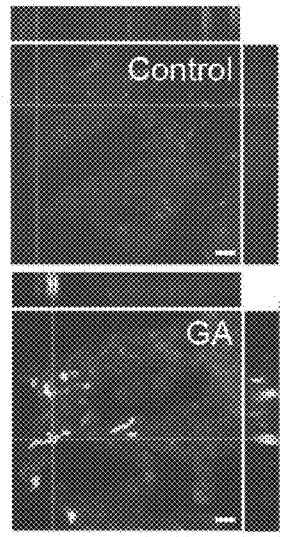
Figure 9F:
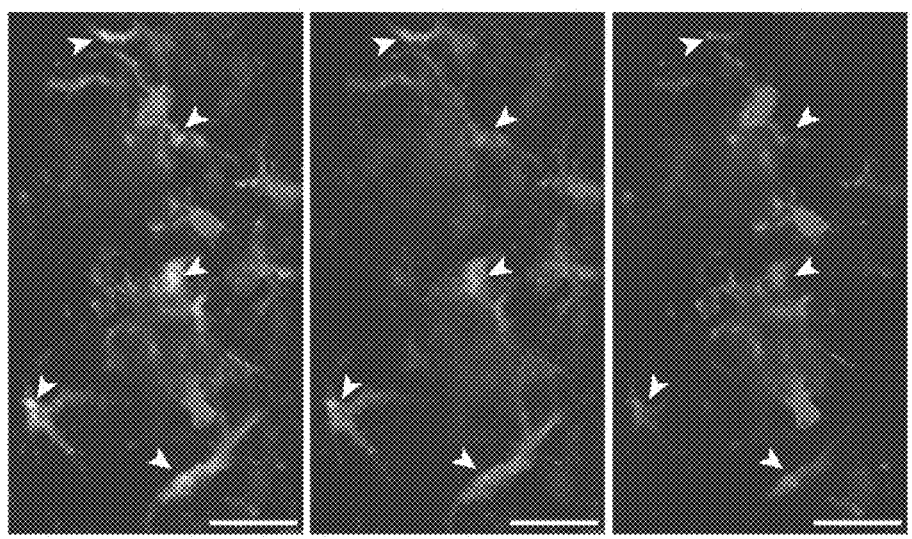
Figure 9G:
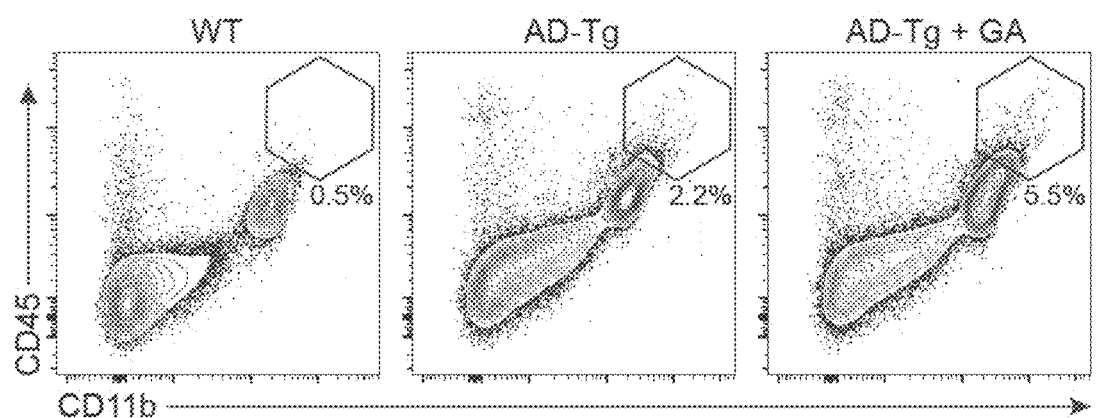
Figure 9H:
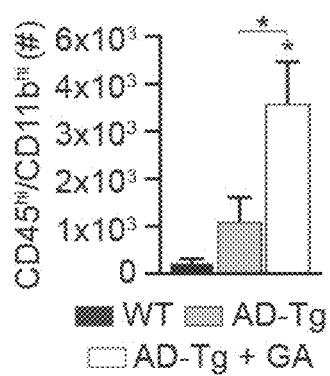

To detect infiltrating mo-MΦ entry to the CNS, we used 5XFAD AD-Tg/CX$_3$CR1$^{GFP/+}$ bone marrow (BM) chimeric mice (prepared using head protection), allowing the visualization of circulating (green fluorescent protein (GFP)$^+$ labeled) myeloid cells (Shechter et al, 2009; Shechter et al, 2013). We found increased homing of GFP$^+$ mo-MΦ to the CP and to the adjacent ventricular spaces following weekly-GA treatment, as compared to vehicle-treated AD-Tg/CX$_3$CR1$^{GFP/+}$ controls (FIG. 9D-E). Immunohistochemistry of the brain parenchyma revealed the presence of GFP$^+$ mo-MΦ accumulation at sites of cerebral plaque formation (FIG. 9F), and quantification of infiltrating myeloid cells, by flow cytometry analysis of the hippocampus in AD-Tg non-chimeric mice, showed increased numbers of CD11b$^{high}$CD45$^{high}$-expressing cells (FIG. 9G, H). Together, these results substantiated the functional linkage between mo-MΦ recruitment to sites of AD pathology, reduction of systemic Treg levels and IFN-γ-dependent activation of the CP.

Example 4

Figure 10A:
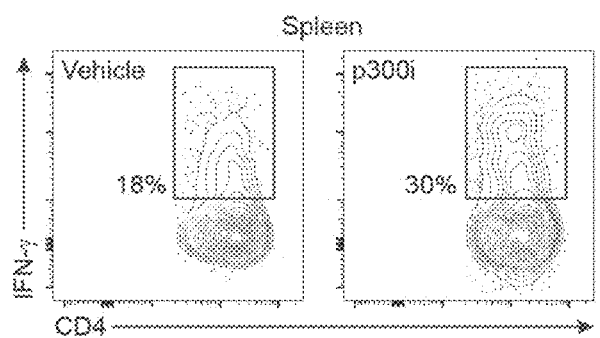
FIGS. 10A-H depict the therapeutic effect of administration of a p300 inhibitor (C646) in AD-Tg mice.
Figure 10B:
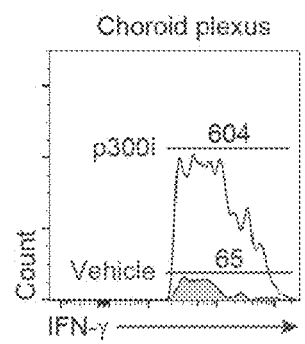
Figure 10C:
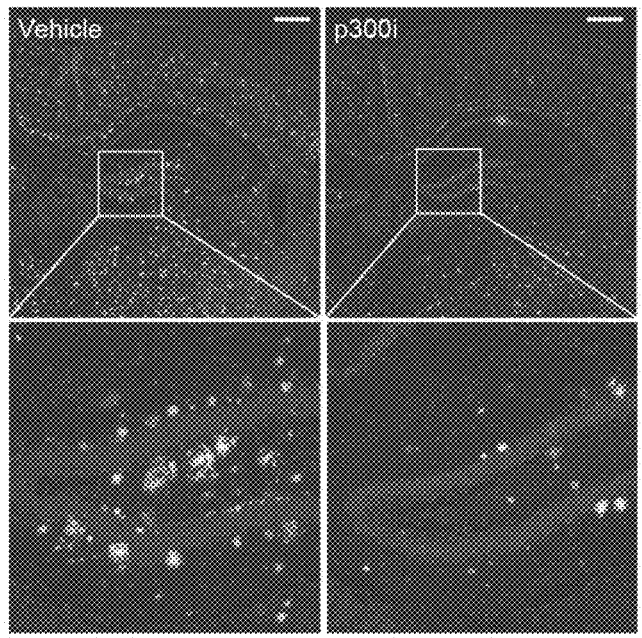
Figure 10D:
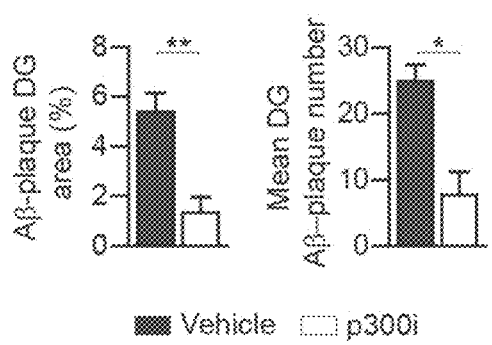
Figure 10E:
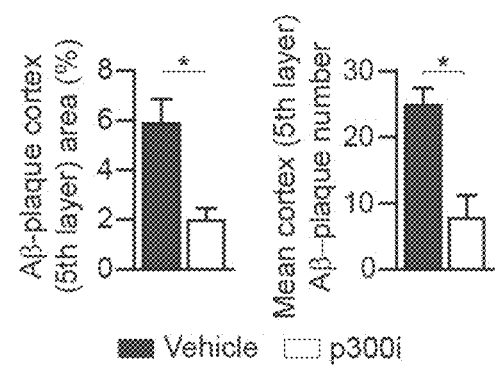
Figure 10F:
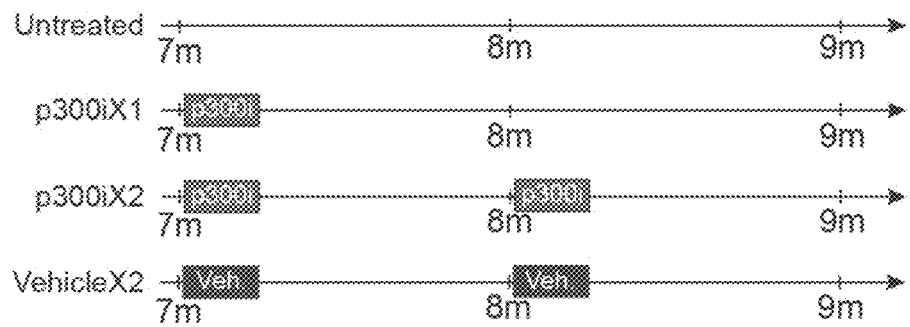
Figure 10G:
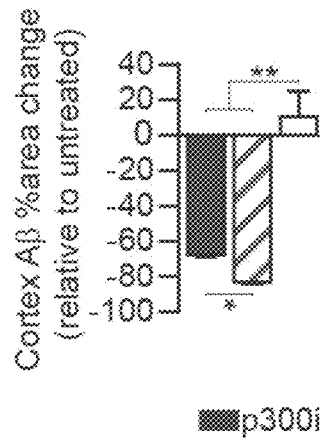
Figure 10H:
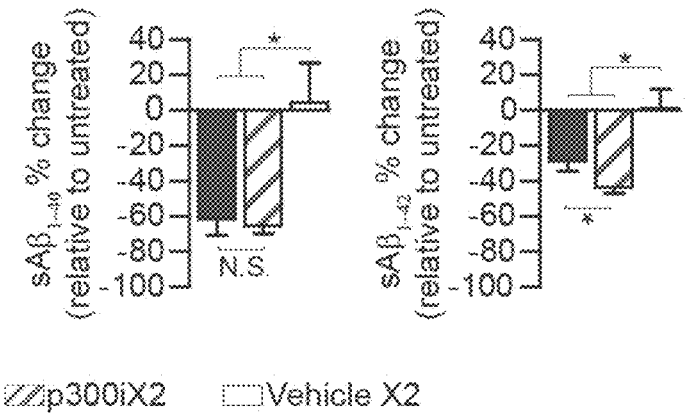

Interference with Treg Activity Using a Small Molecule Histone Acetyltransferase Inhibitor The findings above, which suggested that Treg-mediated systemic immune suppression interferes with the ability to fight AD pathology, are reminiscent of the function attributed to Tregs in cancer immunotherapy, in which these cells hinder the ability of the immune system to mount an effective anti-tumor response (Bos & Rudensky, 2012; Nishikawa & Sakaguchi, 2010). Therefore, we considered that a treatment that directly interferes with Foxp3+ Treg cell activity might be advantageous in AD. We tested p300i (C646 (Bowers et al, 2010)), a nonpeptidic inhibitor of p300, a histone acetyltransferase that regulates Treg function (Liu et al, 2013); this inhibitor was shown to affect Treg suppressive activities while leaving protective T effector cell responses intact (Liu et al, 2013). We found that mice treated with p300i, compared to vehicle (DMSO) treated controls, showed elevated levels of systemic IFN-γ-expressing cells in the spleen (FIG. 10A), as well as in the CP (FIG. 10B). We next treated AD-Tg mice with either p300i or vehicle over the course of 1 week, and examined the animals 3 weeks later for cerebral Aβ plaque burden. Immunohistochemical analysis revealed a significant reduction in cerebral Aβ plaque load in the p300i treated AD-Tg mice (FIG. 10C-E). We also tested whether the effect on plaque pathology following one course of treatment would last beyond the 3 weeks, and if so, whether additional courses of treatment would contribute to a long-lasting effect. We therefore compared AD-Tg mice that received a single course of p300i treatment and were examined 2 month later, to an age-matched group that received two courses of treatments during this period, with a 1-month interval in between (schematically depicted in FIG. 10F). We found that the reduction of cerebral plaque load was evident even two months after a single course of treatment, but was stronger in mice that received two courses of treatments with a 1-month interval in between (FIG. 10G). Since impaired synaptic plasticity and memory in AD is associated with elevated cerebral levels of soluble $A\beta_{1-40}/A\beta_{1-42}$ (sAβ) levels (Shankar et al, 2008), we also measured sAβ levels following a single or repeated cycles of p300i treatment. Again, we found that both one and two courses (with an interval of 1 month in between) were effective in reducing cerebral sAβ, yet this effect was stronger following repeated courses with respect to the effect on $sA\beta_{1-42}$ (FIG. 10H). These results indicated that while a single short-term course of treatment is effective, repeated courses of treatments would be advantageous to maintain a long-lasting therapeutic effect, similar to our observations following weekly-GA treatment.

Example 5

Figure 11A:
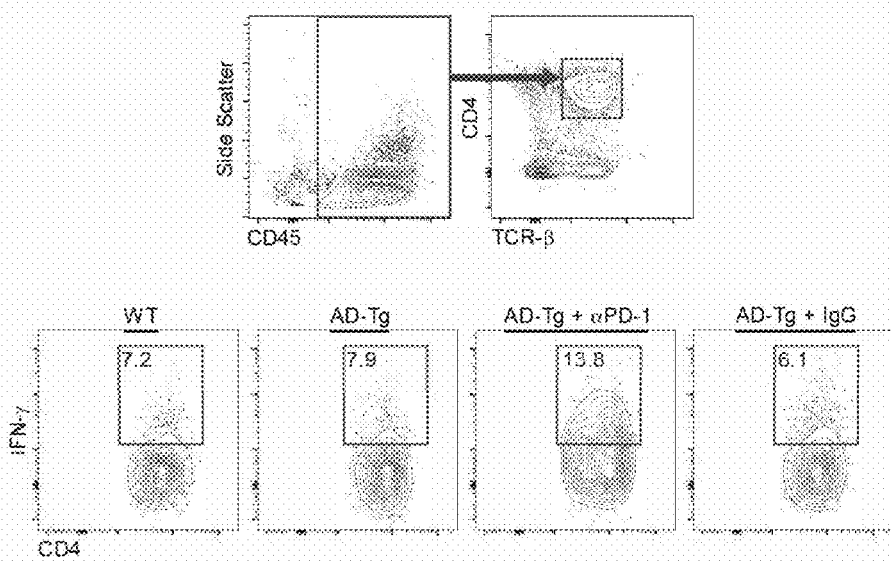
FIGS. 11 A-D show that PD-1 blockade augments percentage of IFN-γ-producing CD4+ T-cells in the spleen, as well as IFN-γ expression at the choroid plexus in AD-Tg mice. 10-month old AD-Tg mice were i.p. injected on day 1 and day 4 with 250 ug of either anti-PD-1 or control IgG, and examined at days 7-10 for the effect on the systemic immune response and CP activity. (A-B) Representative flow cytometry plots (A), and quantitative analysis (B), of CD4+IFN-γ+ splenocyte frequencies (intracellularly stained and pre-gated on CD45 and TCR-β), in anti-PD-1 or IgG treated AD-Tg mice, and untreated AD-Tg and WT controls (n=4-6 per group; one-way ANOVA followed by Newman-Keuls post hoc analysis; **, $P<0.01$ between the indicted treated groups; error bars represent mean±s.e.m.). (C) mRNA expression levels of ifn-g, measured by RT-qPCR in the CP of AD-Tg mice treated with anti-PD-1 when compared to IgG treated and untreated AD-Tg controls (D) GO annotation terms enriched in RNA-Seq in CPs of the same mice (n=3-5 per group; one-way ANOVA followed by Newman-Keuls post hoc analysis; *, $P<0.05$) (gray scale corresponds to negative log-base 10 of P-value).
Figure 11B:
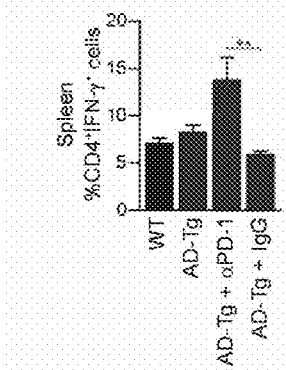

Therapeutic Potential of PD-1 Immune Checkpoint Blockade in Alzheimer's Disease We first tested whether targeting the PD-1 inhibitory pathway could affect IFN-γ-associated systemic immunity in 5XFAD AD transgenic (AD-Tg) mice, which co-expresses five mutations associated with familial AD (Oakley et al, 2006). AD-Tg mice at the age of 10 months, a time point at which cerebral pathology is advanced, were administrated with two intraperitoneal (i.p.) injections of either blocking antibodies directed at PD-1 (anti-PD-1) or IgG control antibodies, on days 1 and 4, and then examined on day 7. Flow cytometry analysis revealed that blockade of the PD-1 pathway resulted in elevated frequencies of IFN-γ-producing CD4+ T splenocytes (FIG. 11A, B).

TABLE 3

GO annotation, related to FIG. 11.

| GO term | Description | P-value | FDR q-value |
|---|---|---|---|
| GO:0034341 | response to interferon-gamma | 2.13E−14 | 2.30E−10 |
| GO:0048002 | antigen processing and presentation of peptide antigen | 3.05E−10 | 1.65E−06 |
| GO:0019886 | antigen processing and presentation of exogenous peptide antigen via MHC class II | 4.11E−10 | 1.48E−06 |
| GO:0002478 | antigen processing and presentation of exogenous peptide antigen | 5.26E−10 | 1.42E−06 |
| GO:0034097 | response to cytokine | 5.67E−10 | 1.22E−06 |
| GO:0002504 | antigen processing and presentation of peptide or polysaccharide antigen via MHC class II | 1.04E−09 | 1.87E−06 |
| GO:0002495 | antigen processing and presentation of peptide antigen via MHC class II | 1.04E−09 | 1.60E−06 |
| GO:0019884 | antigen processing and presentation of exogenous antigen | 5.82E−09 | 7.86E−06 |
| GO:0019882 | antigen processing and presentation | 1.43E−07 | 1.71E−04 |
| GO:0035456 | response to interferon-beta | 6.67E−07 | 7.20E−04 |
| GO:0006955 | immune response | 1.07E−06 | 1.05E−03 |
| GO:0002819 | regulation of adaptive immune response | 1.92E−06 | 1.73E−03 |
| GO:0071345 | cellular response to cytokine stimulus | 2.21E−06 | 1.84E−03 |
| GO:0071346 | cellular response to interferon-gamma | 2.21E−06 | 1.71E−03 |

Gene ontology terms enriched in the CP of AD-Tg mice treated with anti-PD-1, when compared to IgG treated and untreated AD-Tg controls. Log 10 values of all RNA sequences of the CP were ranked according to their differential expression levels and analyzed.

Figure 11C:
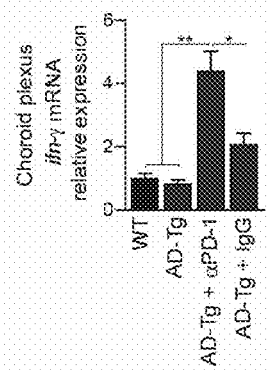
Figure 11D:
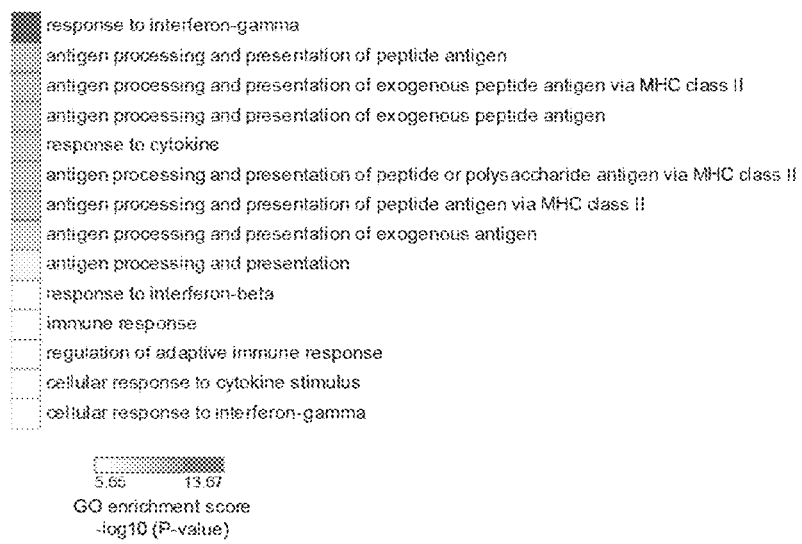

We next examined whether this systemic immune response affected the CP activity. Genome wide RNA-sequencing of the CP (Not shown; the full analysis will be disclosed in a report by the present inventors having the title of Example 5 and it can be obtained from the inventors upon request) showed an expression profile associated with response to IFN-γ (FIG. 11D and Table 3), and real-time quantitative PCR (RT-qPCR) verified elevated IFN-γ mRNA levels at the CP, when compared to IgG-treated or untreated AD-Tg controls (FIG. 11C). These findings confirmed a systemic, and CP tissue-specific, IFN-γ immune response following PD-1 blockade, and encouraged us to next test the effect on disease pathology.

To examine the functional impact of PD-1 blockade on AD pathology, we treated 10-month old AD-Tg mice with either anti-PD-1 or IgG control antibodies, and evaluated the effect on spatial learning and memory performance, using the radial arm water maze (RAWM) task.

One month following treatment (two i.p. injections with 3-day interval), anti-PD1 treated AD-Tg mice exhibited a significant improvement in cognitive function relative to IgG-treated or untreated age-matched controls, reaching cognitive levels similar to that of age-matched WT mice (FIG. 12A). We next tested whether the benefit of PD-1 blockade on cognitive performance in AD-Tg mice would last beyond 1 month, and whether additional therapeutic sessions would be advantageous. We treated AD-Tg mice with anti-PD-1 at the age of 10 months ("1 session") or at both 10 and 11 months of age ("2 sessions"), and examined the outcome on cognitive performance at the age of 12 months (schematically depicted in FIG. 12B). Control groups included WT mice, untreated AD-Tg mice, and AD-Tg mice that received two sessions of IgG treatment. We found that while a single session of anti-PD-1 administration had a beneficial effect on spatial learning and memory 1 month following the treatment (FIG. 12A), no significant effect could be detected in mice that received a single session of treatment and were tested 2 months later (FIG. 12B). In contrast, AD-Tg mice that received two sessions of anti-PD-1, at a 1-month interval, displayed cognitive performance similar to that of WT mice, at the end of the 2-month timeframe (FIG. 12B).

Figure 13A:
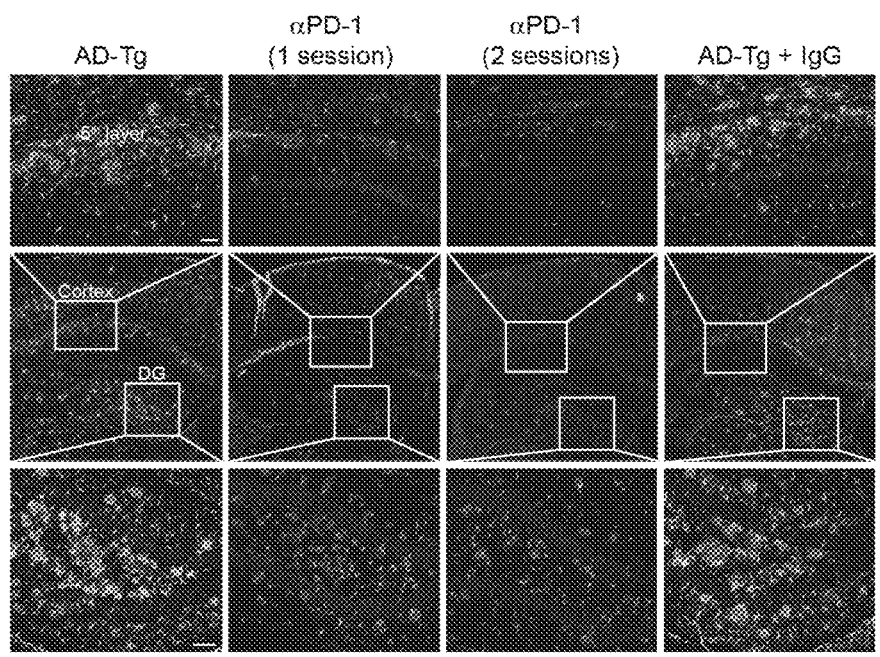
FIGS. 13A-D depict representative microscopic images showing that PD-1 blockade mitigates AD pathology (A), and quantitative analyses (B, C, D), of Aβ plaque burden and astrogliosis in the brains of AD-Tg mice, which were treated at the age of 10-months with either anti-PD-1 (in 1 or 2 sessions, as depicted in FIG. 12A-B) or IgG control, and subsequently examined at the age of 12 months. Brains were immunostained for Aβ plaques (in red), GFAP (marking astrogliosis, in green), and by Hoechst nuclear staining (n=4-5 per group; Scale bar, 50 μm). Mean Aβ plaque area and plaque numbers were quantified in the hippocampal dentate gyrus (DG) and the 5$^{th}$ layer of the cerebral cortex, and GFAP immunoreactivity was measured in the hippocampus (in 6 μm brain slices; n=5-6 per group; Student's t test). In all panels, error bars represent mean±s.e.m.; *, $P<0.05$; , $P<0.01$; *, $P<0.001$.
Figure 13B:
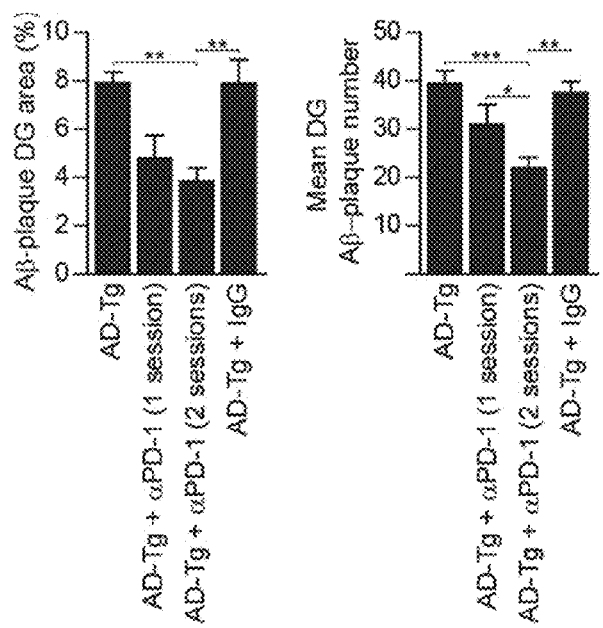
Figure 13C:
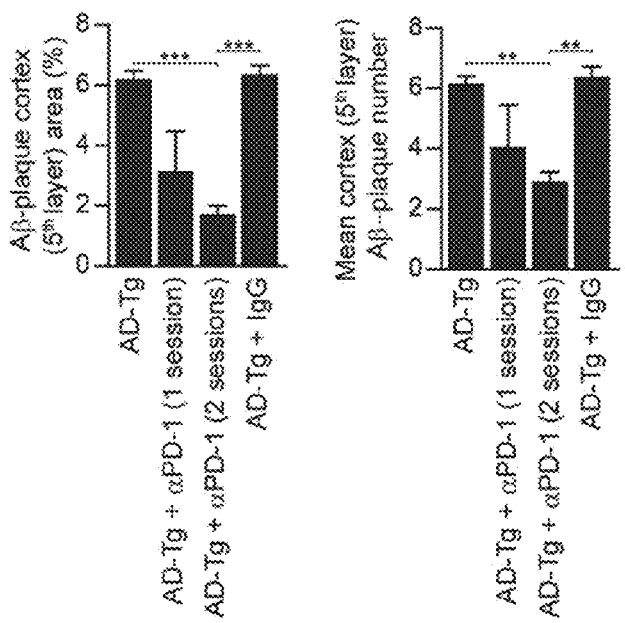
Figure 13D:
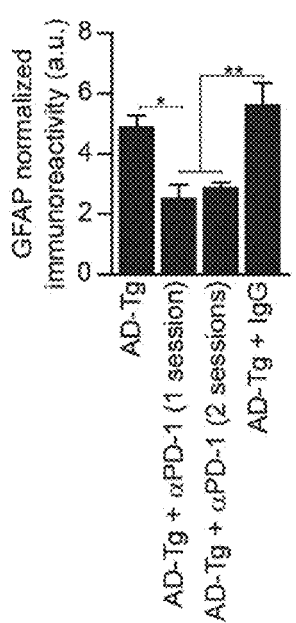

We examined whether PD-1 blockade affected AD pathology as manifested by cerebral Aβ plaque load and gliosis. Brains of AD-Tg mice that received anti-PD-1 or IgG in either one or two sessions were examined by immunohistochemistry for Aβ and glial fibrillary acid protein (GFAP). We found that cerebral Aβ plaque burden was reduced in the hippocampal dentate gyrus (FIG. 13A, B), and the cerebral cortex (5th layer) (FIG. 13A, C), two brain regions exhibiting robust Aβ plaque pathology in 5XFAD mice (Oakley et al, 2006). The effect on Aβ clearance was evident following a single session of anti-PD-1 administration, and was more robust following two sessions. Quantitative analysis of GFAP immunostaining showed reduced hippocampal astrogliosis in both AD-Tg mice treated with 1 session, and those treated with 2 sessions of PD-1 blockade, relative to IgG-treated controls (FIG. 13A, D).

Figure 14:
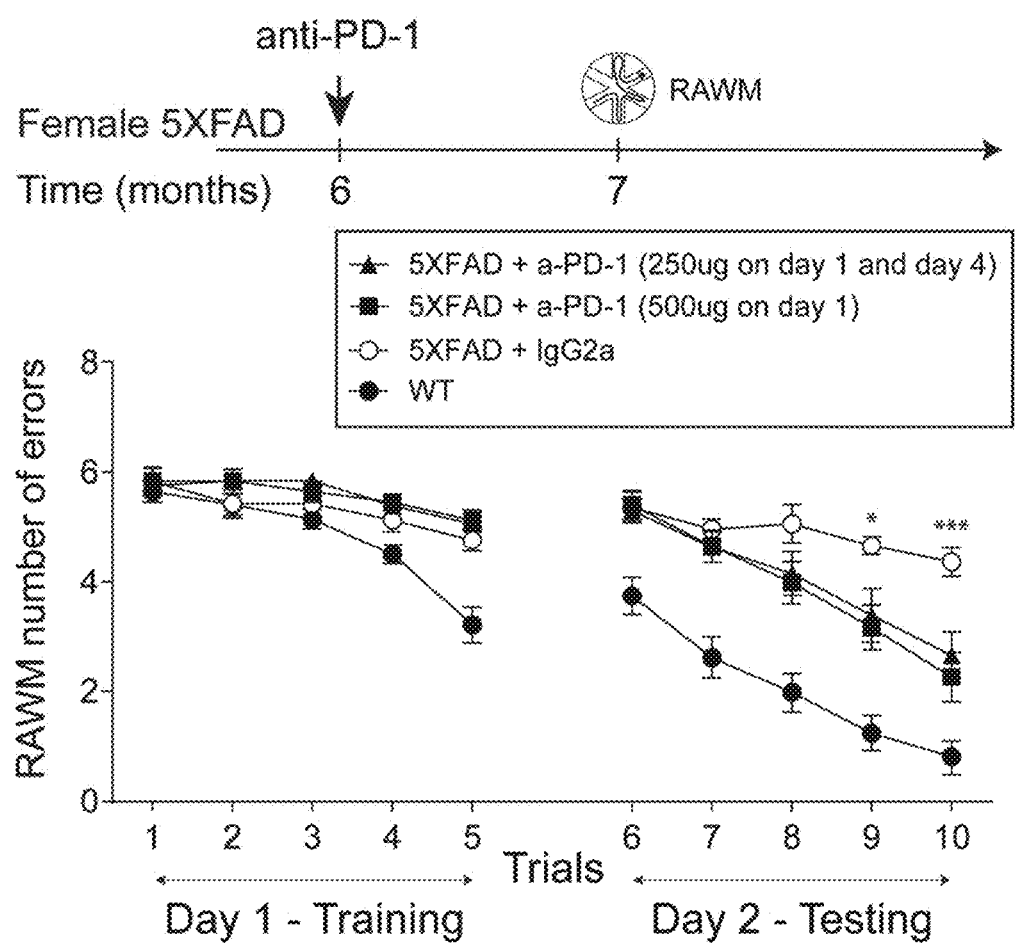
FIG. 14 shows the effect of different dosing and frequency of administration of anti-PD-1 antibody on cognitive decline in AD-Tg mice and illustrates the dosage scheme and the effect of anti-PD-1 antibody treatment on spatial learning and memory performance using the radial arm water maze (RAWM) task at 7 months of age. Black arrows indicate time points of treatment, and illustrations indicate time points of cognitive testing.

To investigate the effect of dosage and frequency of administration, female 5XFAD AD transgenic mice (average cohorts age of 6 months) were treated with either anti-PD-1-specific antibody (IgG2a anti-mouse PD-1 or IgG control (Rat IgG2a). Anti-PD-1-treated mice received either 1 injection of 500 ug of antibody on day 1 of the experiment, or two injections of 250 ug with a 3-day interval between injections. Aged matched wild-type (WT) mice were used as additional control group. Treatment effect on spatial learning and memory performance of anti-PD-1-treated 5XFAD mice—one injection (n=7) or two injections (n=11), IgG2a-treated 5XFAD mice (n=10), and WT (n=14) controls was evaluated using the radial arm water maze (RAWM) task at the age of 7 months (FIG. 14). Black arrows indicate time points of treatment, and illustrations indicate time points of cognitive testing. Repeated-measures were analyzed using two-way ANOVA and Dunnett post-test. Error bars represent mean±s.e.m.; *$P<0.05$, $P<0.01$, *$P<0.001$, anti-PD-1-treated (1 injection) versus IgG-treated controls. One month following treatment (two i.p. injections with 3-day interval), anti-PD1 treated AD-Tg mice exhibited a significant improvement in cognitive function relative to IgG-treated or untreated age-matched controls, reaching cognitive levels similar to that of age-matched WT mice (FIG. 14).

Figure 15A:
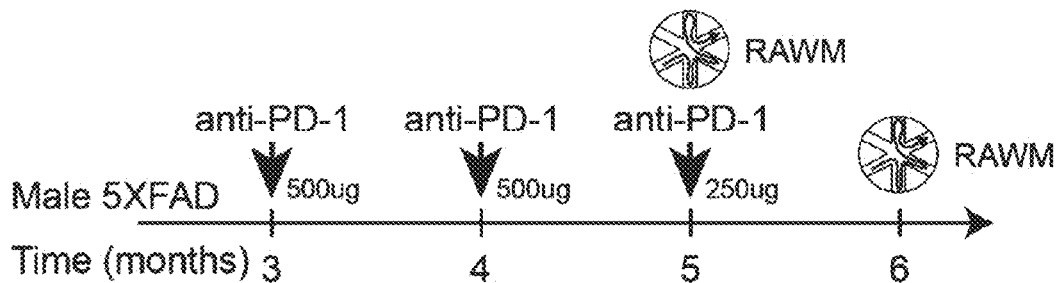
FIGS. 15A-C show the effect of repeated administration of anti-PD-1 antibody on cognitive decline in AD-Tg mice with (A) showing dosage scheme of a single injection followed by 4 weeks of non-treatment interval; (B) showing the effect of anti-PD-1 antibody treatment on spatial learning and memory performance using the radial arm water maze (RAWM) task at 5 months of age; and (C) showing anti-PD-1 antibody effect on spatial learning and memory performance using the radial arm water maze (RAWM) task at 6 months of age.
Figure 15B:
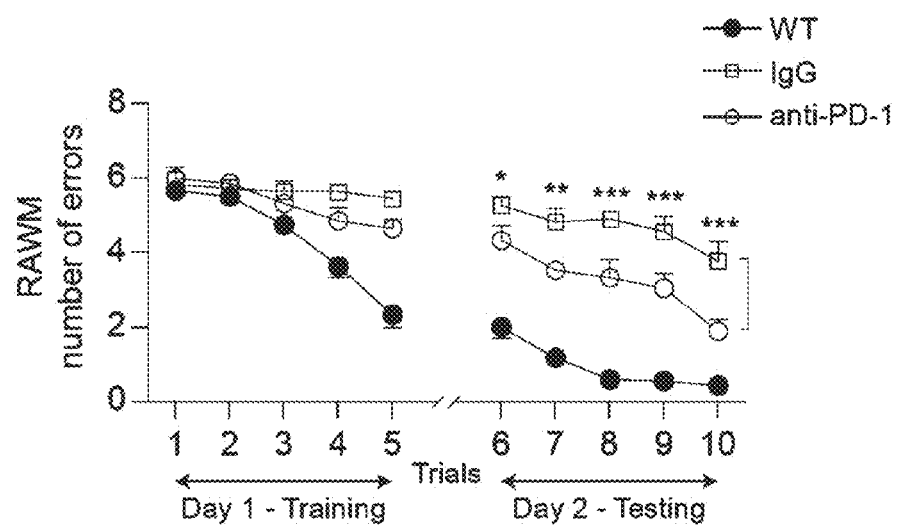
Figure 15C:
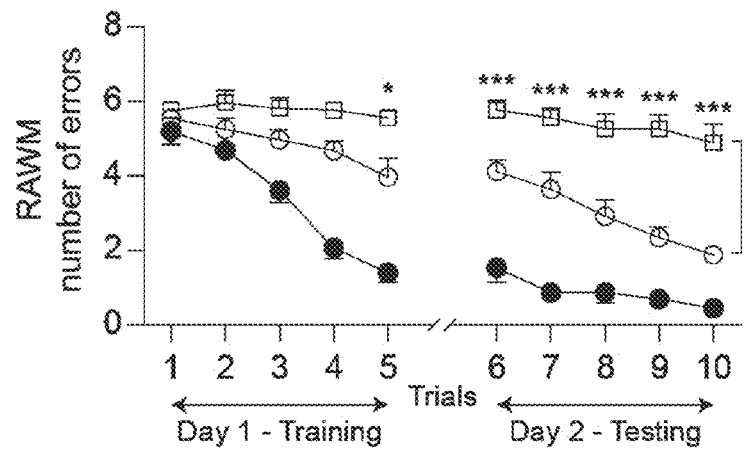

Finally, male 5XFAD AD transgenic mice were treated in a repeated treatment session, once a month, with either anti-PD-1-specific antibody (IgG2a anti-mouse PD-1) or IgG control (Rat IgG2a). The first injection was at the age of 3 months, the second at the age of 4 months, and the third at the age of 5 months. Dosage is indicated in the scheme of the experimental design (FIG. 15A). Aged matched wild-type (WT) mice were used as additional control group. Treatment effect on spatial learning and memory performance was evaluated using the radial arm water maze (RAWM) task, at two different time points—the age of 5 months (FIG. 15B), and the age of 6 months (FIG. 15C). Black arrows indicate time points of treatment, and illustrations indicate time points of cognitive testing. RAWM performance of anti-PD-1-treated 5XFAD mice (n=7), IgG2a-treated 5XFAD mice (n=9), and WT (n=8) controls. Repeated-measures were analyzed using two-way ANOVA and Dunnett post-test. Error bars represent mean±s.e.m.; *$P<0.05$, $P<0.01$, *$P<0.001$, anti-PD-1-treated versus IgG-treated controls. These findings demonstrate that repeated sessions of treatment with PD-1 blockade, could not only reverse disease progression when given to 5XFAD mice at advanced stages of disease, but also delay disease onset when the treatment commences at an early age, prior to cognitive decline (FIGS. 15B-C).

Example 6

Therapeutic Potential of TIM-3 Immune Checkpoint Blockade in Alzheimer's Disease To examine the functional impact of TIM-3 blockade on AD pathology, we treated 6-month old female 5XFAD AD-Tg mice with either anti-TIM-3-specific antibody (anti-mouse TIM-3) or IgG control (Rat IgG2a antibody). Dosage is indicated in the scheme of the experimental design (FIG. 16). The treatment was consistent of two i.p. injections of the antibody, 250 μg each, with a 3-day interval between injections. Aged matched wild-type (WT) mice were used as additional control group. Treatment effect on spatial learning and memory performance of anti-TIM-3-treated 5XFAD mice (n=9), of IgG-treated (n=6) 5XFAD mice and WT (n=7) controls was evaluated using the radial arm water maze (RAWM) task at the age of 7 months (FIG. 16). Black arrows indicate time points of treatment, and illustrations indicate time points of cognitive testing. Repeated-measures were analyzed using two-way ANOVA and Dunnett post-test. Error bars represent mean±s.e.m.; * $P<0.05$, $P<0.01$, *$P<0.001$, anti-TIM-3-treated versus IgG-treated controls. One month following treatment, anti-TIM-3-treated AD-Tg mice exhibited a significant improvement in cognitive performance relative to IgG-treated 5XFAD mice, or aged-matched WT controls (FIG. 16).

Example 7

Figure 17A:
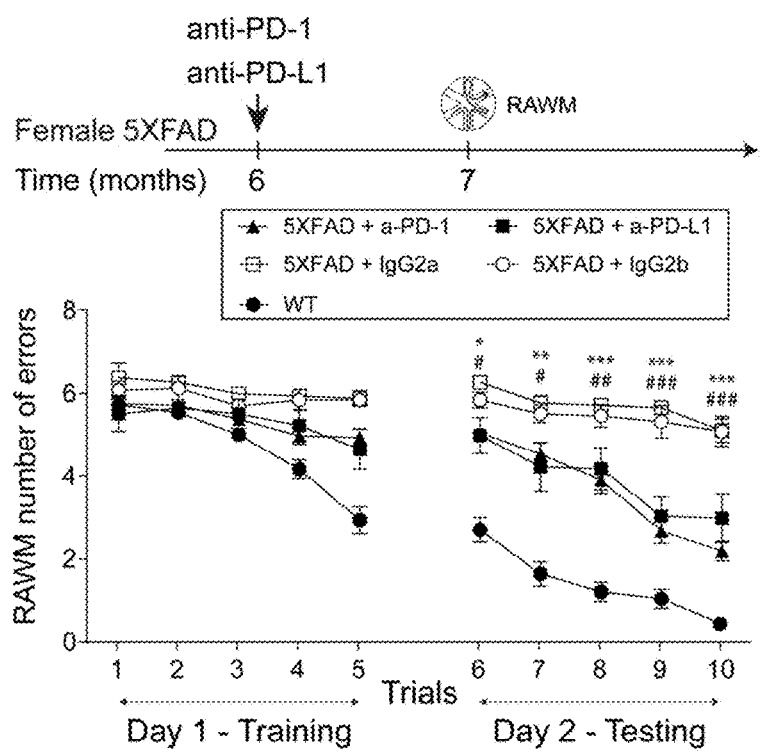
FIG. 17A-B PD-L1 blockade mitigates cognitive decline in AD-Tg mice with (A) showing the effect of a single administration of anti-PD-L1 antibody on cognitive decline in AD-Tg mice and illustrates the dosage scheme and the effect of anti-PD-L1 antibody treatment on spatial learning and memory performance using the radial arm water maze (RAWM) task at 7 months of age; black arrows indicate time points of treatment, and illustrations indicate time points of cognitive testing; and (B) showing Aβ-plaque load in the cortex of anti-PD-1 treated animals and anti-PD-L1-treated animals compared to control animals.

Therapeutic Potential of PD-L1 Immune Checkpoint Blockade in Alzheimer's Disease, and Comparison to Anti-PD-1 Treatment To examine the functional impact of PD-L1 immune checkpoint blockade on AD pathology, and to compare it to the effect of the same dose and regimen of anti-PD-1 blockade, we treated female 5XFAD AD transgenic mice (average cohorts age of 6 months) with either anti-PD-1-specific antibody (IgG2a rat anti-mouse PD-1), anti-PD-L1-specific antibody (IgG2b anti-mouse PD-L1), or IgG control (either Rat IgG2a or IgG2b). Dosage is indicated in the scheme of the experimental design (FIG. 17A). Aged matched wild-type (WT) mice were used as additional control group. Treatment effect on spatial learning and memory performance of anti-PD-1-treated 5XFAD mice (n=9), anti-PD-L1-treated 5XFAD mice (n=7), IgG2a-treated 5XFAD mice (n=6), IgG2b-treated 5XFAD mice (n=7) and WT (n=16) controls was evaluated using the radial arm water maze (RAWM) task at the age of 7 months (FIG. 17A). Black arrows indicate time points of treatment, and illustrations indicate time points of cognitive testing. Repeated-measures were analyzed using one-way ANOVA and Dunnett post-test. Error bars represent mean±s.e.m.; * $P<0.05$, $P<0.01$, *$P<0.001$, anti-PD-1-treated versus IgG-treated controls. #$P<0.05$, ##$P<0.01$, ###$P<0.001$, anti- PD-L1-treated versus IgG-treated controls. One month following treatment, anti-PD-L1 and anti-PD-1-treated AD-Tg mice were examined for their cognitive performance and were compared to IgG-treated AD-Tg mice (negative control). Wild type mice were also assessed cognitively in this experiment, and were used as a positive control for cognitive performance. Both anti-PD-L1 and anti-PD-1-treated AD-Tg mice exhibited a similar and significant improvement in cognitive performance relative to IgG-treated 5XFAD mice (FIG. 17A).

Figure 17B:
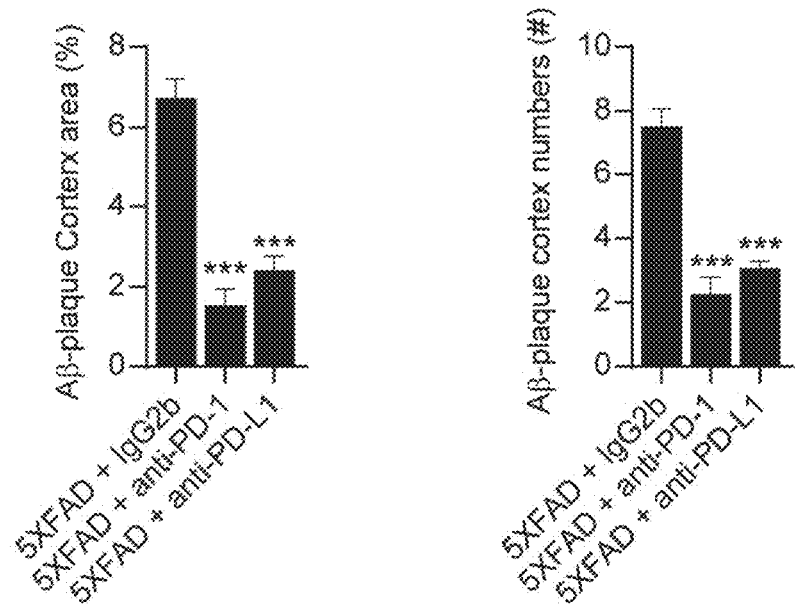

Following the RAWM test, mice were sacrificed, and their brains were collected for fixation and histology/immunohistctocimical analysis. Mean plaque area and numbers were quantified (in 6-μm brain slices) in the 5th layer of the cerebral cortex, showing plaque load reduction in both treatment group (anti-PD-1 and anti-PD-L1). This analysis showed that both anti-PD-1 and anti-PD-L1 treated animals showed a statistically significant decrease in Aβ-plaque formation in the cortex (FIG. 17B)

Figure 18A:
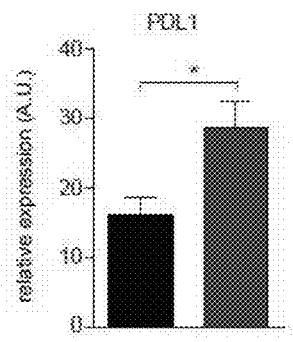
FIG. 18A-B show that PD-L1 expression increases at the CP with aging with (A) showing expression of PDL1 in the CP of young (left bar) and aged (right bar) mice, measured by RT-qPCR; and (B) showing immunohistochemical staining of epithelial expression of PD-L1 at the CP of young (left micrograph) and aged (right micrograph) mice. LV; lateral ventricle.
Figure 18B:
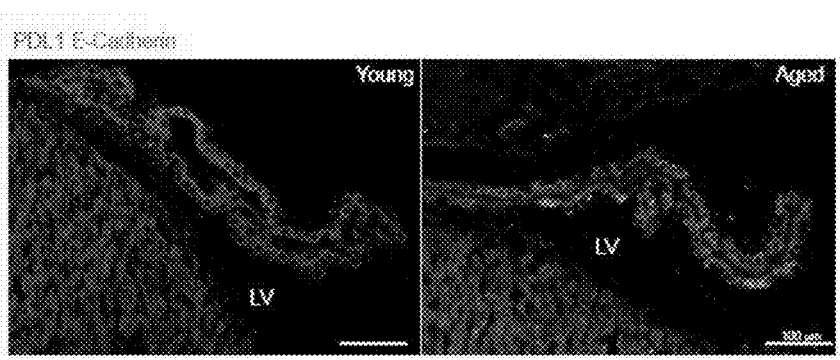

PD-L1 is expressed by activated immune cells such as T cells, B cells, macrophages, dendritic cells and microglia, as well as by non-immune cells such as endothelial and epithelial cells. Thus, we envisioned that the expression of PD-L1 by the CP epithelium might contribute to the down regulation of the trafficking of leukocytes to the CNS, by dampening the activity of IFN-γ producing T-cells which express PD-1 upon communication with PD-L1-expressing epithelial cells within the CP. Immunohistochemical analysis shows that in aged mice the CP epithelium expressed significantly higher levels of PD-L1, compared to young mice (FIG. 18).

Example 8

Therapeutic Potential of Immune Checkpoint Blockade in Alzheimer's Disease

To teste whether blockade of immune checkpoints could attenuate AD pathology, AD-Tg mice are treated at ages between 6 to 10-month old with one of the following anti-checkpoint antibodies: anti-ICOS, anti-B7RP1, anti-VISTA, anti-CD40, anti-CD40L, anti-CD80, anti-CD86, anti-B7-H3, anti-B7-H4, B7-H7, anti-BTLA, anti-HVEM, anti-CD137, anti-CD137L, anti-OX40L, anti-CD-27, anti-CD70, anti-STING, anti-TIGIT antibody or anti-GITR antibody. Some mice are treated with anti-PD-1 antibody as positive control, IgG control as negative control or combinations of anti-PD1 and one of the other anti-checkpoint antibodies mentioned above. Treatment effect on spatial learning and memory performance, using the radial arm water maze (RAWM) task, Aβ plaque burden by immunohistochemistry for Aβ and hippocampal astrogliosis by immunohistochemistry for glial fibrillary acid protein (GFAP) will be measured one month following treatment.

It is expected that the mice treated with the antibodies display significant cognitive improvement in comparison to IgG-treated and untreated AD-Tg mice as well as a significant reduction of cerebral plaque load.

Example 9

Therapeutic Potential of PD-1 in Combination with CTLA-4 Immune Checkpoint Blockade in Alzheimer's Disease At 10 months of age, 5XFAD Alzheimer's' disease (AD) transgenic (Tg) mice are injected i.p. with either 250 μg of anti-PD1 (RMP1-14; #BE0146; Bioxcell Lifesciences Pvt. LTD.) and 250 μg anti-CTLA-4 (InVivoMAb anti-mCD152; #BE0131; Bioxcell Lifesciences Pvt. LTD.) or control IgG (IgG2a, #BE0089 or Polyclonal Syrian Hamster IgG, #BE0087; Bioxcell Lifesciences Pvt. LTD.) antibodies, on day 1 and day 4 of the experiment, and are examined 3 weeks after for their cognitive performance by radial arm water maze (RAWM) spatial learning and memory task, as described above.

Some mice receive an additional treatment session with an interval session of 3 weeks. Control groups are either treated with IgG or untreated, and all groups of mice are tested for their cognitive performance 3 weeks later.

It is expected that the mice treated with the combination of antibodies display significant cognitive improvement in comparison to IgG-treated and untreated AD-Tg mice as well as a significant reduction of cerebral plaque load.

Example 10

Therapeutic Potential of Immune Checkpoint Blockade Approach in PTSD Pathology

Severely stressful conditions or chronic stress can lead to posttraumatic stress disorder (PTSD) and depression. We adopted a physiological PTSD-like animal model in which the mice exhibit hypervigilant behavior, impaired attention, increased risk assessment, and poor sleep (Lebow et al, 2012). In this experimental model of PTSD induction, mice are habituated for 10 days to a reverse day/night cycle, inflicted with two episodes of electrical shocks (the trauma and the trigger), referred to as a "PTSD induction", and evaluated at different time points subsequent to trauma. Following the traumatic event mice are injected with said compound which blocks immune checkpoints. The mice are treated according to one of the following regimens:

The mice are treated with one of the following anti-checkpoint antibodies: anti-ICOS, anti-B7RP1, anti-VISTA, anti-CD40, anti-CD40L, anti-CD80, anti-CD86, anti-B7-H3, anti-B7-H4, B7-H7, anti-BTLA, anti-HVEM, anti-CD137, anti-CD137L, anti-OX40L, anti-CD-27, anti-CD70, anti-STING, anti-GITR or anti-TIGIT antibody alone or in combination with an anti-CTLA-4 antibody. Some mice are treated with anti-PD-1 antibody as positive control, IgG control as negative control or combinations of anti-PD1 and one of the other anti-checkpoint antibodies mentioned above.

Some mice receive an additional treatment session with an appropriate interval session.

It is expected that mice that receive the treatment do not display anxiety behavior associated with PTSD in this experimental model, as assessed by time spent exploring and risk assessing in dark/light maze or the other behavioral tasks described in (Lebow et al, 2012).

Example 11

Therapeutic Potential of Immune Checkpoint Blockade Approach in Parkinson's Disease Pathology Parkinson disease (PD) transgenic (Tg) mice or the MPTP-induced mouse models of PD are used in these experiment. The mice are treated at the progressive stages of disease according to one of the following regimens:

PD-Tg mice are treated with one of the following anti-checkpoint antibodies: anti-ICOS, anti-B7RP1, anti-VISTA, anti-CD40, anti-CD40L, anti-CD80, anti-CD86, anti-B7-H3, anti-B7-H4, B7-H7, anti-BTLA, anti-HVEM, anti-CD137, anti-CD137L, anti-OX40L, anti-CD-27, anti-CD70, anti-STING, anti-GITR or anti-TIGIT antibody alone or in combination with an anti-CTLA-4 antibody. Some mice are treated with anti-PD-1 antibody as positive control, IgG control as negative control or combinations of anti-PD1 and one of the other anti-checkpoint antibodies mentioned above.

Motor neurological functions are evaluated using for example the rotarod performance test, which assesses the capacity of the mice to stay on a rotating rod.

It is expected that PD-Tg mice treated with one treatment session show significant improved motor performance, compared to IgG-treated or vehicle treated control group, or untreated group. PD-Tg mice which receive two courses of therapy, and examined after an appropriate interval session are expected to show a long-lasting therapeutic effect. To maintain this therapeutic effect mice are subjected to an active session of treatment with an appropriate interval session of non-treatment between each treatment session.

Example 12

Therapeutic Potential of PD-1 in Combination with CTLA-4 Immune Checkpoint Blockade in Huntington's Disease Pathology The model used in these experiments may be the Huntington's disease (HD) R6/2 transgenic mice (Tg) test system. R6/2 transgenic mice over express the mutated human huntingtin gene that includes the insertion of multiple CAG repeats mice at the progressive stages of disease. These mice show progressive behavioral-motor deficits starting as early as 5-6 weeks of age, and leading to premature death at 10-13 weeks. The symptoms include low body weight, clasping, tremor and convulsions.

The mice are treated according to one of the following regimens when they are 45 days old:

The mice are treated with one of the following anti-checkpoint antibodies: anti-ICOS, anti-B7RP1, anti-VISTA, anti-CD40, anti-CD40L, anti-CD80, anti-CD86, anti-B7-H3, anti-B7-H4, B7-H7, anti-BTLA, anti-HVEM, anti-CD137, anti-CD137L, anti-OX40L, anti-CD-27, anti-CD70, anti-STING, anti-GITR or anti-TIGIT antibody alone or in combination with an anti-CTLA-4 antibody. Some mice are treated with anti-PD-1 antibody as positive control, IgG control as negative control or combinations of anti-PD1 and one of the other anti-checkpoint antibodies mentioned above.

Motor neurological functions are evaluated using for example the rotarod performance test, which assesses the capacity of the mice to stay on a rotating rod.

It is expected that HD-Tg mice treated with one treatment session show significant improved motor performance, compared to IgG-treated or vehicle treated control group, or untreated group. HD-Tg mice which receive which receive two courses of therapy, and examined after an appropriate interval session are expected to show a long-lasting therapeutic effect. To maintain this therapeutic effect mice are subjected to an active session of treatment with an appropriate interval session of non-treatment between each treatment session.

Example 13

Therapeutic Potential of Immune Checkpoint Blockade Approach in Amyotrophic Lateral Sclerosis Pathology The model used in this experiment may be the transgenic mice overexpressing the defective human mutant SOD1 allele containing the Gly93→Ala (G93A) gene (B6SJL-TgN (SOD1-G93A) 1Gur (herein "ALS mice"). This model develop motor neuron disease and thus constitute an accepted animal model for testing ALS.

The mice are treated according to one of the following regimens when they are 75 days old:

The mice are treated with one of the following anti-checkpoint antibodies: anti-ICOS, anti-B7RP1, anti-VISTA, anti-CD40, anti-CD40L, anti-CD80, anti-CD86, anti-B7-H3, anti-B7-H4, B7-H7, anti-BTLA, anti-HVEM, anti-CD137, anti-CD137L, anti-OX40L, anti-CD-27, anti-CD70, anti-STING, anti-GITR or anti-TIGIT antibody alone or in combination with an anti-CTLA-4 antibody. Some mice are treated with anti-PD-1 antibody as positive control, IgG control as negative control or combinations of anti-PD1 and one of the other anti-checkpoint antibodies mentioned above.

Motor neurological functions are evaluated using for example the rotarod performance test, which assesses the capacity of the mice to stay on a rotating rod, or mice are allowed to grasp and hold onto a vertical wire (2 mm in diameter) with a small loop at the lower end. A vertical wire allows mice to use both fore- and hindlimbs to grab onto the wire. The wire is maintained in a vertically oriented circular motion (the circle radius was 10 cm) at 24 rpm. The time that the mouse is able to hang onto the wire is recorded with a timer.

It is expected that ALS mice treated with one treatment session show significant improved motor performance, compared to IgG-treated or vehicle treated control group, or untreated group. ALS mice which receive which receive two courses of therapy, and examined after an appropriate interval session are expected to show a long-lasting therapeutic effect. To maintain this therapeutic effect mice are subjected to an active session of treatment with an appropriate interval session of non-treatment between each treatment session.

Example 14

Dose Effect Experiments to Determine Minimal and Maximal Dose Range and Experiments to Determine Treatment Regimen and its Long Lasting Therapeutic Effect We already showed that a single treatment session utilizing PD-1 blockade leads to a significant reduction in plaque burden and improved cognitive function that lasts for at least 2 months after the treatment, the last time point that was tested. Here we describe a dose response study using two additional dosages administered to 5XFAD AD transgenic mice. The readout will be amyloid plaque burden at one, two and three months post administration. The study groups will include 1) untreated 5XFAD mice; 2) 5XFAD mice which receive 1 injection of 500 μg control anti-PD-1 (RMP1-14; #BE0146; Bioxcell Lifesciences Pvt. LTD.); 3) 5XFAD mice which receive 1 injection of 250 μg control anti-PD-1 (RMP1-14; #BE0146; Bioxcell Lifesciences Pvt. LTD.); 4) 5XFAD mice which receive 1 injection of 100 μg control anti-PD-1 (RMP1-14; #BE0146; Bioxcell Lifesciences Pvt.

LTD.); and 5) 5XFAD mice which receive 1 injection of 500 µg control IgG (IgG2a; #BE0089; Bioxcell Lifesciences Pvt. LTD.). All of the mice are treated at the start of the experiment, and from each group mice are sacrificed and their brains are examined at intervals of 1 month, 2 months, and 3 months following the start of the treatment.

It is expected that the mice treated with the anti-PD-1 antibodies display significant reduction in cerebral amyloid beta plaque load in comparison to untreated AD-Tg mice or to control IgG-treated mice.

An additional treatment session with anti-PD-1, a month after the initial treatment, was found by us to maintain the effect on cognitive performance improvement in 5XFAD AD-Tg mice (Example 5). These findings suggest that for long-term efficacy, repeated treatment sessions are needed. Here we describe a study using repeated injections for maintaining the long-lasting effect of the therapy.

5XFAD AD-Tg mice are injected with the drug at a dosage that will be determined according to the previous study results. Mice will be injected and their cognitive performance is monitored using the radial arm water maze learning and memory task during and after the study period. Histological examination of the brain for amyloid plaque burden is also performed.

Different groups of mice are injected repeatedly with single injections (or double injections 3 days apart as described in Example 5) with 2, 3 or 4 weeks intervals of non-treatment (Table 4). The mice are monitored as described above at one, two or three months after the initial treatment.

TABLE 4

Frequency of administration and timing of tests

| | Frequency | | | | | | | | | | | | |
|---|---|---|---|---|---|---|---|---|---|---|---|---|---|
| Week | 0 | 1 | 2 | 3 | 4 | 5 | 6 | 7 | 8 | 9 | 10 | 11 | 12 |
| 2 | x | | x | | x | | x | | x | | | | |
| 3 | x | | | x | | | x | | | x | | | |
| 4 | x | | | | x | | | | x | | | | |
| Test | | | | | T | | | | T | | | | T |

Example 15

Systemic Administration of Anti-PD-1 Monoclonal Antibody in RCS Rats Attenuates Retinal Degeneration The aim of this experiment was to determine whether systemic administration of an anti-PD1 antibody attenuates the degeneration of the outer nuclear layer in an animal model of a retinal degeneration disease.

RCS rats, an accepted animal model of dry AMD and Retinitis Pigmentosa and other retinal degenerative diseases and conditions, carry a deletion mutation in the gene encoding the MerTK protein which leads to retinal degeneration and complete loss of sight by the age of three months. A significant and rapid deterioration in the thickness of the retinal outer nuclear layer (ONL) is observed starting at the age of 4 weeks. Preservation of ONL thickness in this model is thus considered in the scientific literature to be directly correlated to preservation of sight.

RCS rats were injected intraperitoneally (IP) at the age of 4 weeks with either anti-PD1 monoclonal antibodies (total of 760 µg per animal; n=10) or suitable IgG control (IgG2a) at the same concentration (n=10). An additional group of RCS rats were left untreated (n=4). 2 weeks post-treatment, at the age of 6 weeks, the animals were sacrificed, their eyes excised and the thickness of the retinal ONL layer in each eye was determined through histological analysis using H&E stain. Treatment efficacy was determined by measuring the ONL thickness throughout the entire retinal length and horizontally plotting the data to generate a map that allows identification of treatment effects in any area of the retina.

Figure 19A:
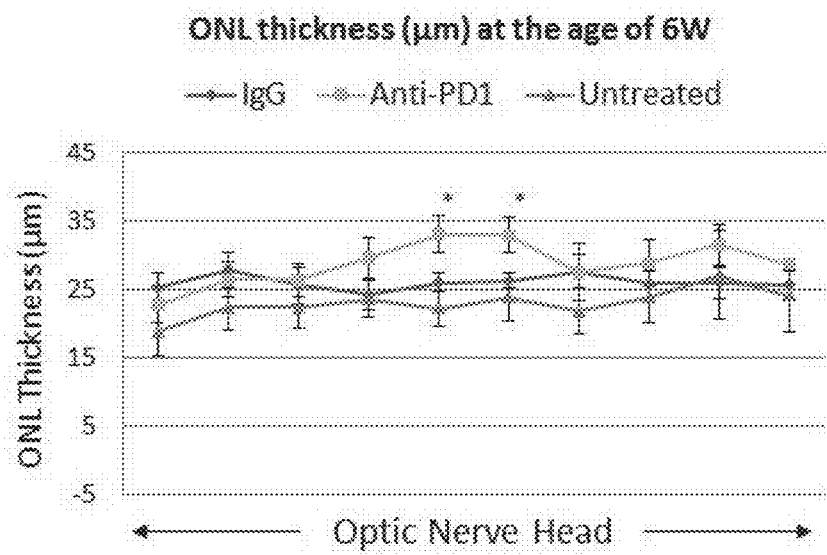
FIG. 19A-B shows thickness plots of the outer nuclear layer (ONL) throughout the entire retina measured in individual eyes of RCS rats treated by intraperitoneal injection with anti-PD1 mAb (n=10 rats; 20 eyes), IgG (n=10 rats; 20 eyes) or untreated animals (n=4 rats; 8 eyes) through histological analysis based on H&E stain with (A) showing all animals and (B) showing responders only. Data is presented as mean±standard error values; *$P<0.05$; **$P<0.01$.

Analyzing the mean ONL thickness of all treated animals where each individual eye served as an independent data set, showed that at the age of 6 weeks (2 weeks after treatment), the ONL at the central area of the retina in close proximity to the optic nerve head was significantly thicker in anti-PD1 treated animals compared to both IgG-treated and untreated controls (FIG. 19A).

Figure 19B:
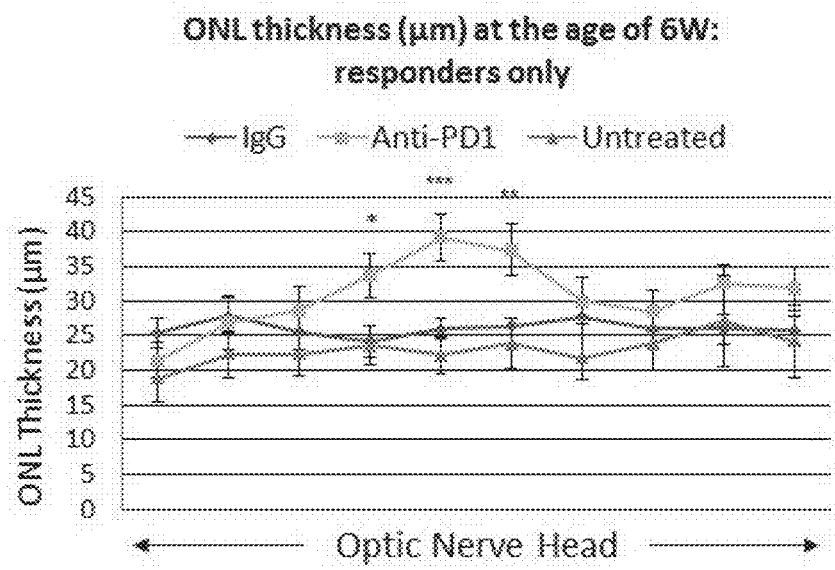

To evaluate the magnitude of the effect in treatment-responsive animals only, a threshold value for defining an animal as a 'positive responsive animal' was set as a value equals to 2 standard error values above the mean thickness value in the central retina of the IgG control group. Based on this set threshold value, 13 of the 20 analyzed eyes (65%) in the anti-PD1 group were characterized as positive-responders. In comparison, only 1 of 20 (5%) analyzed eye was characterized as a positive-responder in the IgG treatment group; a significant difference (Chi-square=15.82, P=0.00007). Looking only at the 13 anti-PD1 positive-responsive eyes of this treatment group showed that the thickness at the central retina area was 1.5-2 times double of that of the control eyes. Moreover, an even wider area of the central retina was significantly thicker compared to the control groups (FIG. 19B). Interestingly, although the antibody was administered systemically and is expected to reach and act on both eyes at a similar level, differences in responsiveness to the treatment between the two eyes of individual animals were observed in four of the anti-PD-1 treated animals.

Example 16

Local Administration of Anti-PD-1 Monoclonal Antibody Directly into the Vitreous in RCS Rats Attenuates Retinal Degeneration The aim of this experiment was to determine whether local administration of an anti-PD1 antibody directly into the vitreous of the eye attenuates the degeneration of the outer nuclear layer in an animal model of a retinal degeneration disease.

RCS rats at the age of 4 weeks were injected with either anti-PD1 monoclonal antibodies (n=6) or suitable IgG control (50 µg per animal). Injection was performed directly into the vitreous of a single eye of each animal while the contralateral eye was left untreated. 2 weeks post-treatment, at the age of 6 weeks, the animals were sacrificed, their eyes excised and the thickness of the retinal ONL layer in each eye was determined through histological analysis using H&E stain. Treatment efficacy was determined by measuring the ONL thickness throughout the entire retinal length and horizontally plotting the data to generate a map that allows identification of treatment effects in any area of the retina.

Analyzing the mean ONL thickness of the animals 2 weeks after treatment showed that in the anti-PD1-treated group, the ONL was significantly thicker in several sections of the retina in the treated eye compared to the untreated contralateral eye (FIG. 20A). No such effect was found in the IgG-treated animals (FIG. 20B).

Example 17

Local PD-1 Blockade Through Intravitreal Injection of PD-1 or PD-L1 Monoclonal Antibodies Attenuates Retinal Degeneration Anti-PD-L1 monoclonal antibodies or anti-PD-1 monoclonal antibodies, a combination of Anti-PD-L1 and anti-PD-1 monoclonal antibodies or suitable IgG fragments without the antigen-specific variable region, will be injected directly into the vitreous of RCS rats at 4 weeks of age. Throughout the 8 following weeks, assessment of visual function of the animals in response to visual stimuli will be taken. Importantly, only a single eye of each animal will receive the treatment while the contra-lateral eye will be left untreated and will serve as an additional control. In addition, throughout the experiment, designated groups of RCS rats from each treatment group will be subjected to analysis aiming at quantifying and qualifying the treatment effect on the retina in term of neuronal survival and local immune response, as well as the effect on the retinal epithelial cells in terms of their expression of leukocyte trafficking molecules and immune checkpoint ligands. Local blockade of the PD-1/PD-L1 pathway through intravitreal injection is expected to result in attenuation of retinal degeneration, immune modulation and preservation of visual function.

Example 18

Figure 21:
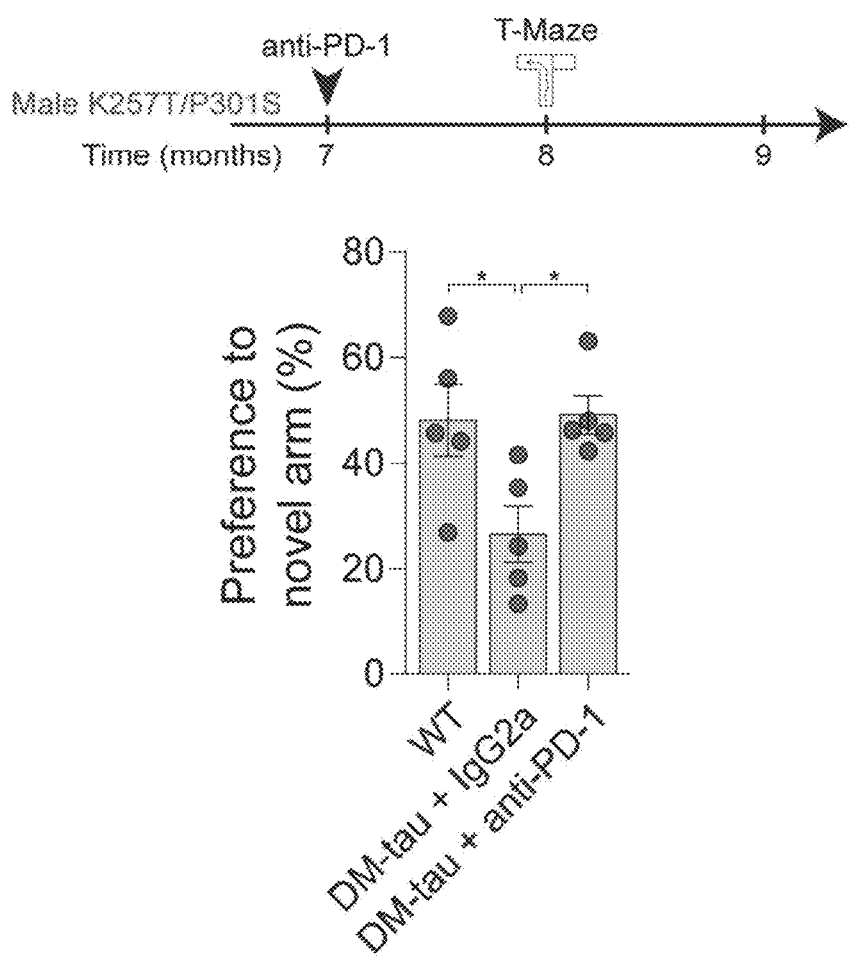
FIG. 21 shows beneficial effect of PD-1 blockade on memory performance in the DM-htau mouse model of Alzheimer's disease.

PD-1 Blockade Beneficial Effect on Memory Performance in the DM-Htau Mouse Model of Alzheimer's Disease Male mice expressing the human-tau (htau) gene with two mutations (K257T/P301S; double mutant, DM (Rosenmann et al., 2008) were treated at the age of 7 months with either anti-PD-1-specific antibody (IgG2a rat anti-mouse PD-1; n=5), or IgG control (Rat IgG2a; n=5), and were tested by T-maze cognitive task a month after. Aged matched wild-type (WT; n=5) non-transgenic littermates mice were used as additional control group. The experiment was performed in a blinded fashion to the identity of the treatment groups—both during T-maze testing, and during quantification of time spent in each arm of the T-maze. Repeated-measures were analyzed using one-way ANOVA and Tukey's post-test. Error bars represent mean±s.e.m.; * $P<0.05$. The results show that systemic blockade of the PD-1/PD-L1 pathway triggers a protective immune activity which mitigates the pathological events in the brain of AD mice also in the absence of amyloid beta related pathology. The DM-htau model mimics the human pathology of abnormal human tau protein in the brain, which appears in other diseases (in addition to Alzheimer's disease) collectively called tauopathies. The list of tauopathies include Pick's disease, progressive supranuclear palsy, corticobasal degeneration, argyrophilic grain disease, primary age-related tauopathy, formerly called also as neurofibrillary tangleonly dementia, and a recently characterized entity called globular glial tauopathy (FIG. 21).

Example 19

PD-1 Blockade Enhances Hippocampal Neurogenesis in 5XFAD Mice

Figure 22A:
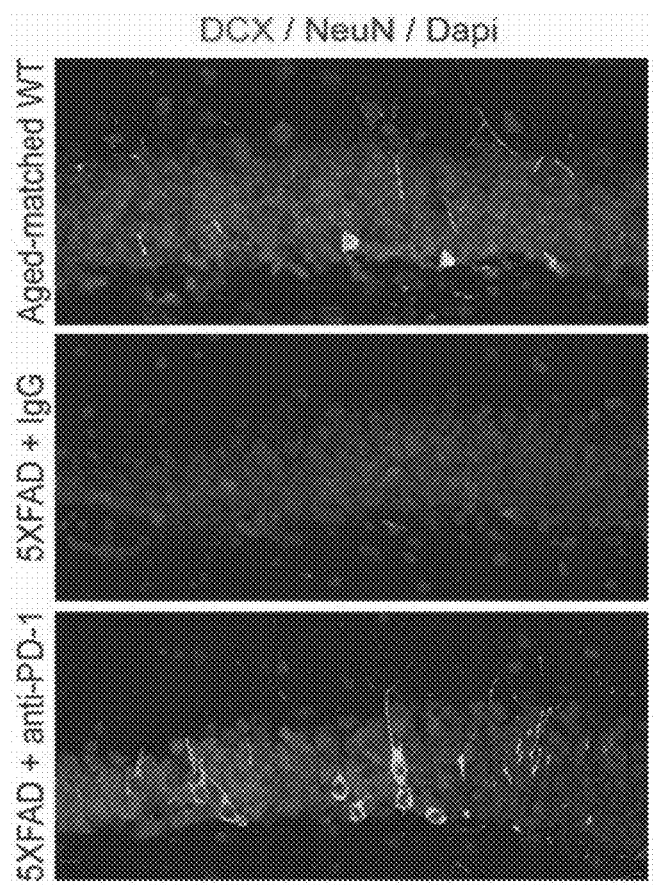
FIG. 22A-B shows PD-1 blockade enhances hippocampal neurogenesis in 5XFAD mice with (A) showing parasagittal brain sections immunostained for neuronal marker-NeuN (in green), DCX (in red), and hoechst nuclear staining (in blue); and (B) showing a graph quantitating the staining in anti-PD-1 treated animals, IgG immune controls and aged-matched wild-type controls.
Figure 22B:
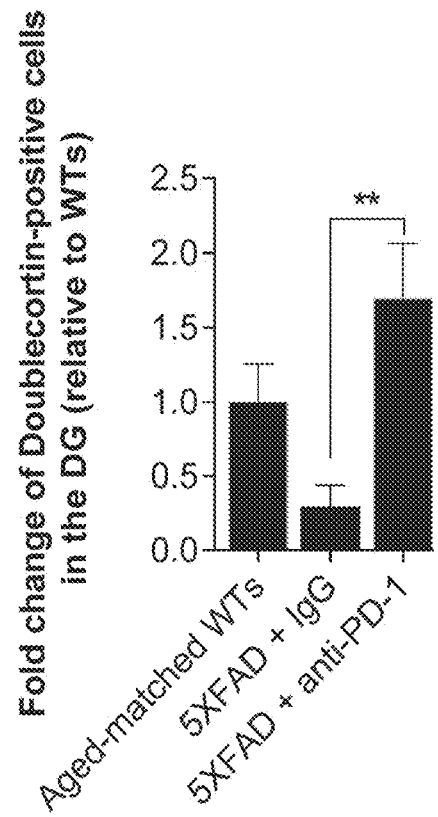

Doublecortin (DCX) is a microtubule-associated protein expressed by neuronal precursor cells and immature neurons. In the adult neuronal tissue DCX is used as a marker for neurogenesis since it is expressed almost solely by developing neurons. Female 5XFAD mice (average cohorts aged 6 months) were treated with either anti-PD-1-specific antibody (IgG2a anti-mouse PD-1; n=17), or IgG control (Rat IgG2a; n=7), and were sacrificed a month after. Aged matched wild-type (WT; n=9) mice were used as additional control group. Parasagittal brain sections from representative animals were prepared and the granular layer of the dentate gyrus was marked (FIG. 22A). Brain sections were immunostained for neuronal marker-NeuN (in green), DCX (in red), and hoechst nuclear staining (in blue). DCX+ cells were quantified in a double-blinded manner from 6 m thick brain slices (FIG. 22B). Repeated measures were analyzed using one-way ANOVA and Dunnett post-test. Error bars represent mean±s.e.m.; * $P<0.05$,  $P<0.01$, * $P<0.001$. The results show that systemic blockade of PD-1/PD-L1 pathway triggers a protective immune activity which modulates the brain environment to support hippocampal neurogenesis, an effect on pathology which was repeatedly correlated before to a beneficial effect on behavior deficits and cognitive deficits.

Example 20

PD-1 Blockade Enhances Hippocampal Synaptic Plasticity in 5XFAD Mice

Vesicular glutamate transporters 1 (VGLUT1), expressed by glutamatergic neurons, mediate glutamate uptake into synaptic vesicles and was shown to contribute to hippocampal synaptic plasticity and hippocampus-dependent spatial learning. Female 5XFAD mice (average cohorts aged 6 months) were treated with either anti-PD-1-specific antibody (IgG2a anti-mouse PD-1; n=17), or IgG control (Rat IgG2a; n=7), and were sacrificed a month after. Aged matched wild-type (WT; n=9) mice were used as additional control group. Parasagittal brain sections from representative animals were prepared and the Subiculum region was marked (FIG. 23A). Brain sections were immunostained for VgluT1. Florescence intensity was quantified in a double-blinded manner using the ImageJ software from 6 m thick brain slices (FIG. 23B). Repeated measures were analyzed using one-way ANOVA and Dunnett post-test). Error bars represent mean±s.e.m.; * $P<0.05$,  $P<0.01$, * $P<0.001$. The results show that systemic blockade of PD-1/PD-L1 pathway triggers a protective immune activity in the periphery and which modulates the brain environment to support synaptic plasticity and preserve cognitive function.

Example 21

PD-1 Blockade Reduces Neuronal Loss in the Subiculum of 5XFAD Mice

Figure 24A:
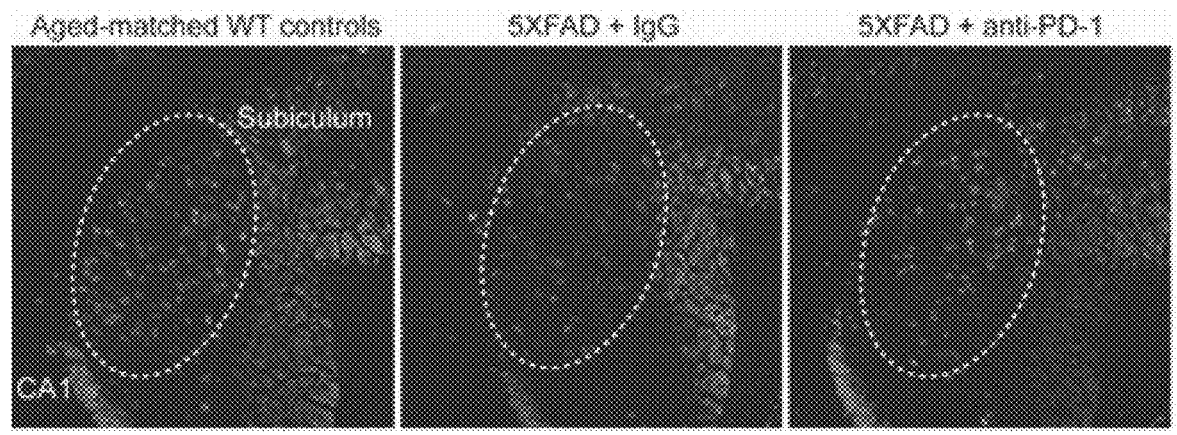
FIG. 24A-B shows PD-1 blockade reduces neuronal loss in the subiculum of 5XFAD mice with (A) showing parasagittal brain sections immunostained for neuronal marker-NeuN (in green); and (B) showing a graph quantitating the staining in anti-PD-1 treated animals, IgG immune controls and aged-matched wild-type controls.
Figure 24B:
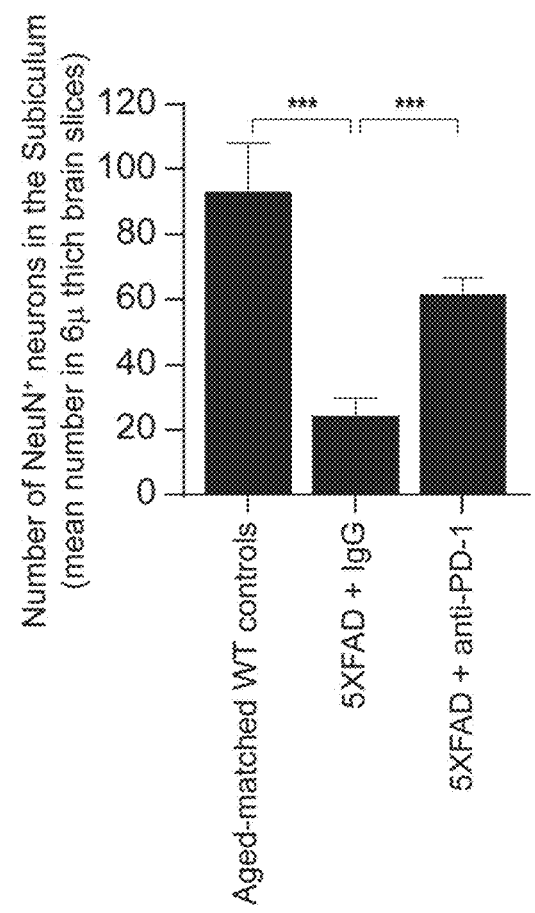

The 5XFAD transgenic mouse model is one of the few amyloid animal models that exhibits significant neuron loss, similar to AD progression in human patients. Neuronal loss in 5XFAD mice was characterized in the Subiculum and cortical Layer 5. Female 5XFAD mice (average cohorts aged 6 months) were treated with either anti-PD-1-specific antibody (IgG2a anti-mouse PD-1; n=17), or IgG control (Rat IgG2a; n=7), and were sacrificed a month after. Aged matched wild-type (WT; n=9) mice were used as additional control group. Parasagittal brain sections from representative animals were prepared and the Subiculum region was marked (FIG. 24A). Brain sections were immunostained for NeuN, labeling neurons (in green). Subiculum neurons were quantified in a double-blinded manner using the ImageJ software from 6 m thick brain slices (FIG. 24B). Repeated measures were analyzed using one-way ANOVA and Dunnett post-test). Error bars represent mean±s.e.m.; * $P<0.05$,  $P<0.01$, * $P<0.001$. The results show that systemic blockade of PD-1/PD-L1 pathway triggers a protective immune activity which modulates the brain environment to become permissive for support neuronal survival and rescue, eventually contributing to better cognitive performance.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular compound, composition, article, apparatus, methodology, protocol, and/or reagent, etc., described herein, unless expressly stated as such. In addition, those of ordinary skill in the art will recognize that certain changes, modifications, permutations, alterations, additions, subtractions and sub-combinations thereof can be made in accordance with the teachings herein without departing from the spirit of the present specification. It is therefore intended that the following appended claims and claims hereafter introduced are interpreted to include all such changes, modifications, permutations, alterations, additions, subtractions and sub-combinations as are within their true spirit and scope.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. For instance, as mass spectrometry instruments can vary slightly in determining the mass of a given analyte, the term "about" in the context of the mass of an ion or the mass/charge ratio of an ion refers to +/−0.50 atomic mass unit. At the very least, and not as an attempt to limit the application of the doctrine of equivalents to the scope of the claims, each numerical indication should at least be construed in light of the number of reported significant digits and by applying ordinary rounding techniques.

Use of the terms "may" or "can" in reference to an embodiment or aspect of an embodiment also carries with it the alternative meaning of "may not" or "cannot." As such, if the present specification discloses that an embodiment or an aspect of an embodiment may be or can be included as part of the inventive subject matter, then the negative limitation or exclusionary proviso is also explicitly meant, meaning that an embodiment or an aspect of an embodiment may not be or cannot be included as part of the inventive subject matter. In a similar manner, use of the term "optionally" in reference to an embodiment or aspect of an embodiment means that such embodiment or aspect of the embodiment may be included as part of the inventive subject matter or may not be included as part of the inventive subject matter. Whether such a negative limitation or exclusionary proviso applies will be based on whether the negative limitation or exclusionary proviso is recited in the claimed subject matter.

Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar references used in the context of describing the present invention (especially in the context of the following claims) are to be construed to cover both the singular and the plural, unless otherwise indicated herein or clearly contradicted by context. Further, ordinal indicators—such as "first," "second," "third," etc.—for identified elements are used to distinguish between the elements, and do not indicate or imply a required or limited number of such elements, and do not indicate a particular position or order of such elements unless otherwise specifically stated. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

When used in the claims, whether as filed or added per amendment, the open-ended transitional term "comprising" (and equivalent open-ended transitional phrases thereof like including, containing and having) encompasses all the expressly recited elements, limitations, steps and/or features alone or in combination with unrecited subject matter; the named elements, limitations and/or features are essential, but other unnamed elements, limitations and/or features may be added and still form a construct within the scope of the claim. Specific embodiments disclosed herein may be further limited in the claims using the closed-ended transitional phrases "consisting of" or "consisting essentially of" in lieu of or as an amended for "comprising." When used in the claims, whether as filed or added per amendment, the closed-ended transitional phrase "consisting of" excludes any element, limitation, step, or feature not expressly recited in the claims. The closed-ended transitional phrase "consisting essentially of" limits the scope of a claim to the expressly recited elements, limitations, steps and/or features and any other elements, limitations, steps and/or features that do not materially affect the basic and novel characteristic(s) of the claimed subject matter. Thus, the meaning of the open-ended transitional phrase "comprising" is being defined as encompassing all the specifically recited elements, limitations, steps and/or features as well as any optional, additional unspecified ones. The meaning of the closed-ended transitional phrase "consisting of" is being defined as only including those elements, limitations, steps and/or features specifically recited in the claim whereas the meaning of the closed-ended transitional phrase "consisting essentially of" is being defined as only including those elements, limitations, steps and/or features specifically recited in the claim and those elements, limitations, steps and/or features that do not materially affect the basic and novel characteristic(s) of the claimed subject matter. Therefore, the open-ended transitional phrase "comprising" (and equivalent open-ended transitional phrases thereof) includes within its meaning, as a limiting case, claimed subject matter specified by the closed-ended transitional phrases "consisting of" or "consisting essentially of." As such embodiments described herein or so claimed with the phrase "comprising" are expressly or inherently unambiguously described, enabled and supported herein for the phrases "consisting essentially of" and "consisting of."

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Lastly, the terminology used herein is for the purpose of describing particular embodiments only, and is not intended to limit the scope of the present invention, which is defined solely by the claims. Accordingly, the present invention is not limited to that precisely as shown and described.

The invention claimed is:

1. A method of treating a tauopathy to an individual in need thereof, the method comprising administering to the individual a composition comprising an anti-PD-1 antibody, an anti-PD-L1 antibody, an anti-TIM-3 antibody, or any combination thereof,
   wherein the composition is administered by a dosage regime comprising at least two courses of therapy, each course of therapy comprising in sequence a treatment session where the composition is administered to the individual followed by a non-treatment period where the composition is not administered to the individual, wherein the non-treatment period is longer than the treatment session;
   wherein, if administration of the composition during the treatment session is a repeated administration, the non-treatment period is longer than the period between repeated administrations during the treatment session;
   wherein administration of the composition transiently reduces levels of systemic immunosuppression and increases choroid plexus gateway activity in facilitating selective recruitment of immune cells into the central nervous system, thereby treating the individual.

2. The method according to claim 1, wherein the administration of the composition during the treatment session is a single administration.

3. The method according to claim 1, wherein the administration of the composition during the treatment session is a repeated administration.

4. The method according to claim 3, wherein the repeated administration occurs once every day, once every two days, once every three days, once every four days, once every five days or once every six days.

5. The method according to claim 4, wherein the repeated administration occurs once weekly or once every two weeks, once every three weeks or once every four weeks.

6. The method according to claim 1, wherein the treatment session is from 1 day to four weeks.

7. The method according to claim 6, wherein the treatment session is from 3 days to four weeks.

8. The method according to claim 7, wherein the treatment session is from one week to four weeks.

9. The method according to claim 1, wherein the non-treatment period is from one week to six months.

10. The method according to claim 9, wherein the non-treatment period is from two weeks to six months.

11. The method according to claim 10, wherein the non-treatment period is from three weeks to six months.

12. The method according to claim 11, wherein the non-treatment period is from one month to three months.

13. The method according to claim 12, wherein the non-treatment period is from one month to two months.

14. The method according to claim 1, wherein the anti-PD-1 antibody is a neutralizing anti-PD-1 antibody, the anti-PD-L1 antibody is a neutralizing anti-PD-L1 antibody and/or the anti-TIM-3antibody is a neutralizing anti-TIM-3 antibody.

15. The method according to claim 14, wherein the anti-PD-1 antibody is a human neutralizing anti-PD-1 antibody or a humanized, neutralizing anti-PD-1 antibody.

16. The method according to claim 14, wherein the anti-PD-L1 antibody is a human neutralizing anti-PD-L1 antibody or a humanized, neutralizing anti-PD-L1 antibody.

17. The method according to claim 14, wherein the anti-TIM-3 antibody is a human neutralizing anti-TIM-3 antibody or a humanized, neutralizing anti-TIM-3 antibody.

18. The method according to claim 1, wherein the transient reduction in the level of systemic immunosuppression is associated with an increase in a systemic presence or activity of IFNγ-producing leukocytes and/or an increase in a systemic presence or activity of an IFNγ cytokine.

19. The method according to claim 1, wherein the transient reduction in the level of systemic immunosuppression is associated with an increase in a systemic presence or activity of effector T cells.

20. The method according to claim 1, wherein the transient reduction in the level of systemic immunosuppression is associated with a decrease in a systemic presence or activity of regulatory T cells and/or a decrease in a systemic presence of an IL-10 cytokine.

21. The method according to claim 1, wherein the transient reduction in the level of systemic immunosuppression is associated with a decrease in a systemic presence or myeloid-derived suppressor cells (MDSCs).

22. The method according to claim 1, wherein the transient reduction in the level of systemic immunosuppression occurs by release of a restraint imposed on the immune system by one or more immune checkpoints.

23. The method according to claim 22, wherein administration of the composition blocks the one or more immune checkpoints, thereby causing the transient reduction in the level of systemic immunosuppression.

24. The method according to claim 23, wherein the one or more immune checkpoints includes a PD1-PD-L1, a PD1-PD-L2, a TIM-3-Gal9 or any combination thereof.

25. The method according to claim 1, wherein the administration of the composition during the treatment session is maintained at least until a systemic presence or activity of IFNγ-producing leukocytes and/or an IFNγ cytokine rises above a reference, at which point the administration is stopped, and the non-treatment period is maintained as long as the systemic presence or activity of IFNγ-producing leukocytes and/or an IFNγ cytokine is above the reference, wherein the reference includes a) a level of a systemic presence or activity of IFNγ-producing leukocytes and/or an IFNγ cytokine measured in the most recent blood sample obtained from the individual before the administering; or b) a level of a systemic presence or activity of IFNγ-producing leukocytes and/or an IFNγ cytokine characteristic of a population of individuals afflicted with the tauopathy.

26. The method according to claim 1, wherein a cerebral level of soluble amyloid beta peptide is reduced in the individual, a cerebral amyloid beta (Aβ) plaque burden is reduced or cleared in the individual, a hippocampal gliosis is reduced in the individual, a cerebral level of a pro-inflammatory cytokine is reduced in the individual, a brain inflammation is decreased in the individual and/or a cognitive function is improved in the individual.

27. The method according to claim 26, wherein the improved cognitive function is learning, memory, creation of imagery, plasticity, thinking, awareness, reasoning, spatial ability, speech and language skills, language acquisition, capacity for judgment attention or any combination thereof.

28. The method according to claim 1, wherein the immune cells include monocytes, macrophages, or T cells.

29. The method according to 28, wherein the T cells include regulatory T cells.

30. The method according to claim 1, wherein the tauopathy is Alzheimer's disease, argyrophilic grain disease, chronic traumatic encephalopathy, corticobasal degeneration, dementia pugilistica, frontotemporal dementia, frontotemporal lobar degeneration, Hallervorden-Spatz disease, Huntington's disease, ganglioglioma, gangliocytoma, globular glial tauopathy, lead encephalopathy, lipofuscinosis, Lytico-Bodig disease (Parkinson-dementia complex of Guam), meningioangiomatosis, Parkinsonism disease linked to chromosome 17, Pick's disease, primary age-related tauopathy (PART), formerly known as neurofibrillary tangle-only dementia (NFT-dementia), postencephalitic parkinsonism, progressive supranuclear palsy, subacute sclerosing panencephalitis or tuberous sclerosis.

* * * * *

SEQUENCE LISTING

```
<160> NUMBER OF SEQ ID NOS: 56

<210> SEQ ID NO 1
<211> LENGTH: 15
<212> TYPE: PRT
<213> ORGANISM: Artificial Sequence
<220> FEATURE:
<223> OTHER INFORMATION: Synthetic

<400> SEQUENCE: 1

Ala Ala Ala Tyr Ala Ala Ala Ala Ala Ala Lys Ala Ala Ala Ala
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: Synthetic

<400> SEQUENCE: 2

Ala Glu Lys Tyr Ala Ala Ala Ala Ala Ala Lys Ala Ala Ala Ala
1               5                   10                  15

<210> SEQ ID NO 3
<211> LENGTH: 15
<212> TYPE: PRT
<213> ORGANISM: Artificial Sequence
<220> FEATURE:
<223> OTHER INFORMATION: Synthetic

<400> SEQUENCE: 3

Ala Lys Glu Tyr Ala Ala Ala Ala Ala Ala Lys Ala Ala Ala Ala
1               5                   10                  15
```

-continued

```
<210> SEQ ID NO 4
<211> LENGTH: 15
<212> TYPE: PRT
<213> ORGANISM: Artificial Sequence
<220> FEATURE:
<223> OTHER INFORMATION: Synthetic

<400> SEQUENCE: 4

Ala Lys Lys Tyr Ala Ala Ala Ala Ala Lys Ala Ala Ala Ala Ala
1               5                   10                  15

<210> SEQ ID NO 5
<211> LENGTH: 15
<212> TYPE: PRT
<213> ORGANISM: Artificial Sequence
<220> FEATURE:
<223> OTHER INFORMATION: Synthetic

<400> SEQUENCE: 5

Ala Glu Ala Tyr Ala Ala Ala Ala Ala Lys Ala Ala Ala Ala Ala
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: Synthetic

<400> SEQUENCE: 6

Lys Glu Ala Tyr Ala Ala Ala Ala Ala Lys Ala Ala Ala Ala Ala
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: Synthetic

<400> SEQUENCE: 7

Ala Glu Glu Tyr Ala Ala Ala Ala Ala Lys Ala Ala Ala Ala Ala
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: Synthetic

<400> SEQUENCE: 8

Ala Ala Glu Tyr Ala Ala Ala Ala Ala Lys Ala Ala Ala Ala Ala
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: Synthetic

<400> SEQUENCE: 9

Glu Lys Ala Tyr Ala Ala Ala Ala Ala Lys Ala Ala Ala Ala Ala
1               5                   10                  15

<210> SEQ ID NO 10
```

```
<211> LENGTH: 15
<212> TYPE: PRT
<213> ORGANISM: Artificial Sequence
<220> FEATURE:
<223> OTHER INFORMATION: Synthetic

<400> SEQUENCE: 10

Ala Ala Lys Tyr Glu Ala Ala Ala Lys Ala Ala Ala Ala
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: Synthetic

<400> SEQUENCE: 11

Ala Ala Lys Tyr Ala Glu Ala Ala Ala Lys Ala Ala Ala Ala
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: Synthetic

<400> SEQUENCE: 12

Glu Ala Ala Tyr Ala Ala Ala Ala Ala Lys Ala Ala Ala Ala
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: Synthetic

<400> SEQUENCE: 13

Glu Lys Lys Tyr Ala Ala Ala Ala Ala Lys Ala Ala Ala Ala
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: Synthetic

<400> SEQUENCE: 14

Glu Ala Lys Tyr Ala Ala Ala Ala Ala Lys Ala Ala Ala Ala
1               5                   10                  15

<210> SEQ ID NO 15
<211> LENGTH: 15
<212> TYPE: PRT
<213> ORGANISM: Artificial Sequence
<220> FEATURE:
<223> OTHER INFORMATION: Synthetic

<400> SEQUENCE: 15

Ala Glu Lys Tyr Ala Ala Ala Ala Ala Ala Ala Ala Ala Ala
1               5                   10                  15

<210> SEQ ID NO 16
<211> LENGTH: 15
```

```
<212> TYPE: PRT
<213> ORGANISM: Artificial Sequence
<220> FEATURE:
<223> OTHER INFORMATION: Synthetic

<400> SEQUENCE: 16

Ala Lys Glu Tyr Ala Ala Ala Ala Ala Ala Ala Ala Ala
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: Synthetic

<400> SEQUENCE: 17

Ala Lys Lys Tyr Glu Ala Ala Ala Ala Ala Ala Ala Ala
1               5                   10                  15

<210> SEQ ID NO 18
<211> LENGTH: 15
<212> TYPE: PRT
<213> ORGANISM: Artificial Sequence
<220> FEATURE:
<223> OTHER INFORMATION: Synthetic

<400> SEQUENCE: 18

Ala Lys Lys Tyr Ala Glu Ala Ala Ala Ala Ala Ala Ala
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: Synthetic

<400> SEQUENCE: 19

Ala Glu Ala Tyr Lys Ala Ala Ala Ala Ala Ala Ala Ala
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: Synthetic

<400> SEQUENCE: 20

Lys Glu Ala Tyr Ala Ala Ala Ala Ala Ala Ala Ala Ala
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: Synthetic

<400> SEQUENCE: 21

Ala Glu Glu Tyr Lys Ala Ala Ala Ala Ala Ala Ala Ala
1               5                   10                  15

<210> SEQ ID NO 22
<211> LENGTH: 15
<212> TYPE: PRT
```

```
<213> ORGANISM: Artificial Sequence
<220> FEATURE:
<223> OTHER INFORMATION: Synthetic

<400> SEQUENCE: 22

Ala Ala Glu Tyr Lys Ala Ala Ala Ala Ala Ala Ala Ala Ala Ala
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: Synthetic

<400> SEQUENCE: 23

Glu Lys Ala Tyr Ala Ala Ala Ala Ala Ala Ala Ala Ala Ala Ala
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: Synthetic

<400> SEQUENCE: 24

Ala Ala Lys Tyr Glu Ala Ala Ala Ala Ala Ala Ala Ala Ala Ala
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: Synthetic

<400> SEQUENCE: 25

Ala Ala Lys Tyr Ala Glu Ala Ala Ala Ala Ala Ala Ala Ala Ala
1               5                   10                  15

<210> SEQ ID NO 26
<211> LENGTH: 15
<212> TYPE: PRT
<213> ORGANISM: Artificial Sequence
<220> FEATURE:
<223> OTHER INFORMATION: Synthetic

<400> SEQUENCE: 26

Glu Lys Lys Tyr Ala Ala Ala Ala Ala Ala Ala Ala Ala Ala Ala
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: Synthetic

<400> SEQUENCE: 27

Glu Ala Lys Tyr Ala Ala Ala Ala Ala Ala Ala Ala Ala Ala Ala
1               5                   10                  15

<210> SEQ ID NO 28
<211> LENGTH: 15
<212> TYPE: PRT
<213> ORGANISM: Artificial Sequence
```

-continued

```
<220> FEATURE:
<223> OTHER INFORMATION: Synthetic

<400> SEQUENCE: 28

Ala Glu Tyr Ala Lys Ala Ala Ala Ala Ala Ala Ala Ala Ala Ala
1               5                   10                  15

<210> SEQ ID NO 29
<211> LENGTH: 15
<212> TYPE: PRT
<213> ORGANISM: Artificial Sequence
<220> FEATURE:
<223> OTHER INFORMATION: Synthetic

<400> SEQUENCE: 29

Ala Glu Lys Ala Tyr Ala Ala Ala Ala Ala Ala Ala Ala Ala Ala
1               5                   10                  15

<210> SEQ ID NO 30
<211> LENGTH: 15
<212> TYPE: PRT
<213> ORGANISM: Artificial Sequence
<220> FEATURE:
<223> OTHER INFORMATION: Synthetic

<400> SEQUENCE: 30

Glu Lys Tyr Ala Ala Ala Ala Ala Ala Ala Ala Ala Ala Ala Ala
1               5                   10                  15

<210> SEQ ID NO 31
<211> LENGTH: 15
<212> TYPE: PRT
<213> ORGANISM: Artificial Sequence
<220> FEATURE:
<223> OTHER INFORMATION: Synthetic

<400> SEQUENCE: 31

Ala Tyr Lys Ala Glu Ala Ala Ala Ala Ala Ala Ala Ala Ala Ala
1               5                   10                  15

<210> SEQ ID NO 32
<211> LENGTH: 15
<212> TYPE: PRT
<213> ORGANISM: Artificial Sequence
<220> FEATURE:
<223> OTHER INFORMATION: Synthetic

<400> SEQUENCE: 32

Ala Lys Tyr Ala Glu Ala Ala Ala Ala Ala Ala Ala Ala Ala Ala
1               5                   10                  15

<210> SEQ ID NO 33
<211> LENGTH: 24
<212> TYPE: DNA
<213> ORGANISM: Artificial Sequence
<220> FEATURE:
<223> OTHER INFORMATION: Synthetic

<400> SEQUENCE: 33
agcatacagg tcctggcatc ttgt                                          24

<210> SEQ ID NO 34
<211> LENGTH: 24
<212> TYPE: DNA
<213> ORGANISM: Artificial Sequence
<220> FEATURE:
<223> OTHER INFORMATION: Synthetic
```

```
<400> SEQUENCE: 34
caaagaccac atgcttgcca tcca                                          24

<210> SEQ ID NO 35
<211> LENGTH: 24
<212> TYPE: DNA
<213> ORGANISM: Artificial Sequence
<220> FEATURE:
<223> OTHER INFORMATION: Synthetic

<400> SEQUENCE: 35
agatcacatt cacggtgctg gcta                                          24

<210> SEQ ID NO 36
<211> LENGTH: 24
<212> TYPE: DNA
<213> ORGANISM: Artificial Sequence
<220> FEATURE:
<223> OTHER INFORMATION: Synthetic

<400> SEQUENCE: 36
agctttggga tggtagctgg aaga                                          24

<210> SEQ ID NO 37
<211> LENGTH: 24
<212> TYPE: DNA
<213> ORGANISM: Artificial Sequence
<220> FEATURE:
<223> OTHER INFORMATION: Synthetic

<400> SEQUENCE: 37
tgtgaaggga ttaacgaggc tgga                                          24

<210> SEQ ID NO 38
<211> LENGTH: 24
<212> TYPE: DNA
<213> ORGANISM: Artificial Sequence
<220> FEATURE:
<223> OTHER INFORMATION: Synthetic

<400> SEQUENCE: 38
ccatgtttcg ggcacatttc caca                                          24

<210> SEQ ID NO 39
<211> LENGTH: 21
<212> TYPE: DNA
<213> ORGANISM: Artificial Sequence
<220> FEATURE:
<223> OTHER INFORMATION: Synthetic

<400> SEQUENCE: 39
aactgcatcc atatcgatga c                                             21

<210> SEQ ID NO 40
<211> LENGTH: 19
<212> TYPE: DNA
<213> ORGANISM: Artificial Sequence
<220> FEATURE:
<223> OTHER INFORMATION: Synthetic

<400> SEQUENCE: 40
gtggcaatga tctcaacac                                                19

<210> SEQ ID NO 41
```

```
<211> LENGTH: 18
<212> TYPE: DNA
<213> ORGANISM: Artificial Sequence
<220> FEATURE:
<223> OTHER INFORMATION: Synthetic

<400> SEQUENCE: 41
catccacgtg ttggctca                                                 18

<210> SEQ ID NO 42
<211> LENGTH: 23
<212> TYPE: DNA
<213> ORGANISM: Artificial Sequence
<220> FEATURE:
<223> OTHER INFORMATION: Synthetic

<400> SEQUENCE: 42
gatcatcttg ctggtgaatg agt                                           23

<210> SEQ ID NO 43
<211> LENGTH: 20
<212> TYPE: DNA
<213> ORGANISM: Artificial Sequence
<220> FEATURE:
<223> OTHER INFORMATION: Synthetic

<400> SEQUENCE: 43
gcctcttctc attcctgctt                                               20

<210> SEQ ID NO 44
<211> LENGTH: 20
<212> TYPE: DNA
<213> ORGANISM: Artificial Sequence
<220> FEATURE:
<223> OTHER INFORMATION: Synthetic

<400> SEQUENCE: 44
ctcctccact tggtggtttg                                               20

<210> SEQ ID NO 45
<211> LENGTH: 21
<212> TYPE: DNA
<213> ORGANISM: Artificial Sequence
<220> FEATURE:
<223> OTHER INFORMATION: Synthetic

<400> SEQUENCE: 45
ccaaaagatg aagggctgct t                                             21

<210> SEQ ID NO 46
<211> LENGTH: 20
<212> TYPE: DNA
<213> ORGANISM: Artificial Sequence
<220> FEATURE:
<223> OTHER INFORMATION: Synthetic

<400> SEQUENCE: 46
tgctgctgcg agatttgaag                                               20

<210> SEQ ID NO 47
<211> LENGTH: 20
<212> TYPE: DNA
<213> ORGANISM: Artificial Sequence
<220> FEATURE:
<223> OTHER INFORMATION: Synthetic

<400> SEQUENCE: 47
```
gaagttcaac atcaagagca                                              20

<210> SEQ ID NO 48
<211> LENGTH: 19
<212> TYPE: DNA
<213> ORGANISM: Artificial Sequence
<220> FEATURE:
<223> OTHER INFORMATION: Synthetic

<400> SEQUENCE: 48
catagtccct ttggtccag                                               19

<210> SEQ ID NO 49
<211> LENGTH: 24
<212> TYPE: DNA
<213> ORGANISM: Artificial Sequence
<220> FEATURE:
<223> OTHER INFORMATION: Synthetic

<400> SEQUENCE: 49
tgaattccct gggtgagaag ctga                                         24

<210> SEQ ID NO 50
<211> LENGTH: 24
<212> TYPE: DNA
<213> ORGANISM: Artificial Sequence
<220> FEATURE:
<223> OTHER INFORMATION: Synthetic

<400> SEQUENCE: 50
tggccttgta gacaccttgg tctt                                         24

<210> SEQ ID NO 51
<211> LENGTH: 24
<212> TYPE: DNA
<213> ORGANISM: Artificial Sequence
<220> FEATURE:
<223> OTHER INFORMATION: Synthetic

<400> SEQUENCE: 51
aattgctgcc ttcgccctct ttac                                         24

<210> SEQ ID NO 52
<211> LENGTH: 24
<212> TYPE: DNA
<213> ORGANISM: Artificial Sequence
<220> FEATURE:
<223> OTHER INFORMATION: Synthetic

<400> SEQUENCE: 52
tgtacaggct gaggactttg gtgt                                         24

<210> SEQ ID NO 53
<211> LENGTH: 19
<212> TYPE: DNA
<213> ORGANISM: Artificial Sequence
<220> FEATURE:
<223> OTHER INFORMATION: Synthetic

<400> SEQUENCE: 53
ccggaccaga gaccctttg                                               19

<210> SEQ ID NO 54
<211> LENGTH: 23
<212> TYPE: DNA

```
<213> ORGANISM: Artificial Sequence
<220> FEATURE:
<223> OTHER INFORMATION: Synthetic

<400> SEQUENCE: 54
cctgtgggct tgttgaagta aaa                                              23

<210> SEQ ID NO 55
<211> LENGTH: 24
<212> TYPE: DNA
<213> ORGANISM: Artificial Sequence
<220> FEATURE:
<223> OTHER INFORMATION: Synthetic

<400> SEQUENCE: 55
gatgctcagc agtcaagtgc cttt                                             24

<210> SEQ ID NO 56
<211> LENGTH: 24
<212> TYPE: DNA
<213> ORGANISM: Artificial Sequence
<220> FEATURE:
<223> OTHER INFORMATION: Synthetic

<400> SEQUENCE: 56
gacatgtttg cggcatccag gtaa                                             24
```